(12) United States Patent
Kawamura et al.

(10) Patent No.: US 7,405,326 B2
(45) Date of Patent: Jul. 29, 2008

(54) AROMATIC AMINE DERIVATIVES AND ELECTROLUMINESCENCE DEVICE USING THE SAME

(75) Inventors: Masahiro Kawamura, Chiba (JP); Masakazu Funahashi, Chiba (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 0 days.

(21) Appl. No.: 11/428,969

(22) Filed: Jul. 6, 2006

(65) Prior Publication Data

US 2007/0029927 A1 Feb. 8, 2007

(30) Foreign Application Priority Data

Aug. 8, 2005 (JP) ............................. 2005-230127

(51) Int. Cl.
*C07C 211/00* (2006.01)
(52) U.S. Cl. .................................................. 564/427
(58) Field of Classification Search ................. 564/427
See application file for complete search history.

(56) References Cited

U.S. PATENT DOCUMENTS

| 4,720,432 | A | 1/1988 | VanSlyke et al. |
|---|---|---|---|
| 5,061,569 | A | 10/1991 | VanSlyke et al. |
| 5,639,914 | A | 6/1997 | Tomiyama et al. |
| 5,707,747 | A | 1/1998 | Tomiyama et al. |
| 6,517,957 | B1 | 2/2003 | Senoo et al. |
| 6,743,948 | B1 | 6/2004 | Hosokawa et al. |
| 2002/0137969 | A1 | 9/2002 | Hosokawa et al. |
| 2003/0018218 | A1 | 1/2003 | Hosokawa et al. |
| 2003/0157364 | A1 | 8/2003 | Senoo et al. |
| 2004/0054232 | A1 | 3/2004 | Hosokawa et al. |
| 2006/0186799 | A1 | 8/2006 | Hosokawa et al. |
| 2007/0029927 | A1 | 2/2007 | Kawamura et al. |

FOREIGN PATENT DOCUMENTS

| EP | 1666561 A1 | 6/2006 |
|---|---|---|
| JP | 3565870 | 9/1993 |
| JP | 3220950 | 5/1995 |
| JP | 3508984 | 2/1999 |
| JP | 11-135261 | 5/1999 |
| JP | 2000-12229 | 1/2000 |
| JP | 2000-012229 | * 1/2000 |
| JP | 2002-080433 | 3/2002 |
| JP | 2002-212151 | 7/2002 |
| WO | WO 00/39247 | 7/2000 |
| WO | WO 2006/039982 | 4/2006 |

OTHER PUBLICATIONS

U.S. Appl. No. 11/681,466, filed Mar. 2, 2007, Funahashi.
U.S. Appl. No. 11/428,969, filed Jul. 6, 2006, Kawamura et al.
U.S. Appl. No. 11/458,541, filed Jul. 19, 2006, Yabunouchi et al.
U.S. Appl. No. 11/378,332, filed Mar. 20, 2006, Hosokawa et al.

* cited by examiner

*Primary Examiner*—Samuel Barts
*Assistant Examiner*—Kellette Gale
(74) *Attorney, Agent, or Firm*—Oblon, Spivak, McClelland, Maier & Neustadt, P.C.

(57) ABSTRACT

An aromatic amine derivative with a specific structure and an organic electroluminescence device which comprises at least one organic thin film layer comprising a light emitting layer sandwiched between a pair of electrode consisting of an anode and a cathode, wherein at least one of the organic thin film layer comprises the aromatic amine derivative singly or as its mixture component. The organic electroluminescence device which exhibits an enhanced current efficiency of light emission and emits blue light with a prolonged lifetime is realized.

5 Claims, No Drawings

AROMATIC AMINE DERIVATIVES AND ELECTROLUMINESCENCE DEVICE USING THE SAME

TECHNICAL FIELD

The present invention relates to an organic electroluminescence ("electroluminescence" will be occasionally referred to as "EL", hereinafter) device. More particularly, it relates to an organic EL device employing an aromatic amine derivative as a light emitting material resultantly realizing a prolonged lifetime, an enhanced efficiently of light emission and a reasonable production cost.

BACKGROUND ART

An organic electroluminescence ("electroluminescence" will be occasionally referred to as "EL", hereinafter) device is a spontaneous light emitting device which utilizes the principle that a fluorescent substance emits light by energy of recombination of holes injected from an anode and electrons injected from a cathode when an electric field is applied. Since an organic EL device of the laminate type driven under a low electric voltage was reported by C. W. Tang et al. of Eastman Kodak Company (C. W. Tang and S. A. Vanslyke, Applied Physics Letters, Volume 51, Pages 913, 1987), many studies have been conducted on organic EL devices using organic materials as the constituting materials. Tang et al. used a laminate structure using tris(8-quinolinolato)aluminum for the light emitting layer and a triphenyldiamine derivative for the hole transporting layer. Advantages of the laminate structure are that the efficiency of hole injection into the light emitting layer can be increased, that the efficiency of forming excited particles which are formed by blocking and recombining electrons injected from the cathode can be increased, and that excited particles formed among the light emitting layer can be enclosed. As the structure of the organic EL device, a two-layered structure having a hole transporting (injecting) layer and an electron transporting and light emitting layer and a three-layered structure having a hole transporting (injecting) layer, a light emitting layer and an electron transporting (injecting) layer are well known. To increase the efficiency of recombination of injected holes and electrons in the devices of the laminate type, the structure of the device and the process for forming the device have been studied.

Conventionally, aromatic diamine derivatives described in patent Literature 1 below and aromatic diamine derivatives with condensed rings described in patent Literature 2 below have been known as hole transporting materials for the organic EL devices. Improving those aromatic amine derivatives, patent Literature 3 below discloses a following Compound (A), and patent Literature 4 below discloses an aromatic diamine compound represented by a following general formula (B).

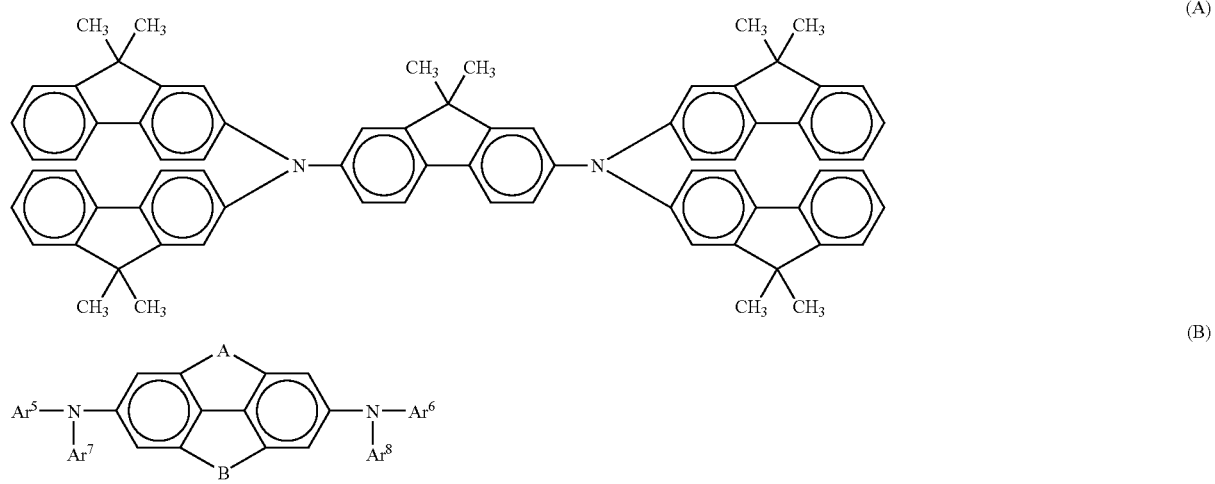

In the general formula (B), at least one of A or B is an atomic group forming a substituted or unsubstituted saturated 5 to 8 member-ring which may comprise a spiro bond.

Further, patent Literature 5 below discloses an organic EL device employing an aromatic triamine compound represented by a following general formula (C). Furthermore, Patent Literature 6 below discloses an aromatic tetraamine compound represented by a following general formula (D).

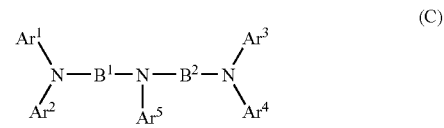

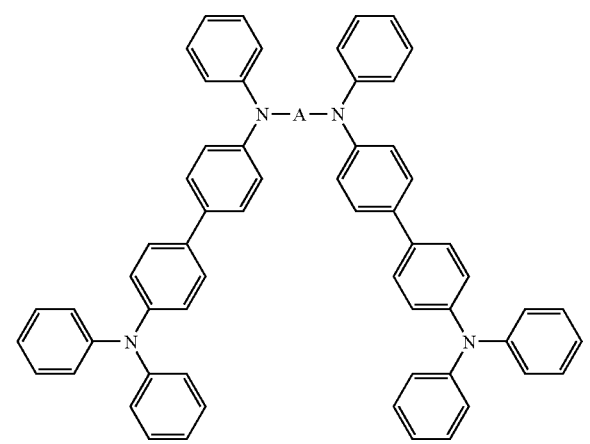

In the general formula (C), $B^1$ and $B^2$ each independently represents a substituted or unsubstituted biphenylene group. A in the general formula (D) is selected among the following structures.

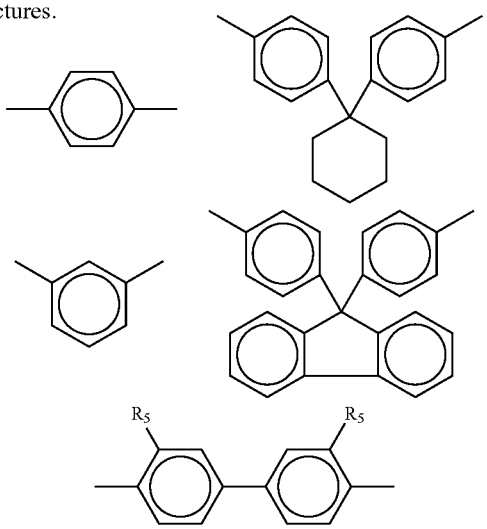

Still further, patent Literature 7 below and patent Literature 8 below each discloses 9-phenanthreneamine derivatives represented by a following general formula (E) and a following general formula (F) respectively.

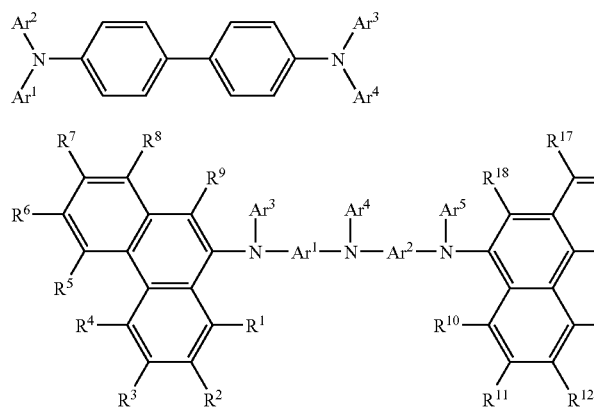

$Ar^1$ to $Ar^4$ in the general formula (E) are expressed by a following structure.

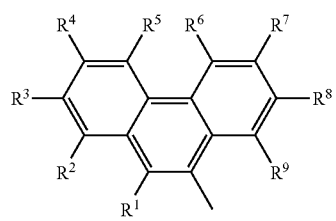

Although the organic EL devices employing those materials exhibit improvement, they do not achieve practical performance yet and accordingly, further prolonged lifetime, further enhanced efficiency of light emission and further acceralated mobility were eagerly demanded.

Patent Literature 1: U.S. Pat. No. 4,720,432
Patent Literature 2: U.S. Pat. No. 5,061,569
Patent Literature 3: Japanese Registered Patent No. 3508984
Patent Literature 4: Japanese Unexamined Patent Application Laid-Open No. 2002-080433
Patent Literature 5: Japanese Registered Patent No. 3565870
Patent Literature 6: Japanese Registered Patent No. 3220950
Patent Literature 7: Japanese Unexamined Patent Application Laid-Open No. Heisei 11 (1999)-135261
Patent Literature 8: Japanese Unexamined Patent Application Laid-Open No. 2002-212151

DISCLOSURE OF THE INVENTION

The present invention has been made to overcome the above problems and has an object of providing a material comprising an aromatic amine derivative for an organic EL device satisfying a reduction of its driving voltage and an enhancement of its efficiency of light emission simultaneously, together with maintaining its prolonged lifetime.

As a result of extensive researches for overcoming the above problems, the inventors have found that by employing an aromatic amine derivative represented by any one of following general formulae (1) to (3) and (5), an organic EL device with low driving voltage and with an enhanced efficiency of light emission together with maintaining its prolonged lifetime can be fabricated. Such being the case, the present invention has been accomplished on the basis of the foregoing findings and information.

Thus, the present invention provides an aromatic amine derivative represented by any one of following general formulae (1) to (3):

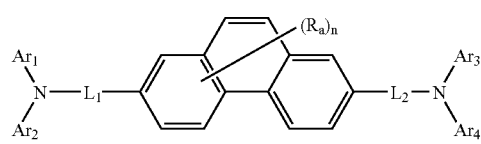

(1)

wherein $Ar_1$ to $Ar_4$ each independently represents a substituted or unsubstituted aryl group having 6 to 30 ring carbon atoms or a substituted or unsubstituted heteroaryl group having 5 to 30 ring carbon atoms; $L_1$ and $L_2$ each independently represents a single bond, a substituted or unsubstituted arylene group having 6 to 30 ring carbon atoms, a substituted or unsubstituted heteroarylene group having 5 to 30 ring carbon atoms; when both $L_1$ and $L_2$ are single bonds, however, a case where both $Ar_1$ and $Ar_3$ each represents a substituted or unsubstituted phenyl group and further, a case where both $Ar_2$ and $Ar_4$ each represents a substituted or unsubstituted biphenylyl group or a substituted or unsubstituted phenyl group is excluded; $R_a$ represents a substituent and when R exists two or more, they may bond each other to form a ring; and n represents an integer of 0 to 8.

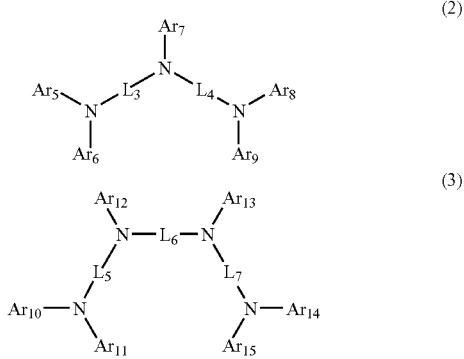

In the general formulae (2) and (3), $Ar_5$ to $Ar_{15}$ each independently represents a substituted or unsubstituted aryl group having 6 to 30 ring carbon atoms or a substituted or unsubstituted heteroaryl group having 5 to 30 ring carbon atoms; $L_3$ to $L_7$ each independently represents a substituted or unsubstituted arylene group having 6 to 30 ring carbon atoms, a substituted or unsubstituted heteroarylene group having 5 to 30 ring carbon atoms; and further, at least one of $L_3$ or $L_4$ in the general formula (2) or at least one of $L_5$ to $L_7$ in the general formula (3) is a coupling group expressed by a following general formula (4):

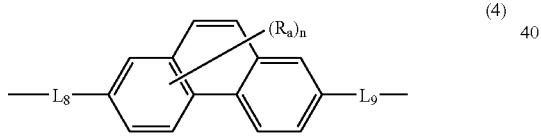

wherein $L_8$ and $L_9$ each independently represents a single bond, a substituted or unsubstituted arylene group having 6 to 30 ring carbon atoms or a substituted or unsubstituted heteroarylene group having 5 to 30 ring carbon atoms; $R_a$ represents a substituent and when $R_a$ exists two or more, they may bond each other to form a ring; and n represents an integer of 0 to 8.

Further, the present invention provides a material for an organic EL device comprising the aromatic amine derivative represented by any one of the above general formulae (1) to (3), together with a material for an organic EL device represented by a following general formula (5):

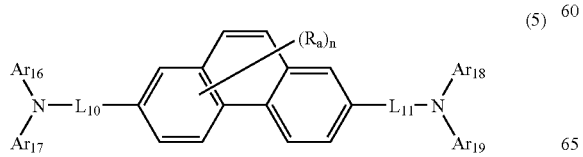

wherein $Ar_{16}$ to $Ar_{19}$ each independently represents a substituted or unsubstituted aryl group having 6 to 30 ring carbon atoms or a substituted or unsubstituted heteroaryl group having 5 to 30 ring carbon atoms; $L_{10}$ and $L_{11}$ each independently represents a single bond, a substituted or unsubstituted arylene group having 6 to 30 ring carbon atoms or a substituted or unsubstituted heteroarylene group having 5 to 30 ring carbon atoms; $R_a$ represents a substituent and when $R_a$ exists two or more, they may bond each other to form a ring; and n represents an integer of 0 to 8.

The material for the organic EL device of the present invention is employable as a hole injecting material, a hole transporting material or a dopant.

The present invention provides an organic EL device which comprises at least one organic thin film layer comprising a light emitting layer sandwiched between an anode and a cathode, wherein at least one of the organic thin film layer comprises the material for the organic EL device singly or as its mixture component.

In the organic EL device of the present invention, the material for the organic EL device is employed for at least one of a hole injecting region or a hole transporting region.

In the organic EL device of the present invention, the material for the organic EL device is employed for at least one of a hole injecting layer or a hole transporting layer.

In the organic EL device of the present invention, the material for the organic EL device is employed for a light emitting layer.

In the organic EL device of the present invention, the light emitting layer contains the material for the organic EL device in an amount of 0.1 to 20% by weight.

The organic EL device of the present invention emits bluish light.

It is particularly preferable that the material for the organic EL device of the present invention is employed for the hole transporting region; and further preferably, a superior organic EL device is obtainable when the material for the organic EL device of the present invention is employed for the hole transporting layer.

EFFECTS OF THE INVENTION

When the material for the organic EL device represented by any one of the general formulae (1) to (3), and (5) is employed for any one of the organic thin film layers, preferably for the hole transporting region or the light emitting region, more preferably for the hole transporting layer or the light emitting layer, and further more preferably for the hole transporting layer, it enables to fabricate the organic EL device which emits blue light at low driving voltage, with an enhanced efficiency of light emission and with prolonged lifetime.

THE PREFERRED EMBODIMENT TO CARRY OUT THE INVENTION

The present invention provides an aromatic amine derivative represented by any one of following general formulae (1) to (3):

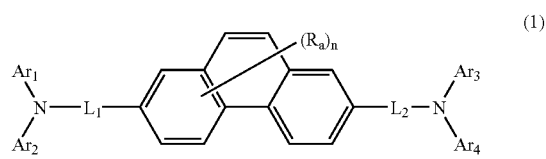

In the general formula (1), $Ar_1$ to $Ar_4$ each independently represents a substituted or unsubstituted aryl group having 6 to 30 ring carbon atoms or a substituted or unsubstituted heteroaryl group having 5 to 30 ring carbon atoms; $L_1$ and $L_2$ each independently represents a single bond, a substituted or unsubstituted arylene group having 6 to 30 ring carbon atoms or a substituted or unsubstituted heteroarylene group having 5 to 30 ring carbon atoms; when both $L_1$ and $L_2$ are single bonds, however, a case where both $Ar_1$ and $Ar_3$ each represents a substituted or unsubstituted phenyl group and further, where both $Ar_2$ and $Ar_4$ each represents a substituted or unsubstituted biphenylyl group or a substituted or unsubstituted phenyl group is excluded; $R_a$ represents a substituent and when $R_a$ exists two or more, they may bond each other to form a ring; and n represents an integer of 0 to 8.

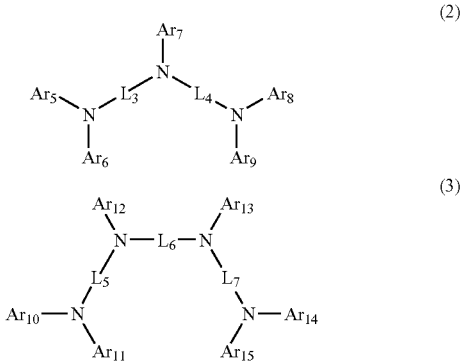

(2)

(3)

In the general formulae (2) and (3), $Ar_5$ to $Ar_{15}$ each independently represents a substituted or unsubstituted aryl group having 6 to 30 ring carbon atoms or a substituted or unsubstituted heteroaryl group having 5 to 30 ring carbon atoms; $L_3$ to $L_7$ each independently represents a substituted or unsubstituted arylene group having 6 to 30 ring carbon atoms or a substituted or unsubstituted heteroarylene group having 5 to 30 ring carbon atoms; and further, at least one of $L_3$ or $L_4$ in the general formula (2) or at least one of $L_5$ to $L_7$ in the general formula (3) is a coupling group expressed by a following general formula (4):

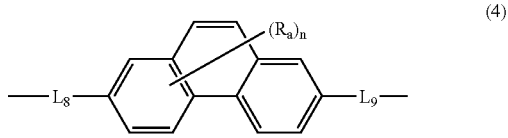

(4)

wherein $L_8$ and $L_9$ each independently represents a single bond, a substituted or unsubstituted arylene group having 6 to 30 ring carbon atoms, a substituted or unsubstituted heteroarylene group having 5 to 30 ring carbon atoms; $R_a$ represents a substituent and when $R_a$ exists two or more, they may bond each other to form a ring; and n represents an integer of 0 to 8.

Examples of the substituted or unsubstituted aryl group having 6 to 30 ring carbon atoms include phenyl group, 1-naphthyl group, 2-naphthyl group, 1-anthracenyl group, 2-anthracenyl group, 9-anthracenyl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 3-methyl-2-naphthyl group, 4-methyl-1-naphthyl group, 4-methyl-1-anthryl group, 4'-methylbiphenyl-yl group, 4"-t-butyl-p-terphenyl-4-yl group, fluorenyl group, etc. Preferable examples are phenyl group, naphthyl group, biphenylyl group, terphenylyl group and phenanthryl group.

Examples of a substituted or unsubstituted fused aromatic group having 10 to 20 ring carbon atoms include naphthyl group, phenanthryl group, anthranyl group, pyrenyl group, crycenyl group, acenaphthyl group, fluorenyl group, and so on; preferably naphthyl group and phenanthryl group. Preferable examples include phenyl group, naphthyl group, biphenyl group, anthranil group, phenanthryl group, pyrenyl group, crycenyl group and fluorenyl group. Particularly preferable examples are phenyl group and naphthyl group.

Examples of the substituted or unsubstituted heteroarylene group having 5 to 30 ring carbon atoms include pyridyl group, pyrazyl group, quinolyl group, isoquinolyl group, phenanthroryl group, furyl group, benzofuryl group, dibenzofuryl group, thienyl group, dibenzothienyl group, benzothienyl group, pyrrolyl group, indolyl group, carbazolyl group, imidazolyl group, benzimidazolyl group, etc. Preferable examples are pyridyl group, quinolyl group, carbazolyl group and indolyl group.

Examples of the substituted or unsubstituted arylene group having 6 to 30 ring carbon atoms include phenylene group, biphenylene group, terphenylene group, quarterphenylene group, naphthylene group, anthracenylene group, phenanthrylene group, chrycenylene group, a pyrenylene group, fluorenylene group, 2,6-diphenylnaphthalene-4',4"-ene group, 2-phenylnaphthalene-2,4'-ene group, etc. Preferable examples are phenylene group, biphenylene group, terphenylene group, fluorenylene group and naphthylene group.

Examples of the substituted or unsubstituted heteroaryl group having 5 to 30 ring carbon atoms include monovalent group of pyridine, quinoline, thiophene, furan, carbazole, dibenzofuran, dibenzothiophene, fluorenone, oxazole, oxadiazole, thiadiazole, etc. Preferable examples are pyridine, carbazole and thiophene.

Examples of the substituted or unsubstituted heteroarylene group having 5 to 30 ring carbon atoms include pyridyl group, pyrazyl group, quinolyl group, isoquinolyl group, phenanthroryl group, furyl group, benzofuryl group, dibenzofuryl group, thienyl group, dibenzothienyl group, benzothienyl group, pyrrolyl group, indolyl group, carbazolyl group, imidazolyl group, benzimidazolyl group, etc. Preferable examples are pyridyl group, quinolyl group, carbazolyl group and indolyl group.

Examples of the substituent for the aryl group, arylene group, heteroaryl group and heteroarylene group include alkyl group (alkyl group preferably having 1 to 20 carbon atoms, more preferably having 1 to 12 carbon atoms and particularly preferably having 1 to 8 carbon atoms; examples include methyl group, ethyl group, iso-propyl group, tert-butyl group, n-octyl group, n-decyl group, n-hexadecyl group, cyclopropyl group, cyclopentyl group, cyclohexyl group, etc.); alkenyl group (alkenyl group preferably having 2 to 20 carbon atoms, more preferably having 2 to 12 carbon atoms and particularly preferably having 2 to 8 carbon atoms; examples include vinyl group, allyl group, 2-butenyl group, 3-pentenyl group, etc.); alkynyl group (alkynyl group preferably having 2 to 20 carbon atoms, more preferably having 2 to 12 carbon atoms and particularly preferably having 2 to 8 carbon atoms; examples include propargyl group, 3-pentynyl group, etc.); amino group (amino group preferably having 0 to 20 carbon atoms, more preferably having 0 to 12 carbon atoms and particularly preferably having 0 to 6 carbon atoms; examples include amino group, methylamino group, dimethylamino group, diethylamino group, diphenylamino group, dibenzylamino group, etc.); alkoxy group (alkoxy group preferably having 1 to 20 carbon atoms, more preferably having 1 to 12 carbon atoms and particularly preferably having 1 to 8 carbon atoms; examples include methoxy group, ethoxy group, butoxy group, etc.); aryloxy group (aryloxy group preferably having 6 to 20 carbon atoms, more preferably having 6 to 16 carbon atoms and particularly preferably having 6 to 12 carbon atoms; examples include phenyloxy group, 2-naphthyloxy group, etc.); acyl group (acyl group preferably having 1 to 20 carbon atoms, more preferably having 1 to 16 carbon atoms and particularly preferably having 1 to 12 carbon atoms; examples include acetyl group, benzoyl group, formyl group, pivaloyl group, etc.); alkoxycarbonyl group (alkoxycarbonyl group preferably having 2 to 20 carbon atoms, more preferably having 2 to 16 carbon atoms and particularly preferably having 2 to 12 carbon atoms; examples include methoxycarbonyl group, ethoxycarbonyl group, etc.); aryloxycarbonyl group (aryloxycarbonyl group preferably having 7 to 20 carbon atoms, more preferably having 7 to 16 carbon atoms and particularly preferably having 7 to 10 carbon atoms; examples include phenyloxycarbonyl group, etc.); acyloxy group (acyloxy group preferably having 2 to 20 carbon atoms, more preferably having 2 to 16 carbon atoms and particularly preferably having 2 to 10 carbon atoms; examples include acetoxy group, benzoyloxy group, etc.); acylamino group (acylamino group preferably having 2 to 20 carbon atoms, more preferably having 2 to 16 carbon atoms and particularly preferably having 2 to 10 carbon atoms; examples include acetylamino group, benzoylamino group, etc.); alkoxycarbonylamino group (alkoxycarbonylamino group preferably having 2 to 20 carbon atoms, more preferably having 2 to 16 carbon atoms and particularly preferably having 2 to 12 carbon atoms; examples include methoxycarbonylamino group, etc.); aryloxycarbonylamino group (aryloxycarbonylamino group preferably having 7 to 20 carbon atoms, more preferably having 7 to 16 carbon atoms and particularly preferably having 7 to 12 carbon atoms; examples include phenyloxycarbonylamino group, etc.); sulfonylamino group (sulfonylamino group preferably having 1 to 20 carbon atoms, more preferably having 1 to 16 carbon atoms and particularly preferably having 1 to 12 carbon atoms; examples include methanesulfonylamino group, benzensulfonylamino group, etc.); sulfamoyl group (sulfamoyl group preferably having 0 to 20 carbon atoms, more preferably having 0 to 16 carbon atoms and particularly preferably having 0 to 12 carbon atoms; examples include sulfamoyl group, methylsulfamoyl group, dimethylsulfamoyl group, phenylsulfamoyl group, etc.); carbamoyl group (carbamoyl group preferably having 1 to 20 carbon atoms, more preferably having 1 to 16 carbon atoms and particularly preferably having 1 to 12 carbon atoms; examples include carbamoyl group, methylcarbamoyl group, diethylcarbamoyl group, phenylcarbamoyl group, etc.); alkylthio group (alkylthio group preferably having 1 to 20 carbon atoms, more preferably having 1 to 16 carbon atoms and particularly preferably having 1 to 12 carbon atoms; examples include methylthio group, ethylthio group, etc.); arylthio group (arylthio group preferably having 6 to 20 carbon atoms, more preferably having 6 to 16 carbon atoms and particularly preferably having 6 to 12 carbon atoms; examples include phenylthio group, etc.); sulfonyl group (sulfonyl group preferably having 1 to 20 carbon atoms, more preferably having 1 to 16 carbon atoms and particularly preferably having 1 to 12 carbon atoms; examples include mesyl group, tosyl group, etc.); sulfinyl group (sulfinyl group preferably having 1 to 20 carbon atoms, more preferably having 1 to 16 carbon atoms and particularly preferably having 1 to 12 carbon atoms; examples include methanesulfinyl group, benzenesulfinyl group, etc.); ureide group (ureide group preferably having 1 to 20 carbon atoms, more preferably having 1 to 16 carbon atoms and particularly preferably having 1 to 12 carbon atoms; examples include ureide group, methylureide group, phenylureide group, etc.); phosphoricamide group (phosphoricamide group preferably having 1 to 20 carbon atoms, more preferably having 1 to 16 carbon atoms and particularly preferably having 1 to 12 carbon atoms; examples include diethylphosphoricamide group, phenylphosphateamide group, etc.); hydroxy group; mercapto group; halogen atom (for example, fluorine atom, chlorine atom, bromine atom, iodine atom); cyano group; sulfo group; carboxyl group; nitro group; hydroxamicacid group; sulfino group; hydrazino group; imino group; heterocyclic group (heterocyclic group preferably having 1 to 30 carbon atoms, more preferably having 1 to 12 carbon atoms; examples of the hetero atom include nitrogen atom, oxygen atom, sulfur atom; specific examples of the heterocyclic group include imidazolyl, pyridyl, quinolyl, furyl, thienyl, piperidyl, morpholino, benzoxazolyl, benzimidazolyl, benzothiazolyl, carbazolyl, etc.); silyl group (silyl group preferably having 3 to 40 carbon atoms, more preferably having 3 to 30 carbon atoms and particularly preferably having 3 to 24 carbon atoms; examples include trimethylsilyl group, triphenylsilyl group, etc.); etc. Those substituent may be further substituted. Furthermore, when there are two or more substituents, the substituents may be the same with or different from each other. Moreover, in a case where it is possible, they may couple each other to form a ring.

Examples of the substituent $R_a$ in the general formulae (1) to (4) include alkyl group (alkyl group preferably having 1 to 20 carbon atoms, more preferably having 1 to 12 carbon atoms and particularly preferably having 1 to 8 carbon atoms; examples include methyl group, ethyl group, iso-propyl group, t-butyl group, n-octyl group, n-decyl group, n-hexadecyl group, cyclopropyl group, cyclopentyl group, cyclohexyl group, etc.); alkenyl group (alkenyl group preferably having 2 to 20 carbon atoms, more preferably having 2 to 12 carbon atoms and particularly preferably having 2 to 8 carbon atoms; examples include vinyl group, allyl group, 2-butenyl group, 3-pentenyl group, etc.); alkynyl group (alkynyl group preferably having 2 to 20 carbon atoms, more preferably having 2 to 12 carbon atoms and particularly preferably having 2 to 8 carbon atoms; examples include propargyl group, 3-pentynyl group, etc.); amino group (amino group preferably having 0 to 20 carbon atoms, more preferably having 0 to 12 carbon atoms and particularly preferably having 0 to 6 carbon atoms; examples include amino group, methylamino group, dimethylamino group, diethylamino group, diphenylamino group, dibenzylamino group, etc.); alkoxy group (alkoxy group preferably having 1 to 20 carbon atoms, more preferably having 1 to 12 carbon atoms and particularly preferably having 1 to 8 carbon atoms; examples include methoxy group, ethoxy group, butoxy group, etc.); aryloxy group (aryloxy group preferably having 6 to 20 carbon atoms, more preferably having 6 to 16 carbon atoms and particularly preferably having 6 to 12 carbon atoms; examples include phenyloxy group, 2-naphthyloxy group, etc.); acyl group (acyl group preferably having 1 to 20 carbon atoms, more preferably having 1 to 16 carbon atoms and particularly preferably having 1 to 12 carbon atoms; examples include acetyl group, benzoyl group, formyl group, pivaloyl group, etc.); alkoxycarbonyl group (alkoxycarbonyl group preferably having 2 to 20 carbon atoms, more preferably having 2 to 16 carbon atoms and particularly preferably having 2 to 12 carbon atoms; examples include methoxycarbonyl group, ethoxycarbonyl group, etc.); aryloxycarbonyl group (aryloxycarbonyl group preferably having 7 to 20 carbon atoms, more preferably having 7 to 16 carbon atoms and particularly preferably having 7 to 10 carbon atoms; examples include phenyloxycarbonyl group, etc.); acyloxy group (acyloxy group preferably having 2 to 20 carbon atoms, more preferably having 2 to 16 carbon atoms and particularly preferably having 2 to 10 carbon atoms; examples include acetoxy group, benzoyloxy group, etc.); acylamino group (acylamino group preferably having 2 to 20 carbon atoms, more preferably having 2 to 16 carbon atoms and particularly preferably having 2 to 10 carbon atoms; examples include acetylamino group, benzoylamino group, etc.); alkoxycarbonylamino group (alkoxycarbonylamino group preferably having 2 to 20 carbon atoms, more preferably having 2 to 16 carbon atoms and particularly preferably having 2 to 12 carbon atoms; examples include methoxycarbonylamino group, etc.); aryloxycarbonylamino group (aryloxycarbonylamino group preferably having 7 to 20 carbon atoms, more preferably having 7 to 16 carbon atoms and particularly preferably having 7 to 12 carbon atoms; examples include phenyloxycarbonylamino group, etc.); sulfonylamino group (sulfonylamino group preferably having 1 to 20 carbon atoms, more preferably having 1 to 16 carbon atoms and particularly preferably having 1 to 12 carbon atoms; examples include methanesulfonylamino group, benzensulfonylamino group, etc.); sulfamoyl group (sulfamoyl group preferably having 0 to 20 carbon atoms, more preferably having 0 to 16 carbon atoms and particularly preferably having 0 to 12 carbon atoms; examples include sulfamoyl group, methylsulfamoyl group, dimethylsulfamoyl group, phenylsulfamoyl group, etc.); carbamoyl group (carbamoyl group preferably having 1 to 20 carbon atoms, more preferably having 1 to 16 carbon atoms and particularly preferably having 1 to 12 carbon atoms; examples include carbamoyl group, methylcarbamoyl group, diethylcarbamoyl group, phenylcarbamoyl group, etc.); alkylthio group (alkylthio group preferably having 1 to 20 carbon atoms, more preferably having 1 to 16 carbon atoms and particularly preferably having 1 to 12 carbon atoms; examples include methylthio group, ethylthio group, etc.); arylthio group (arylthio group preferably having 6 to 20 carbon atoms, more preferably having 6 to 16 carbon atoms and particularly preferably having 6 to 12 carbon atoms; examples include phenylthio group, etc.); sulfonyl group (sulfonyl group preferably having 1 to 20 carbon atoms, more preferably having 1 to 16 carbon atoms and particularly preferably having 1 to 12 carbon atoms; examples include mesyl group, tosyl group, etc.); sulfinyl group (sulfinyl group preferably having 1 to 20 carbon atoms, more preferably having 1 to 16 carbon atoms and particularly preferably having 1 to 12 carbon atoms; examples include methanesulfinyl group, benzenesulfinyl group, etc.); ureide group (ureide group preferably having 1 to 20 carbon atoms, more preferably having 1 to 16 carbon atoms and particularly preferably having 1 to 12 carbon atoms; examples include ureide group, methylureide group, phenylureide group, etc.); phosphoricamide group (phosphoricamide group preferably having 1 to 20 carbon atoms, more preferably having 1 to 16 carbon atoms and particularly preferably having 1 to 12 carbon atoms; examples include diethylphosphoricamide group, phenylphosphateamide group, etc.); hydroxy group; mercapto group; halogen atom (for example, fluorine atom, chlorine atom, bromine atom, iodine atom); cyano group; sulfo group; carboxyl group; nitro group; hydroxamicacid group; sulfino group; hydrazino group; imino group; heterocyclic group (heterocyclic group preferably having 1 to 30 carbon atoms, more preferably having 1 to 12 carbon atoms; examples of the hetero atom include nitrogen atom, oxygen atom, sulfur atom; specific examples of the heterocyclic group include imidazolyl, pyridyl, quinolyl, furyl, thienyl, piperidyl, morpholino, benzoxazolyl, benzimidazolyl, benzothiazolyl, carbazolyl, etc.); silyl group (silyl group preferably having 3 to 40 carbon atoms, more preferably having 3 to 30 carbon atoms and particularly preferably having 3 to 24 carbon atoms; examples include trimethylsilyl group, triphenylsilyl group, etc.); etc. Those substituent may be further substituted. Furthermore, when there are two or more substituents, the substituents may be the same with or different from each other. Moreover, in a case where it is possible, they may couple each other to form a ring.

Specific examples of aromatic amine derivative represented by the general formulae (1) to (3) will be shown below, though not particularly limited thereto.

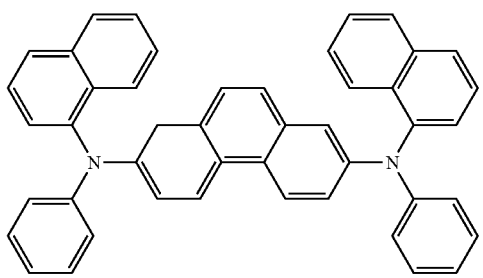
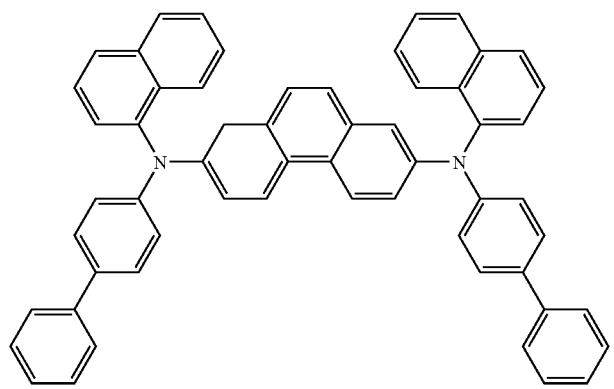

-continued
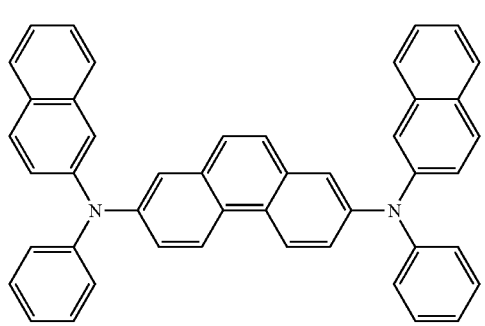
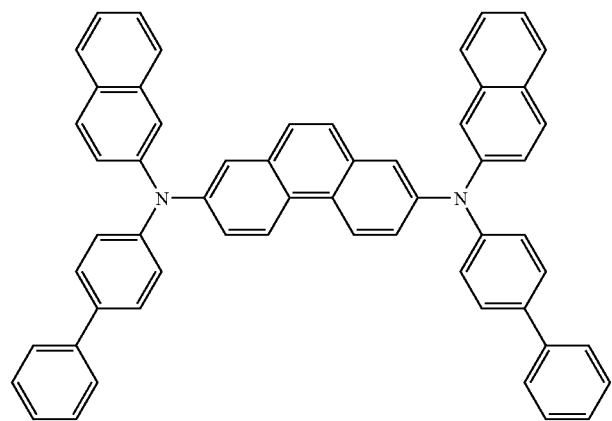
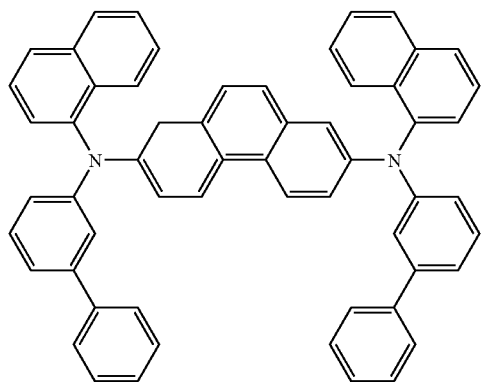
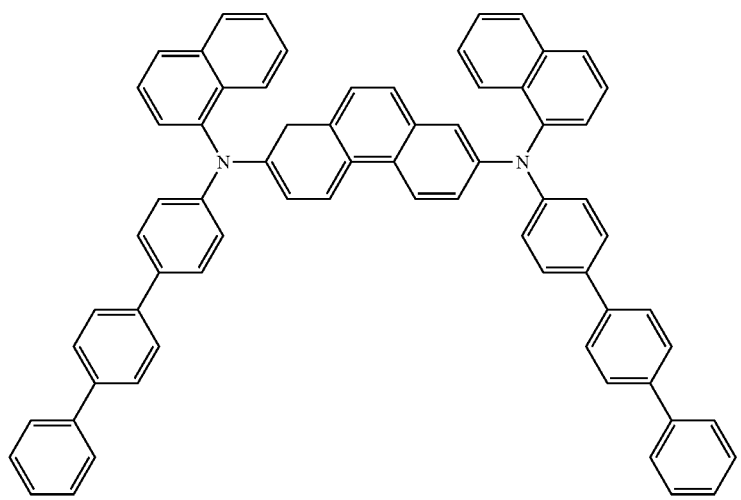

-continued
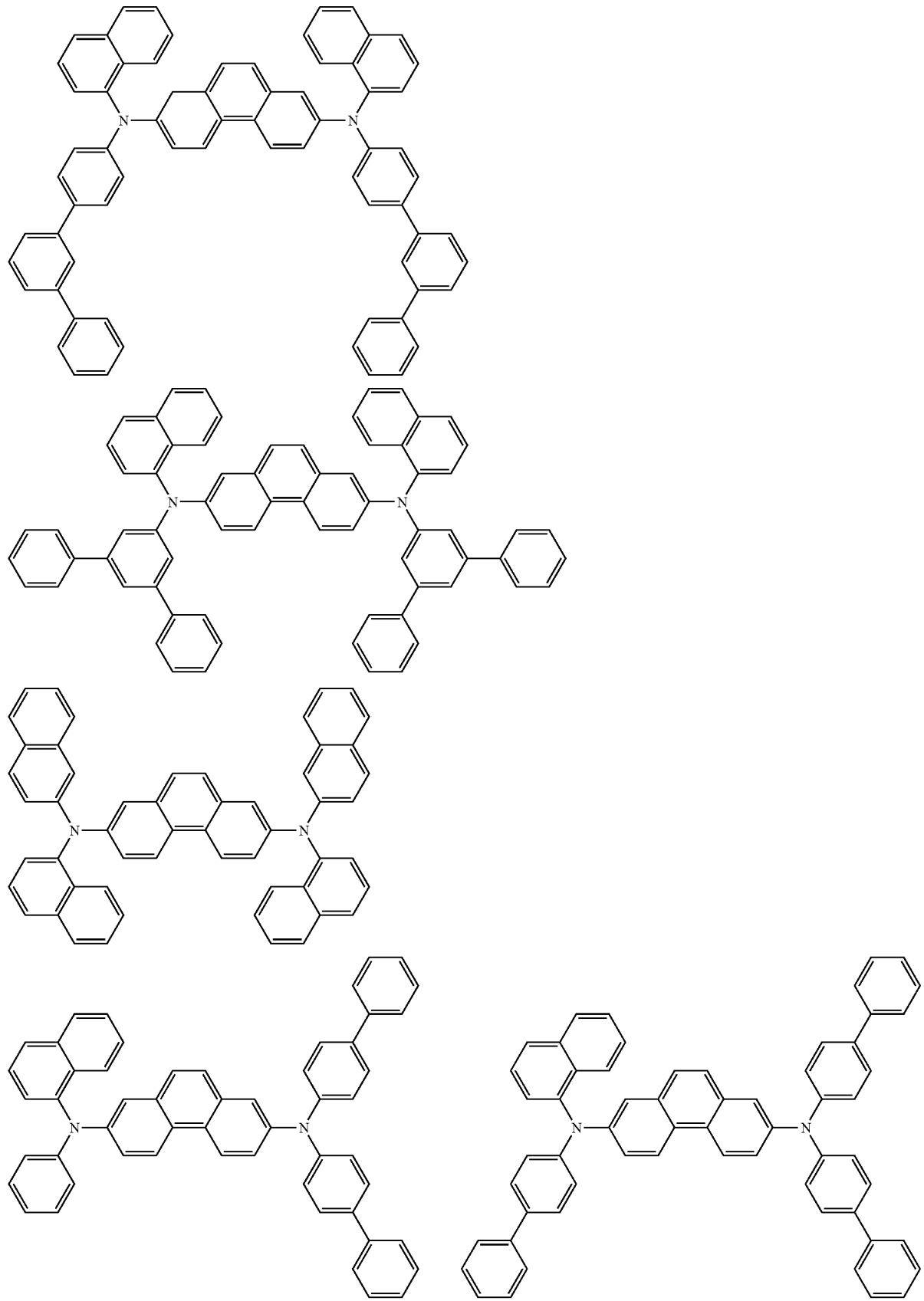

-continued
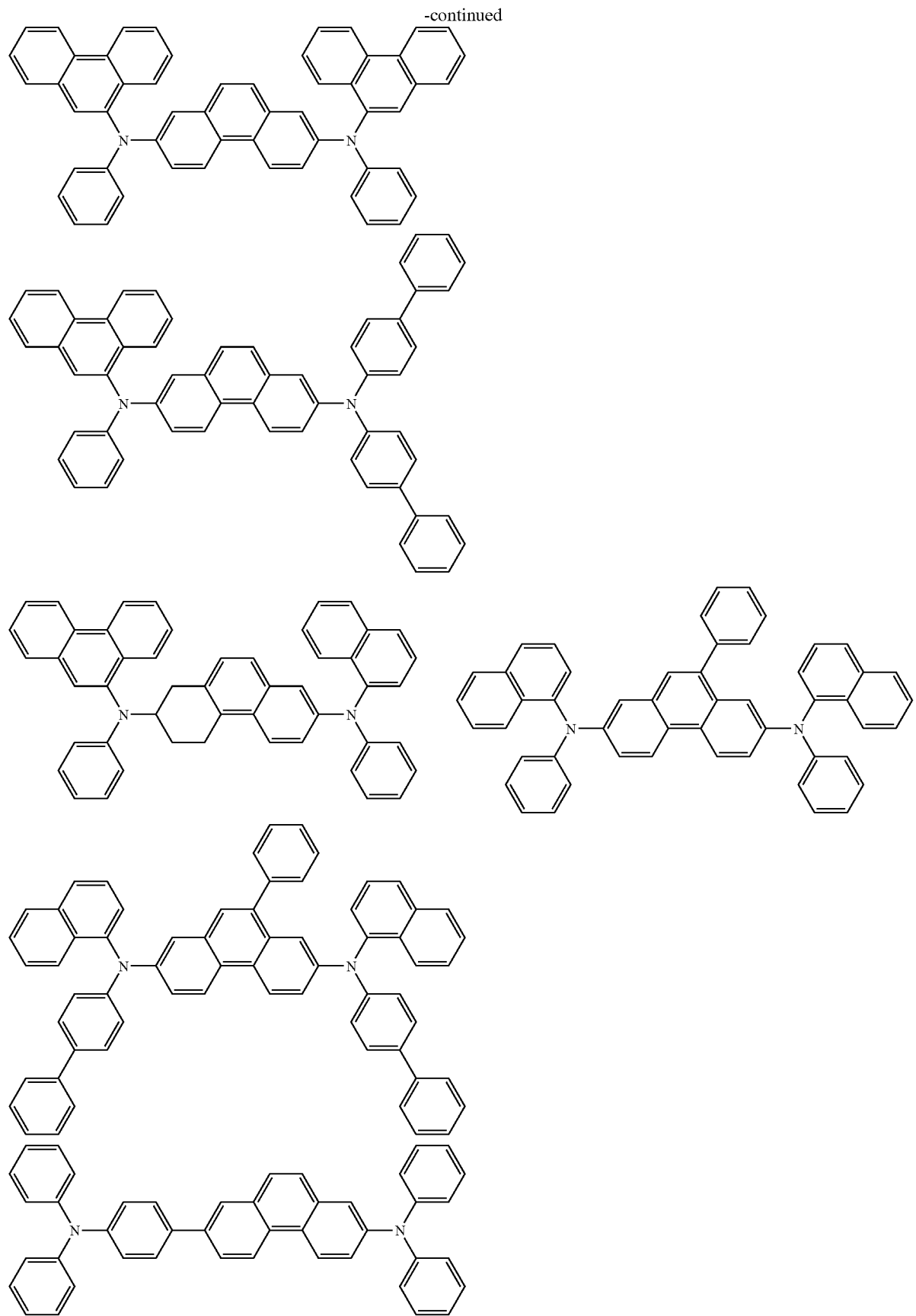

-continued
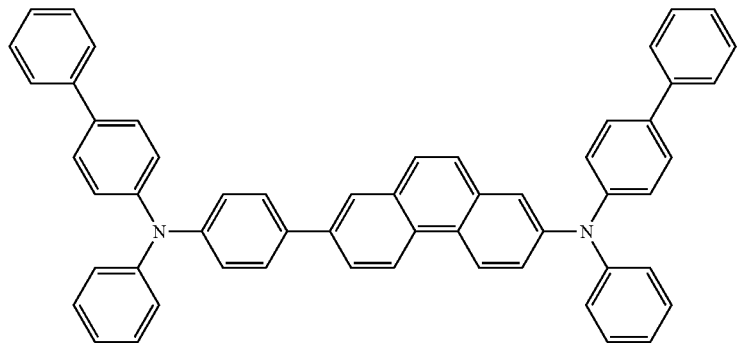
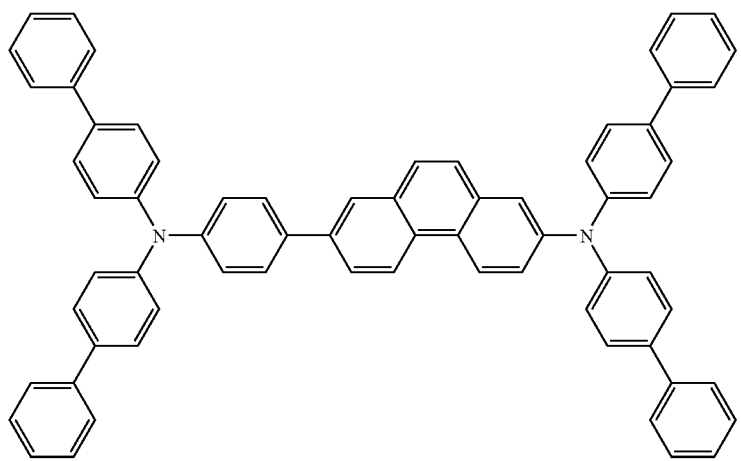
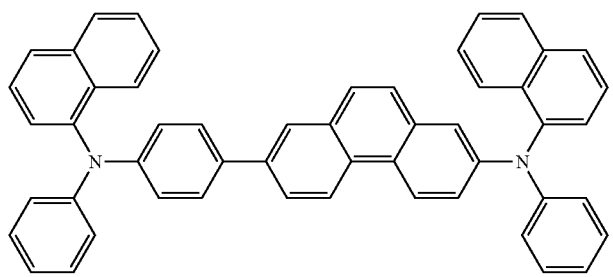
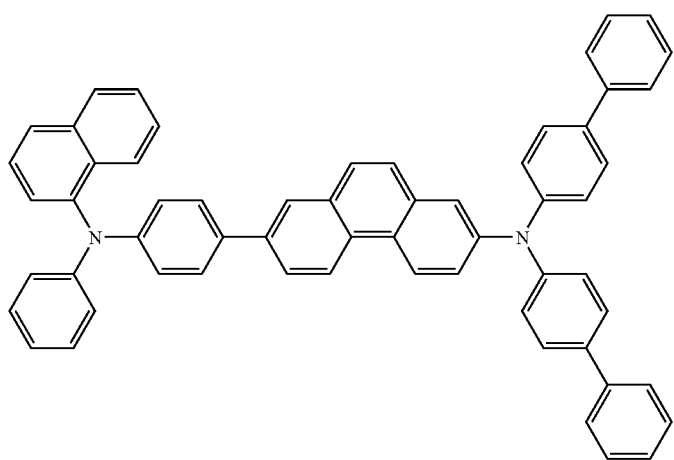

-continued
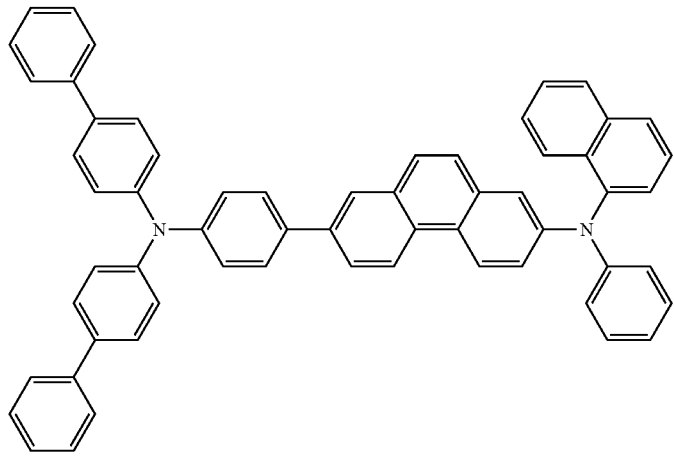
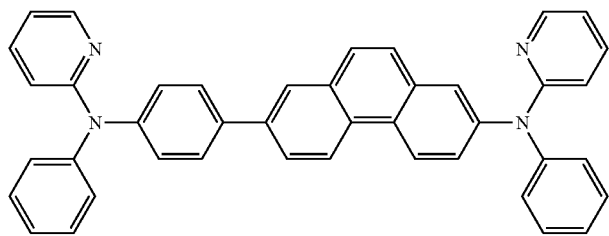
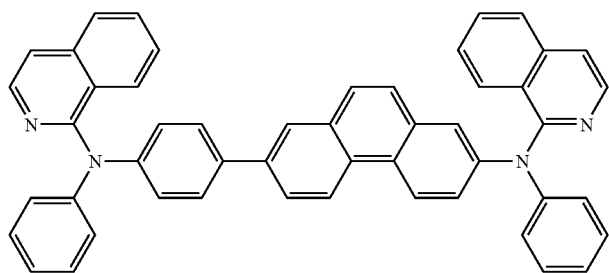
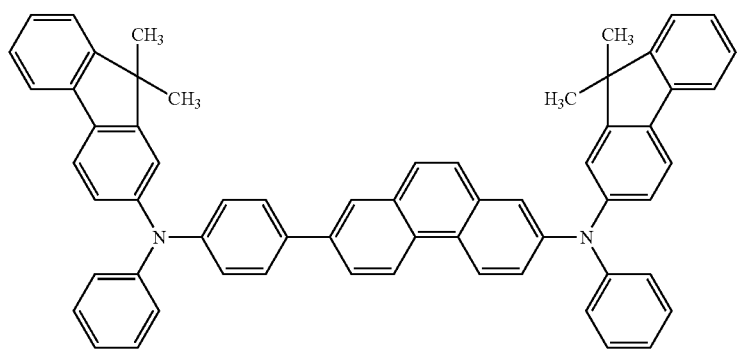

-continued
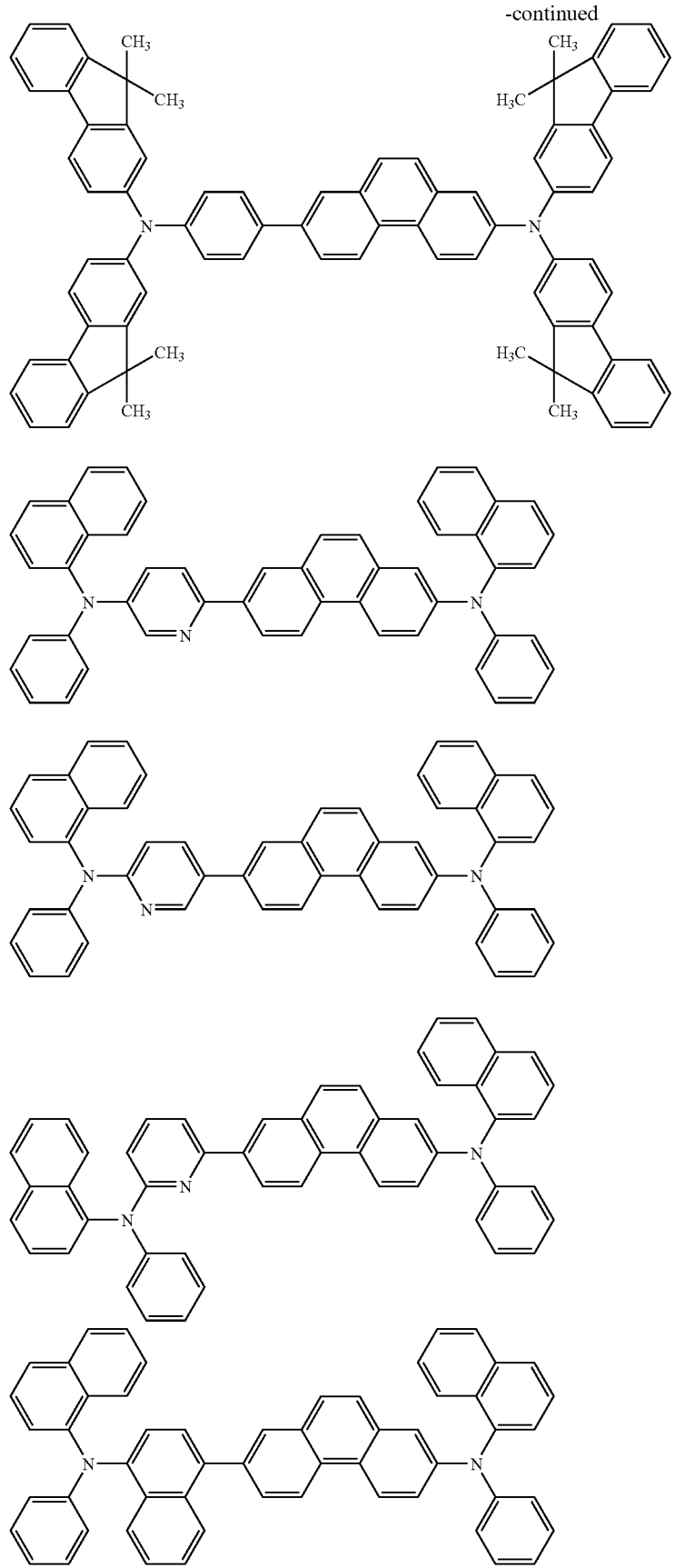

-continued
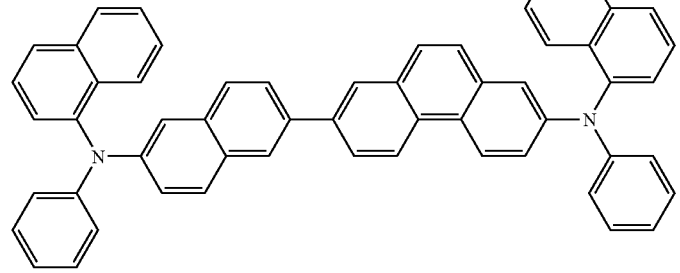
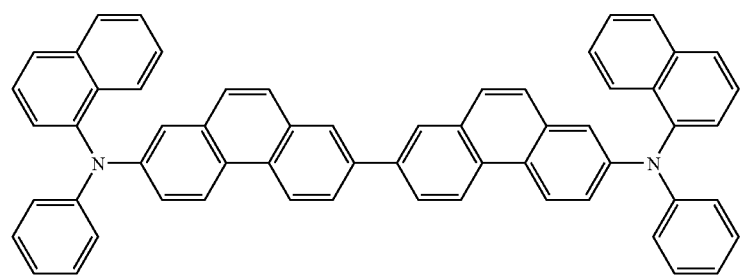
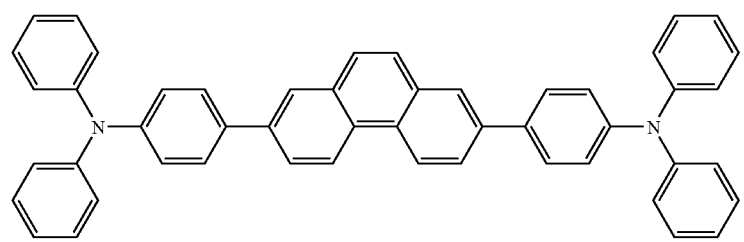
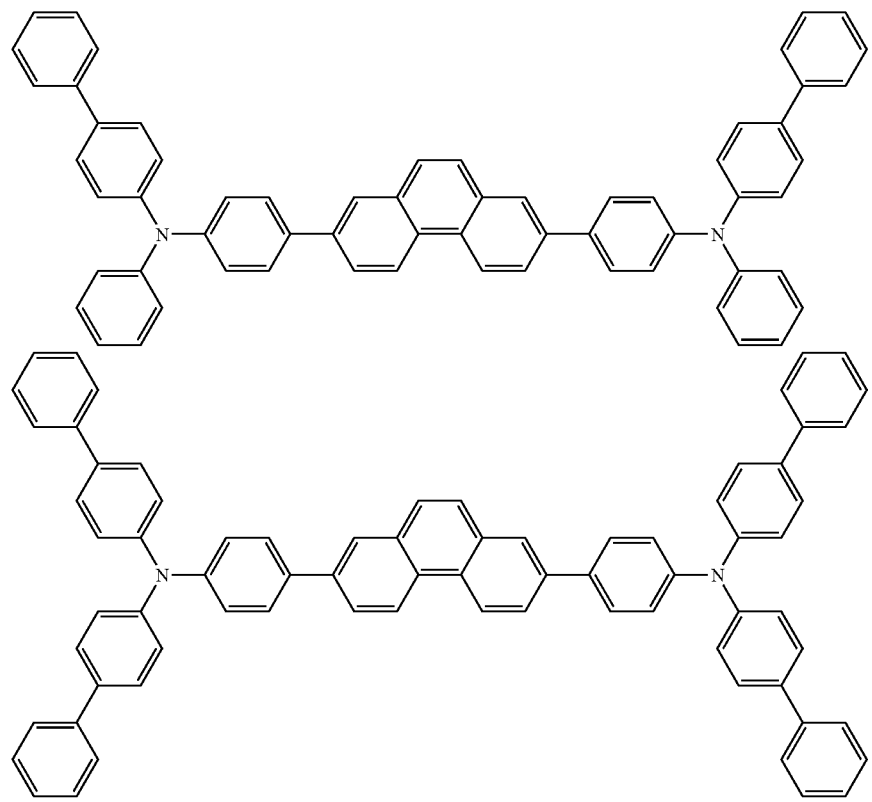

-continued
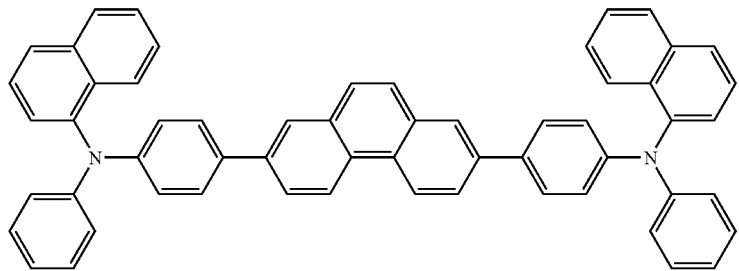
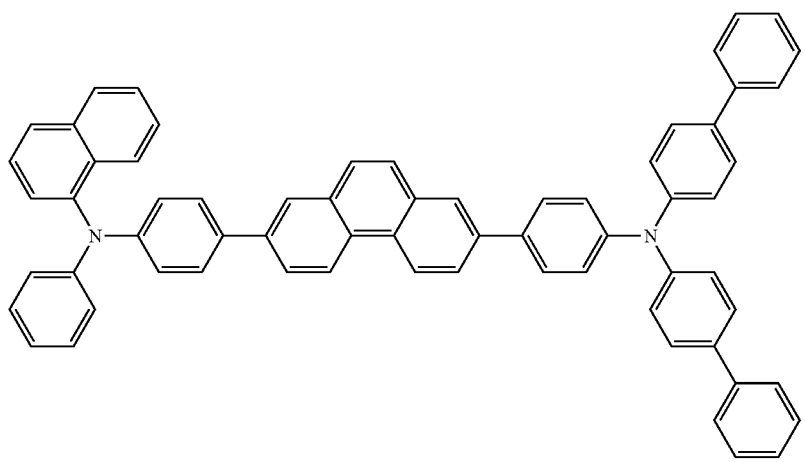
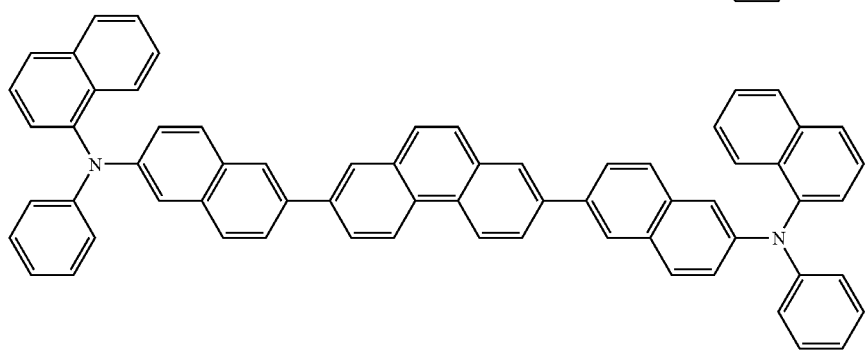
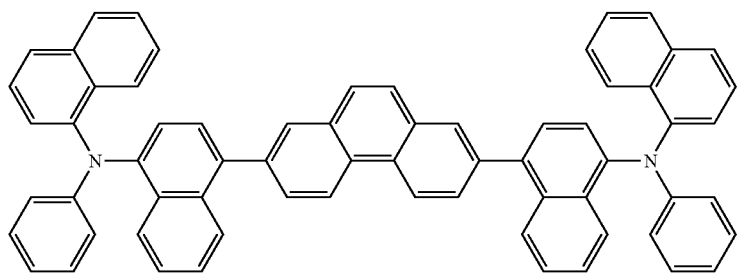
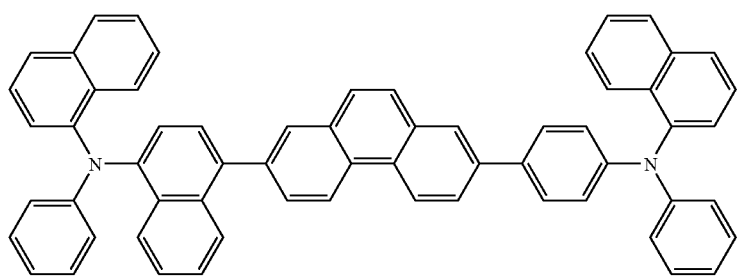

-continued
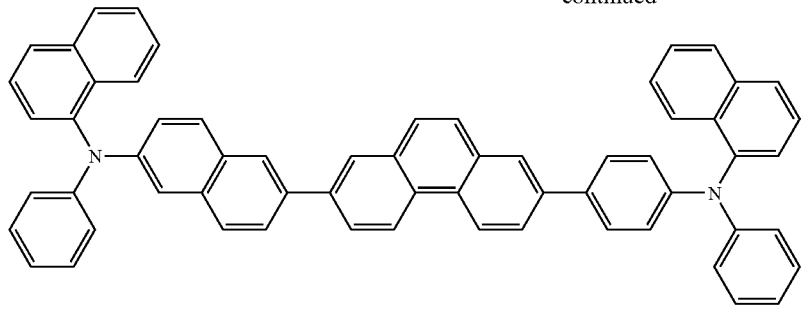
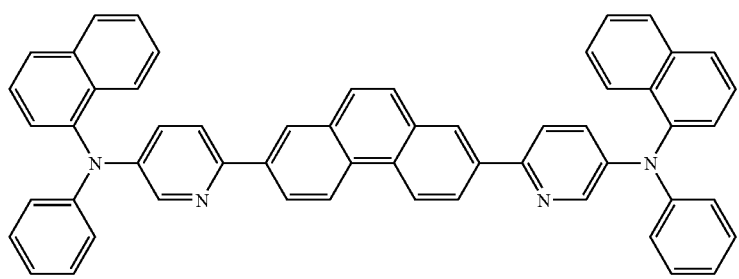
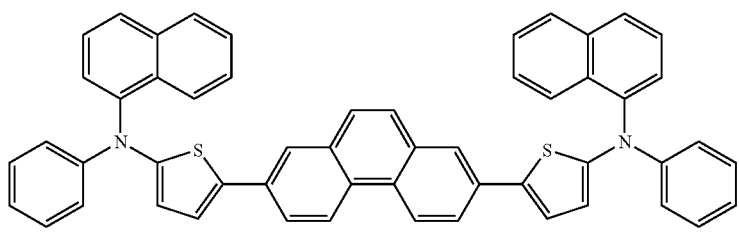
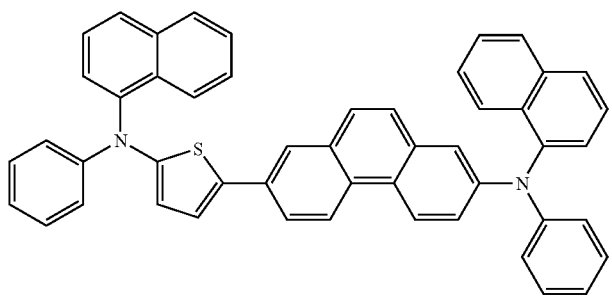
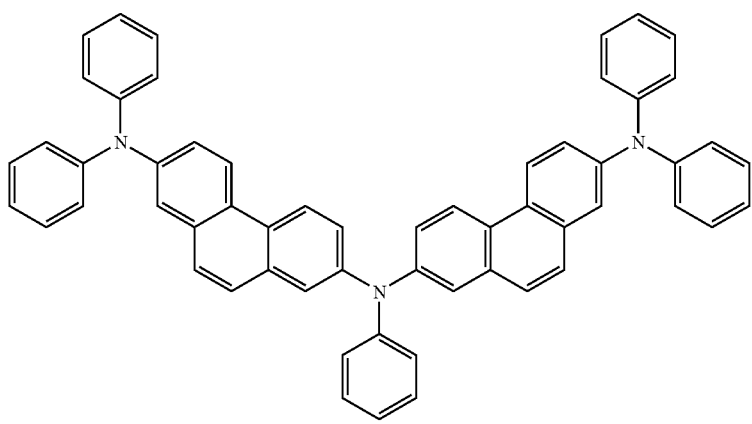

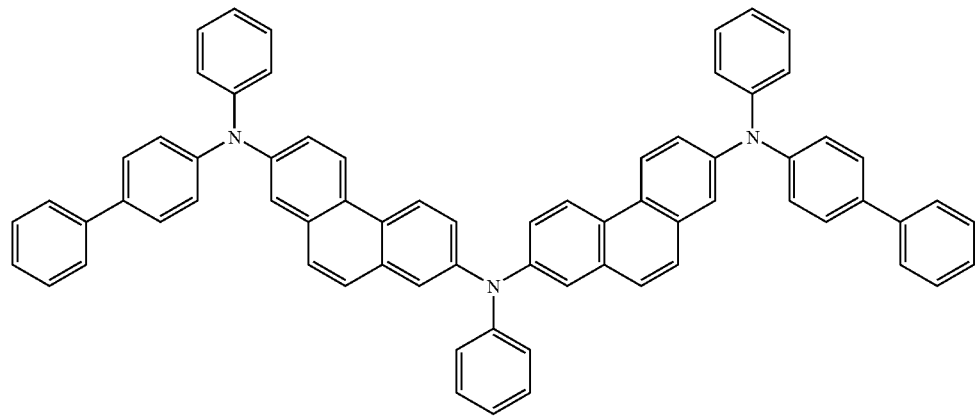
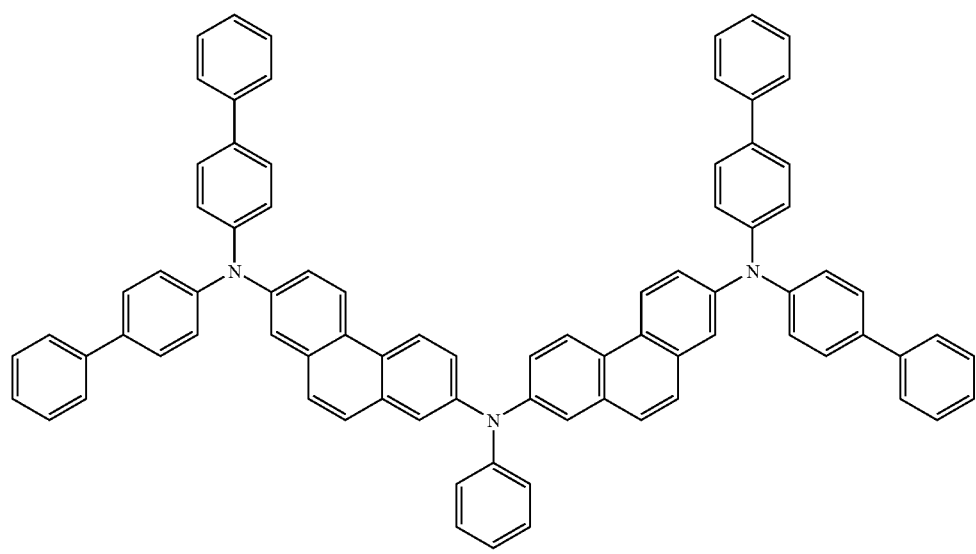
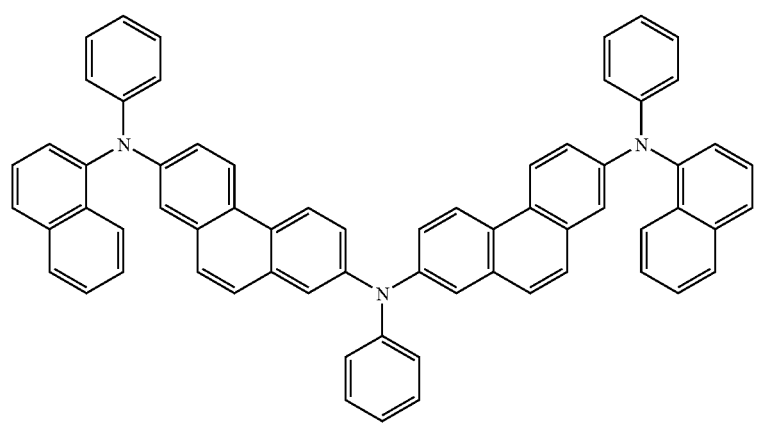

-continued
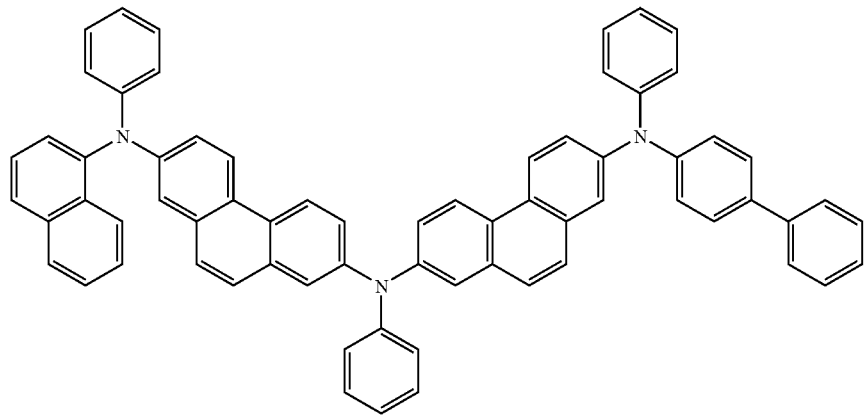
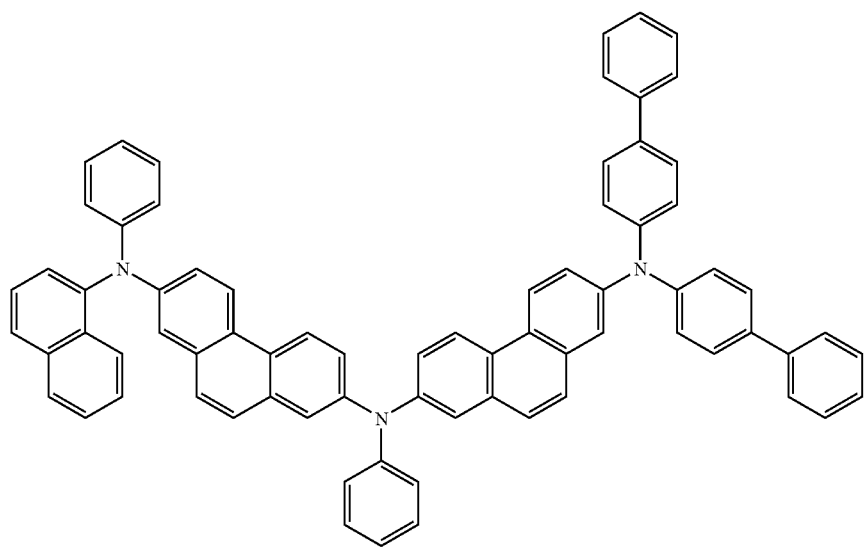
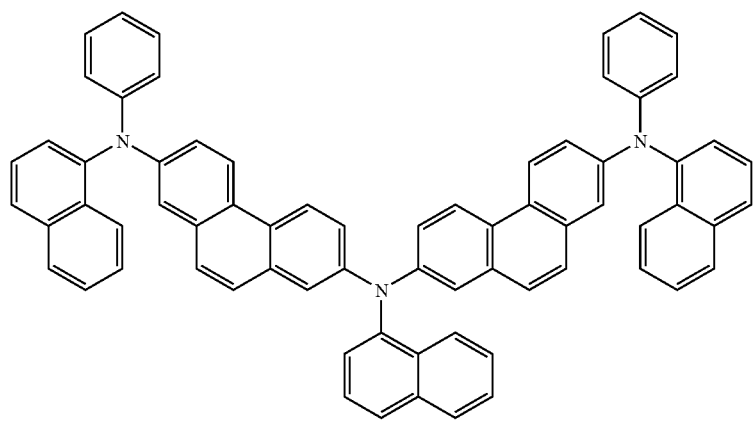

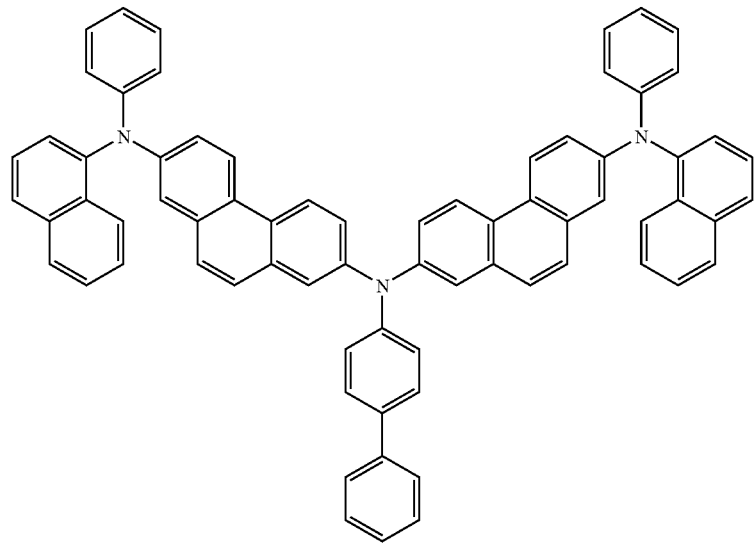
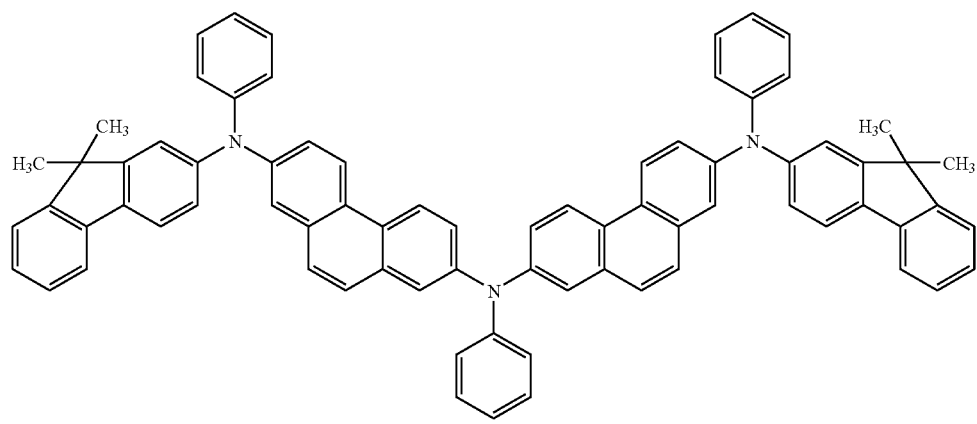
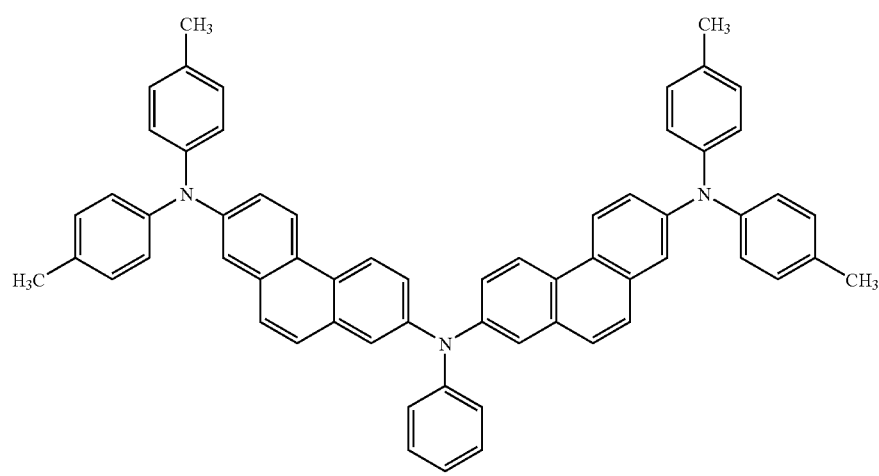

-continued
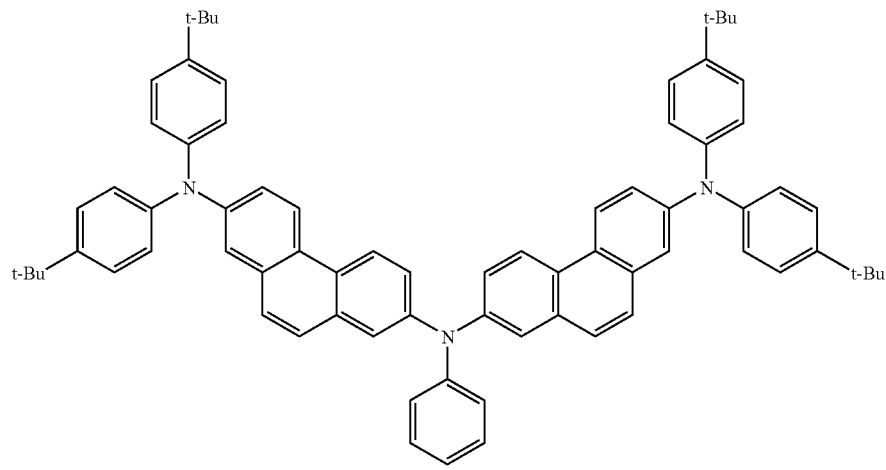
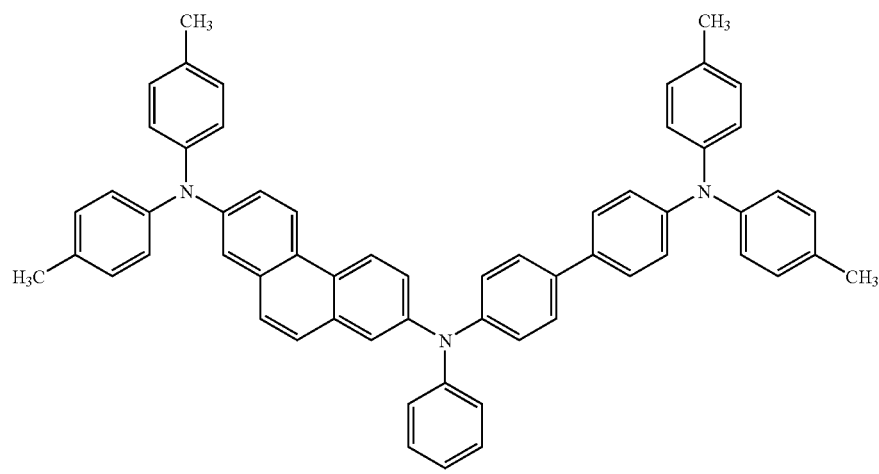
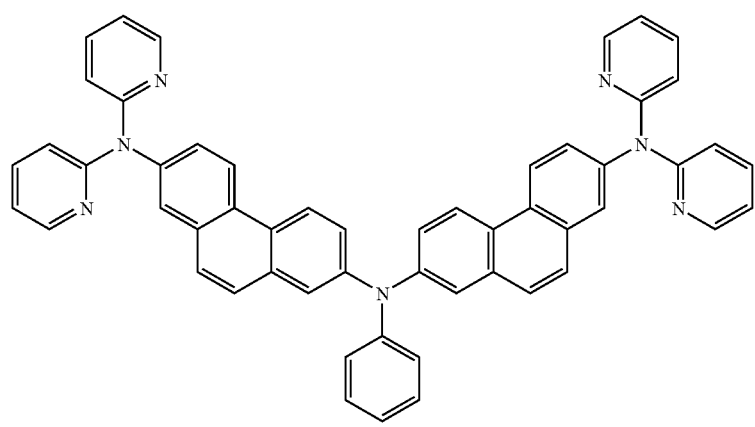

-continued
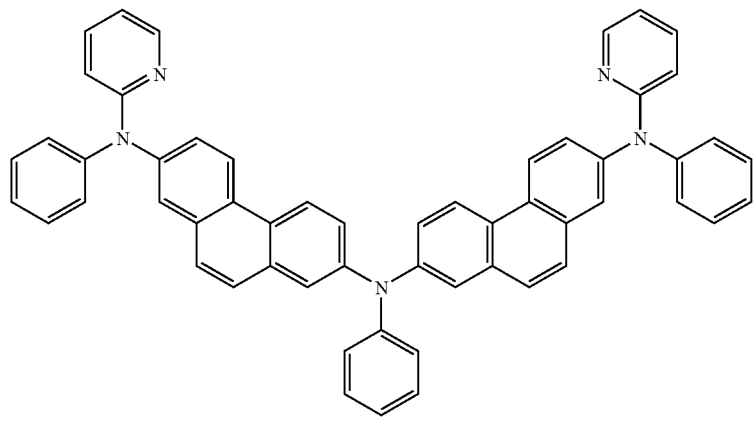
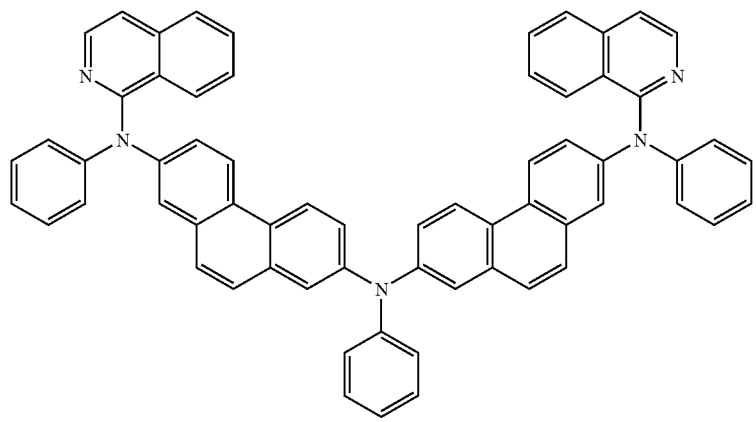
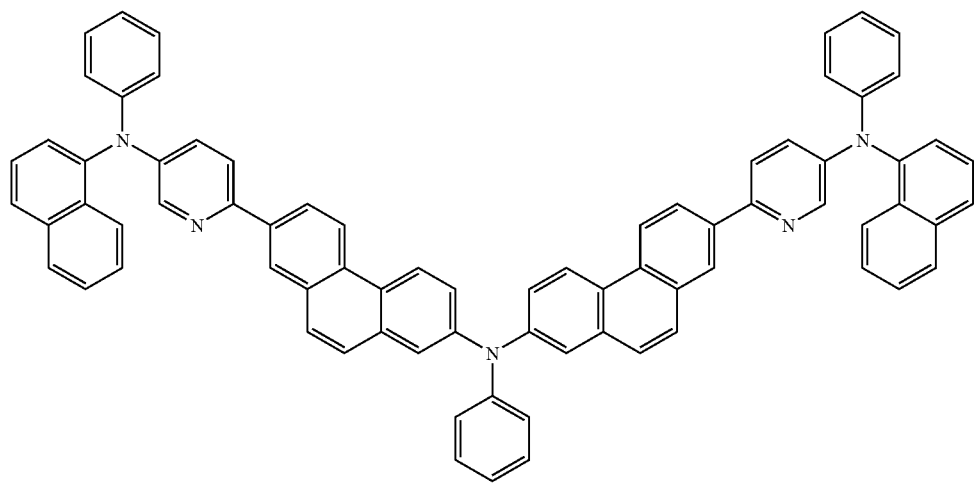

-continued
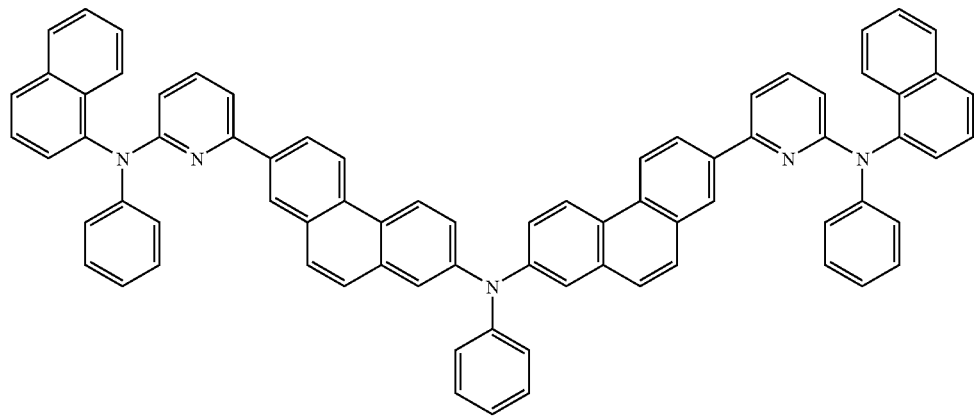
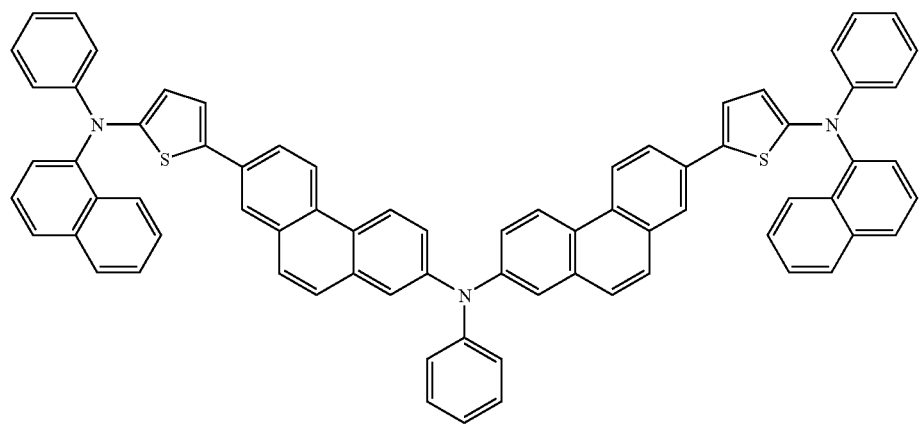
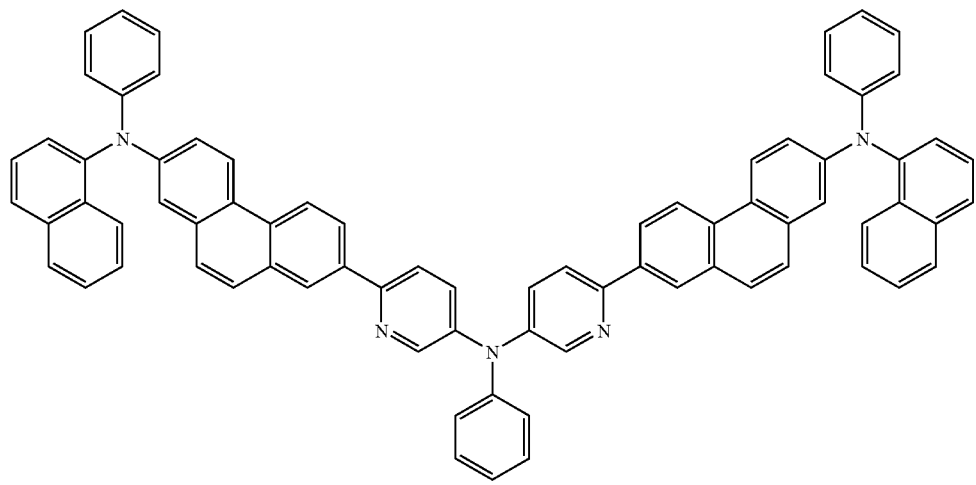

-continued
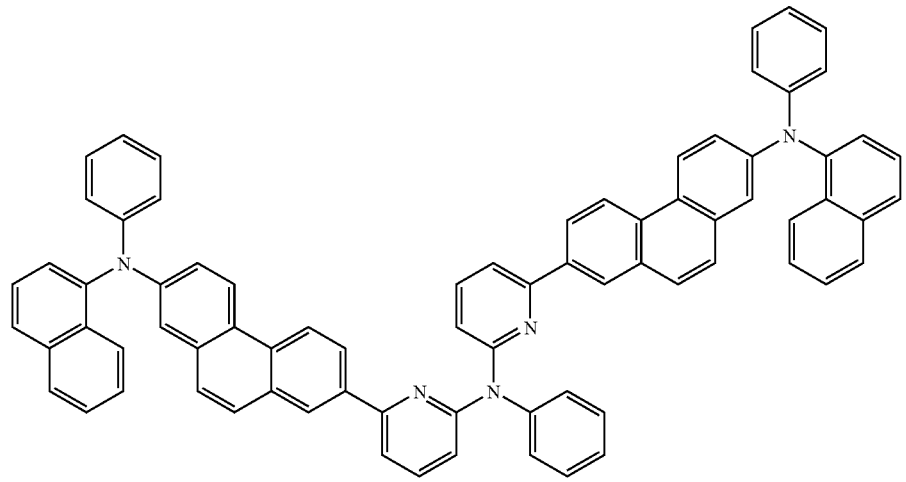
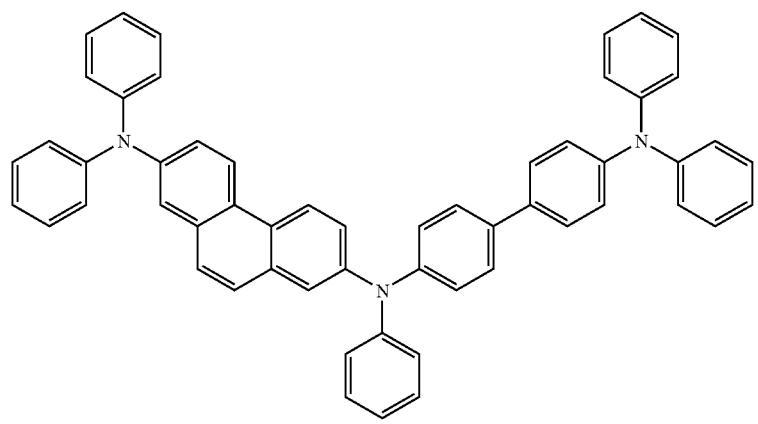
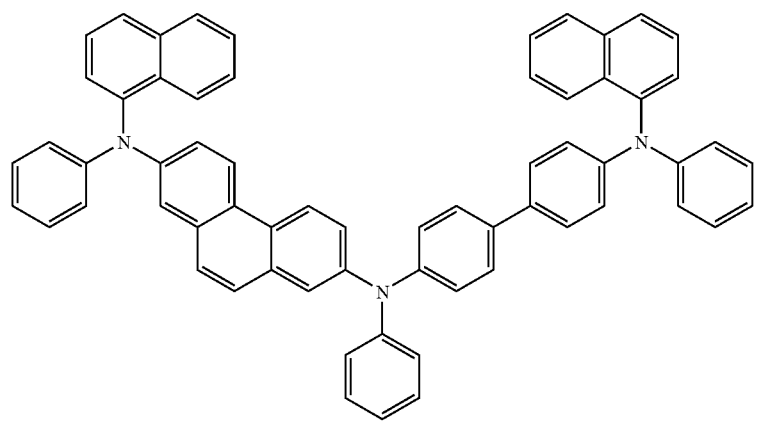

-continued
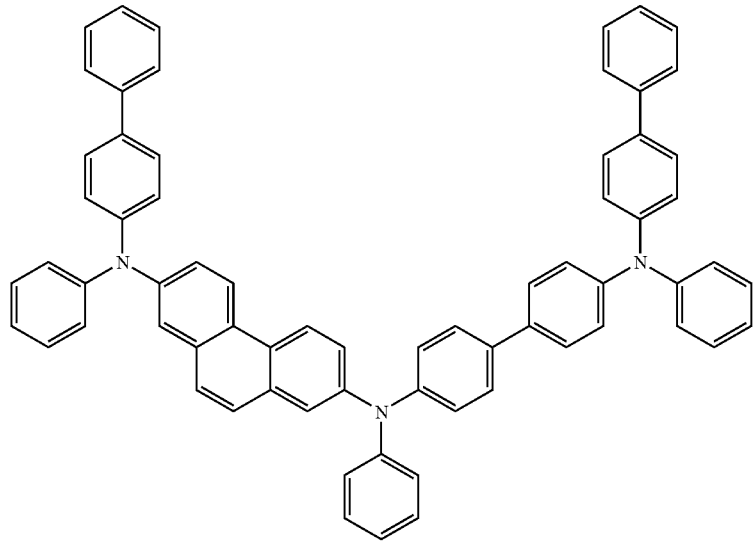
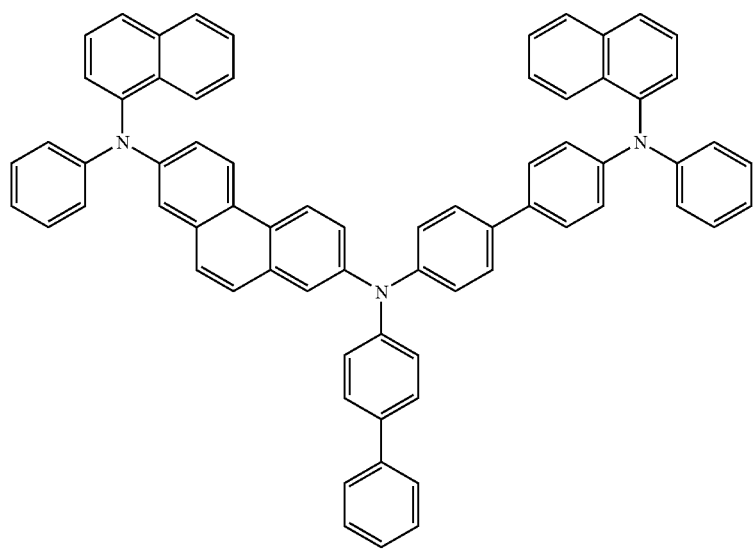
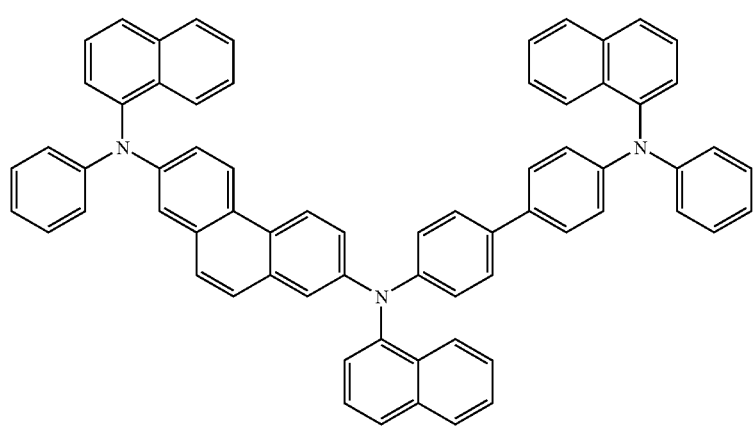

-continued
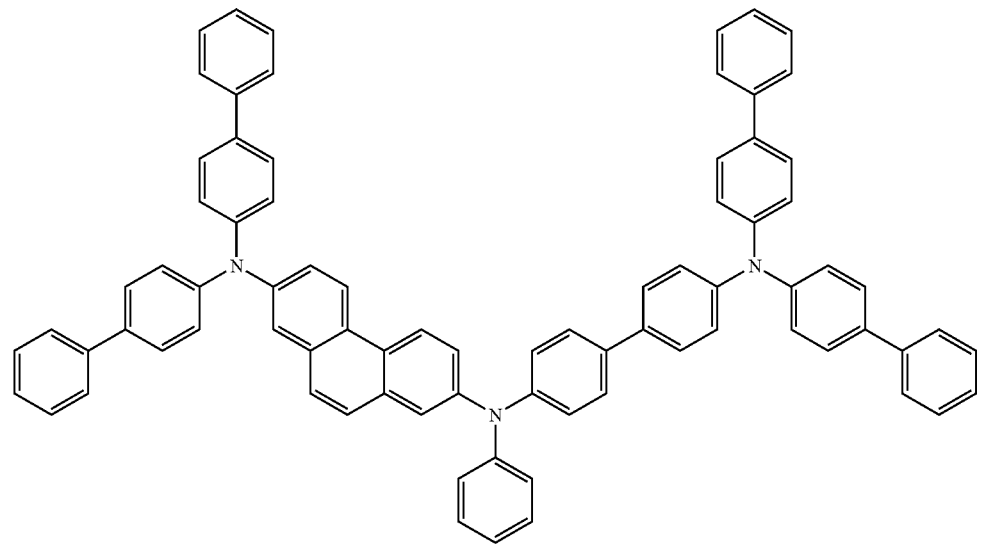
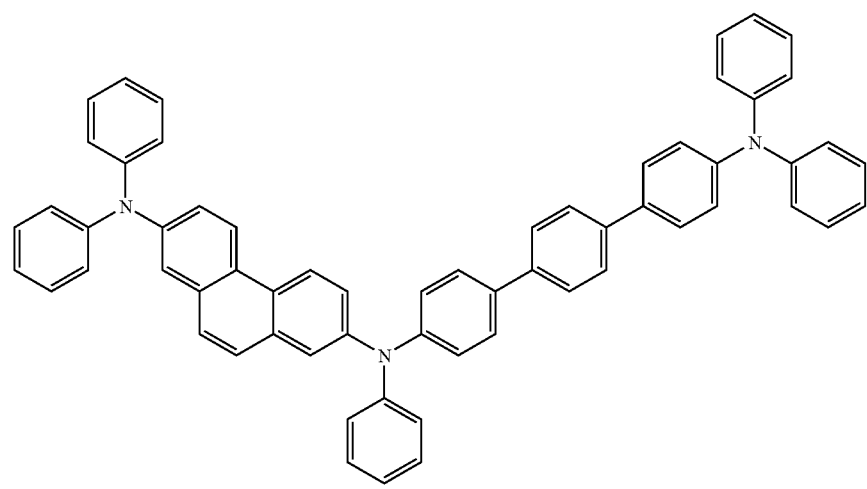
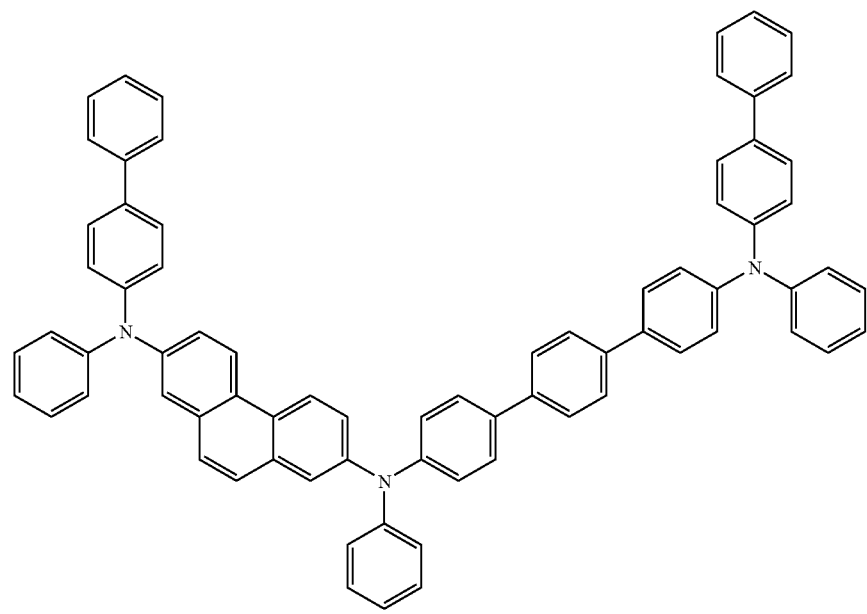

-continued
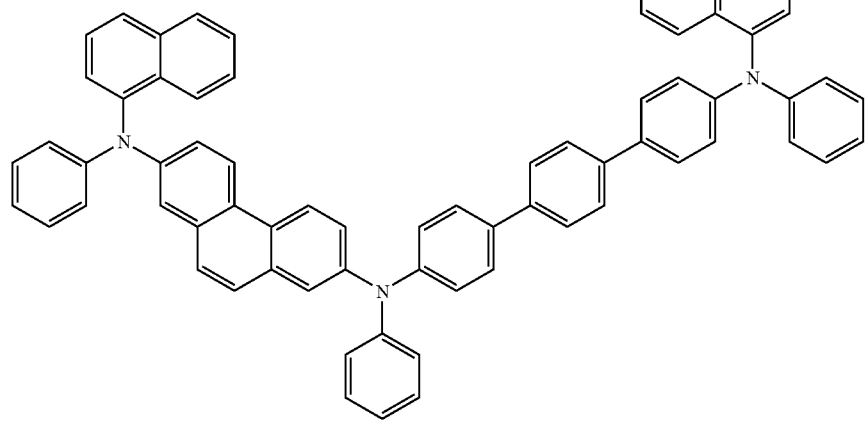
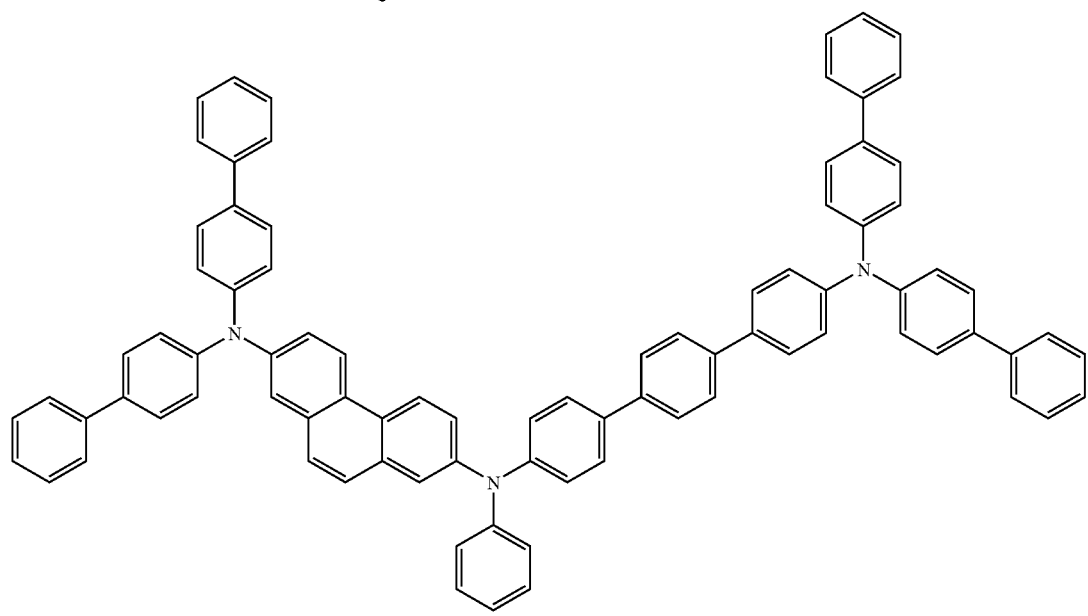
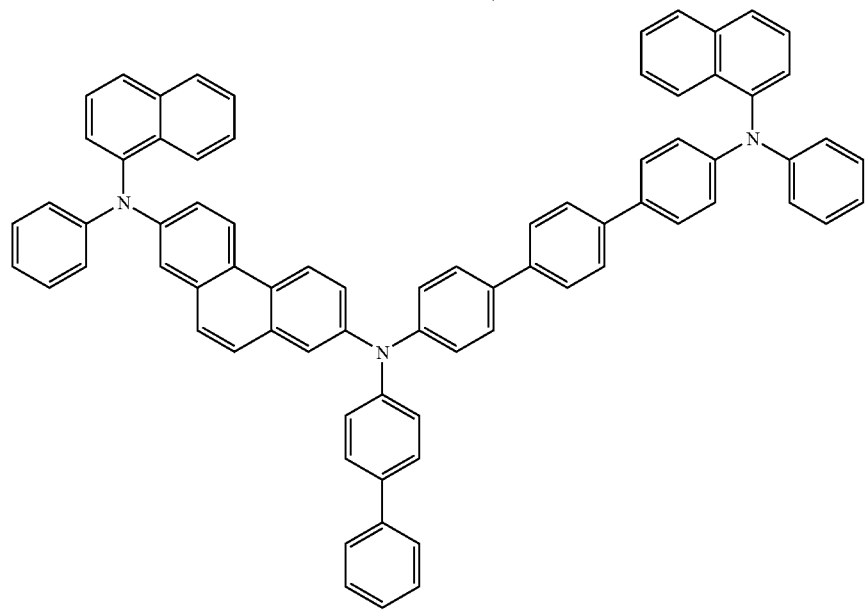

-continued
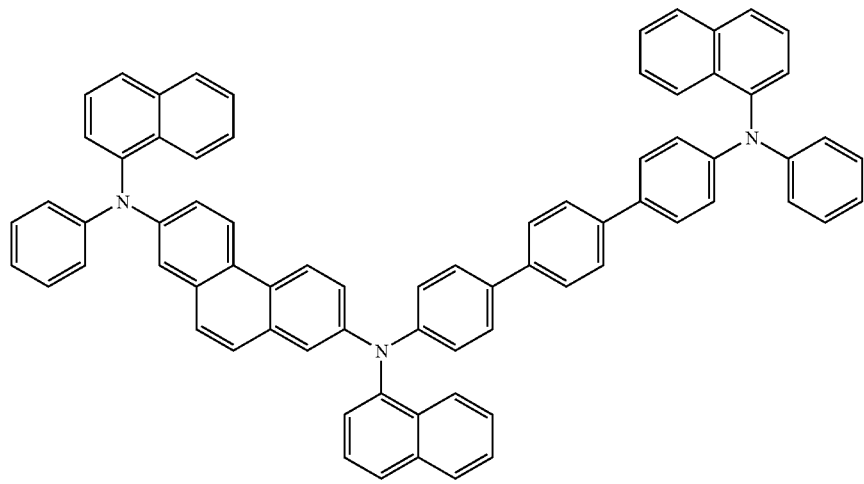
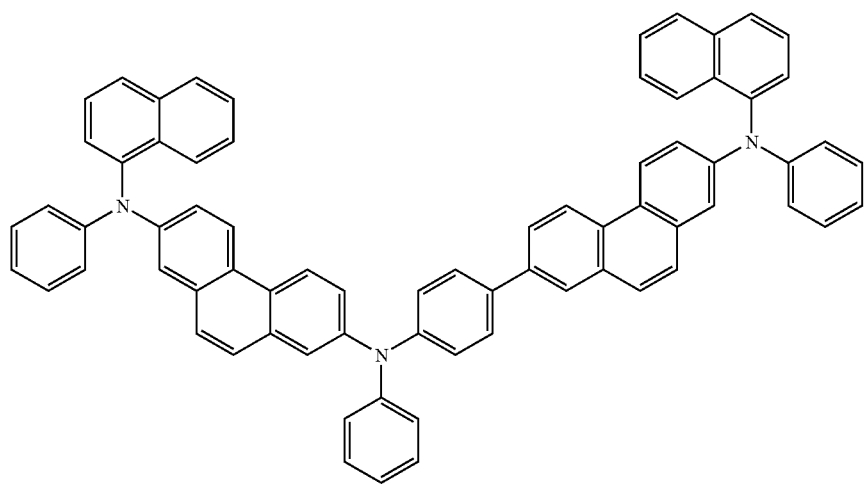
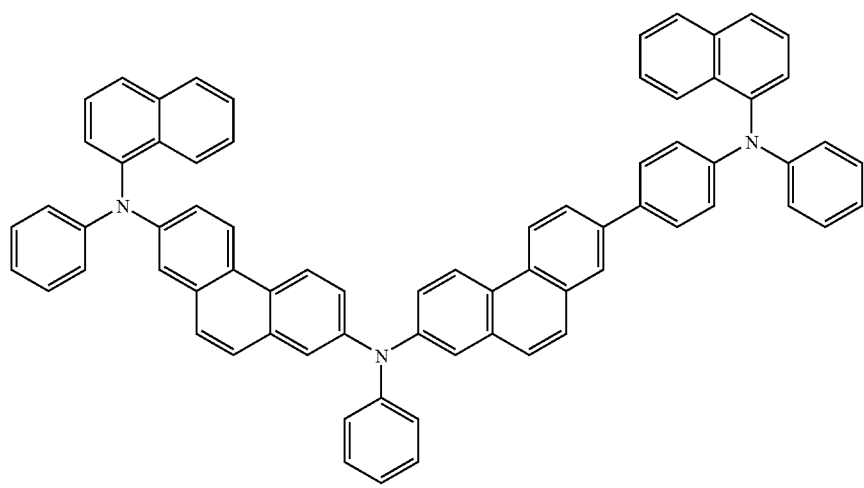

-continued
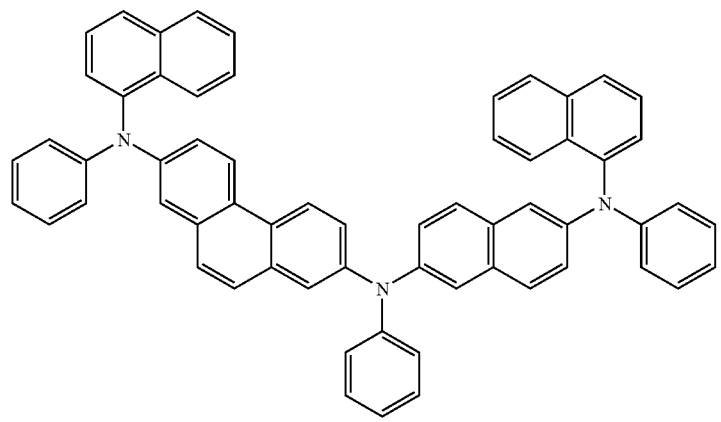

-continued
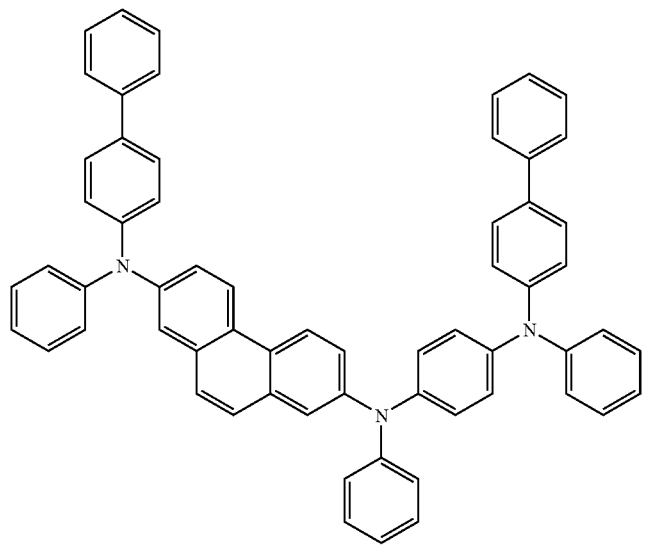
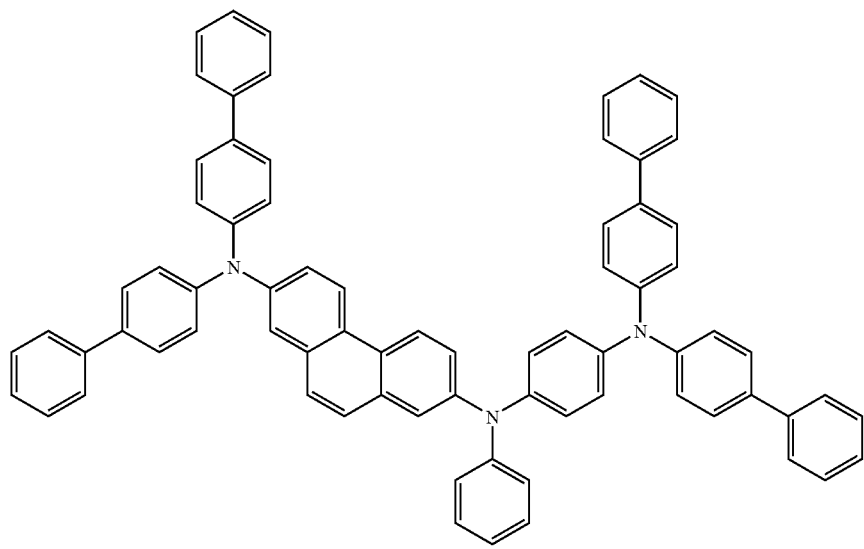
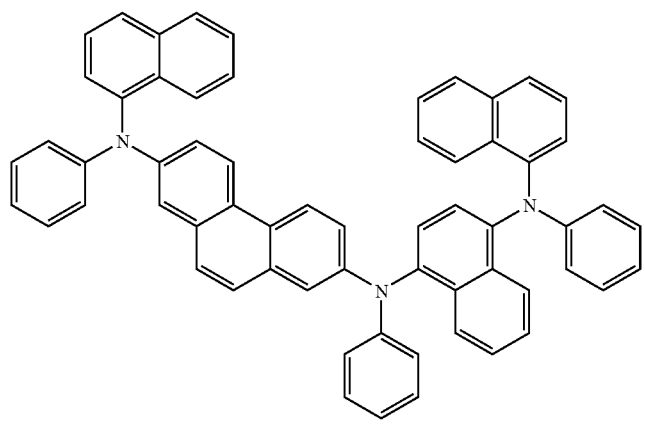

-continued
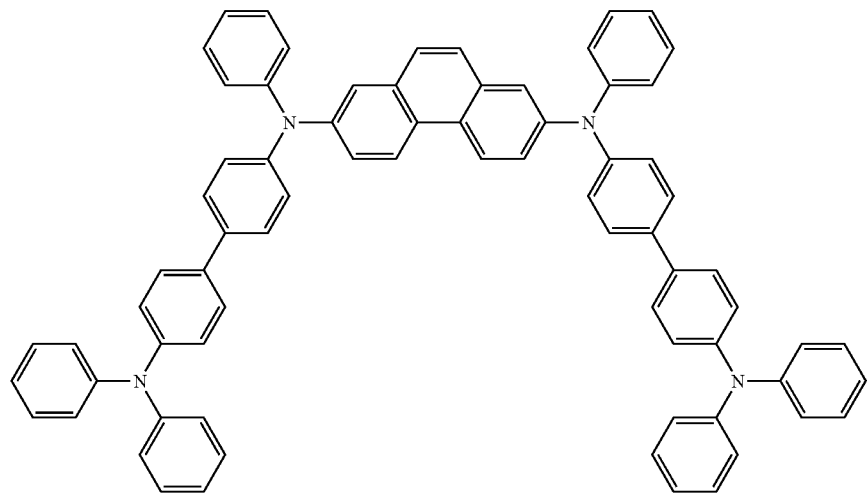
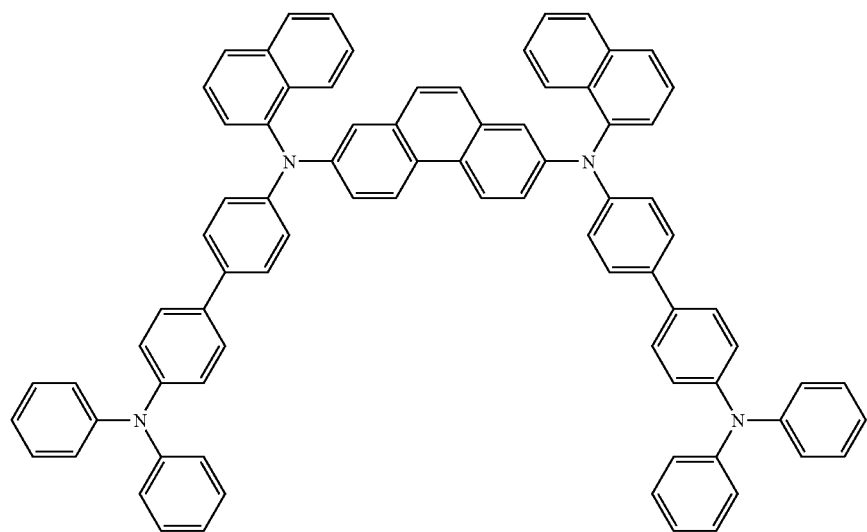
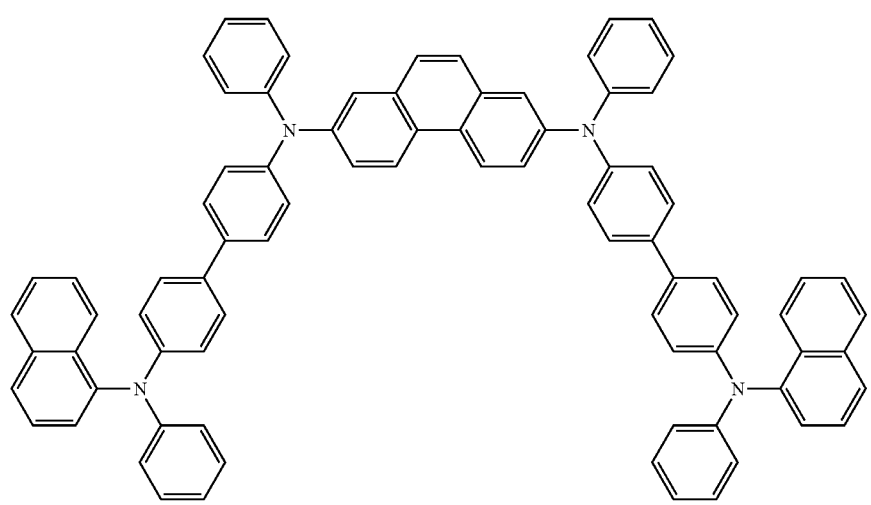

-continued
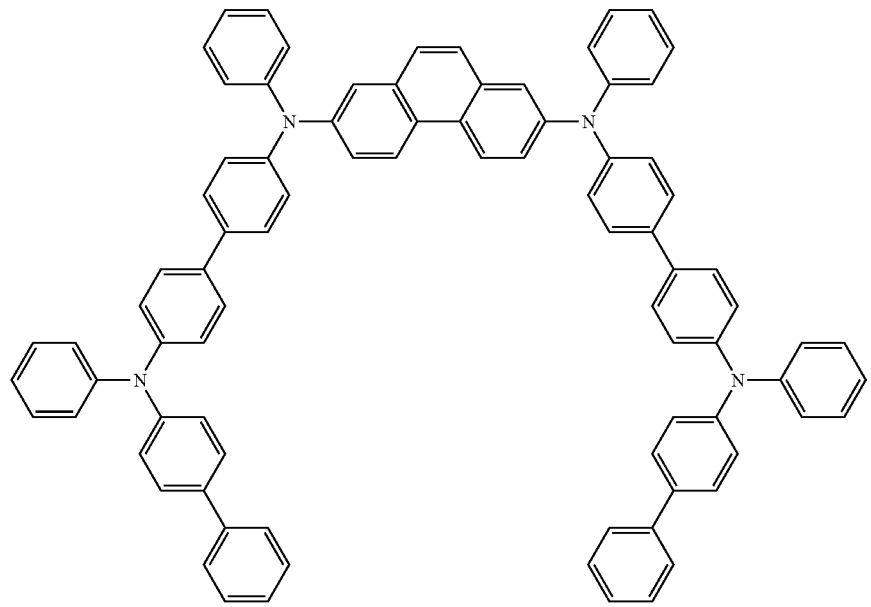
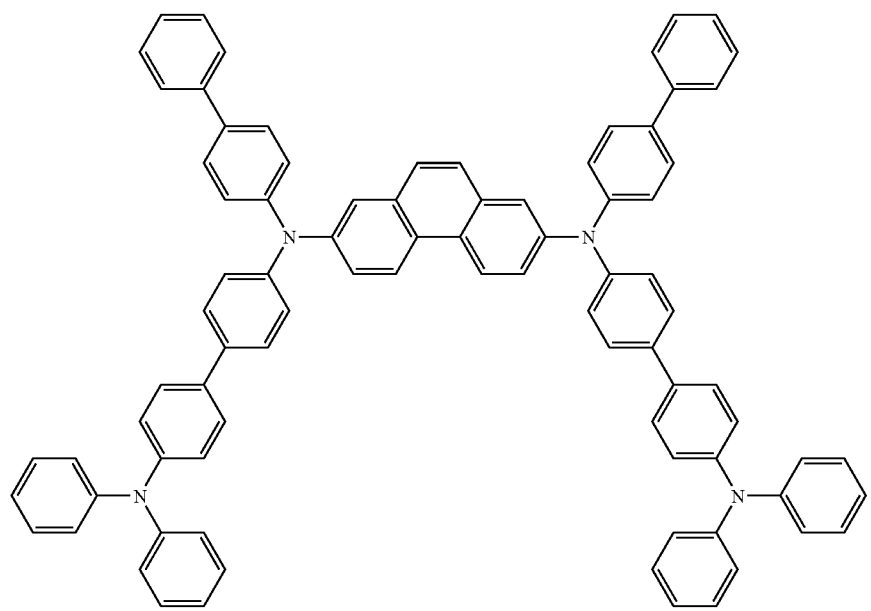

-continued
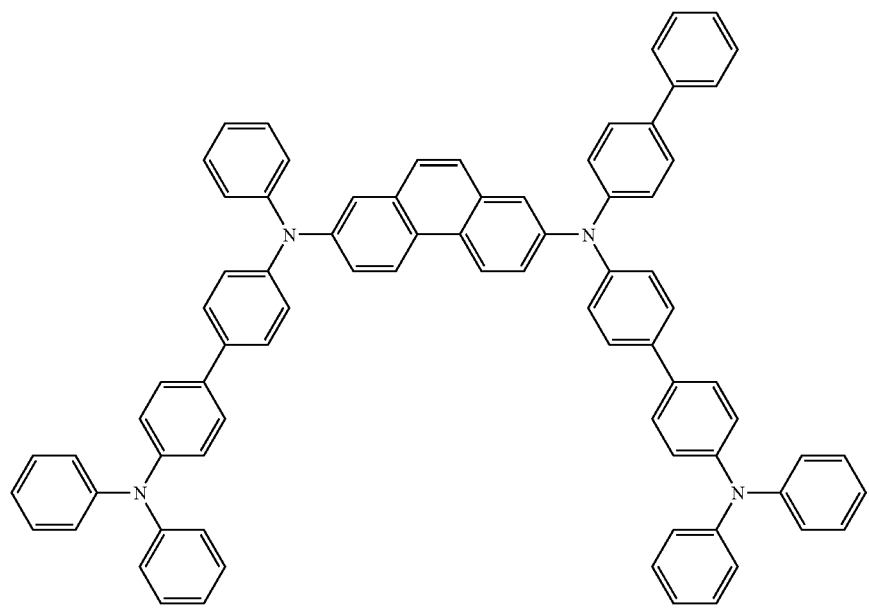
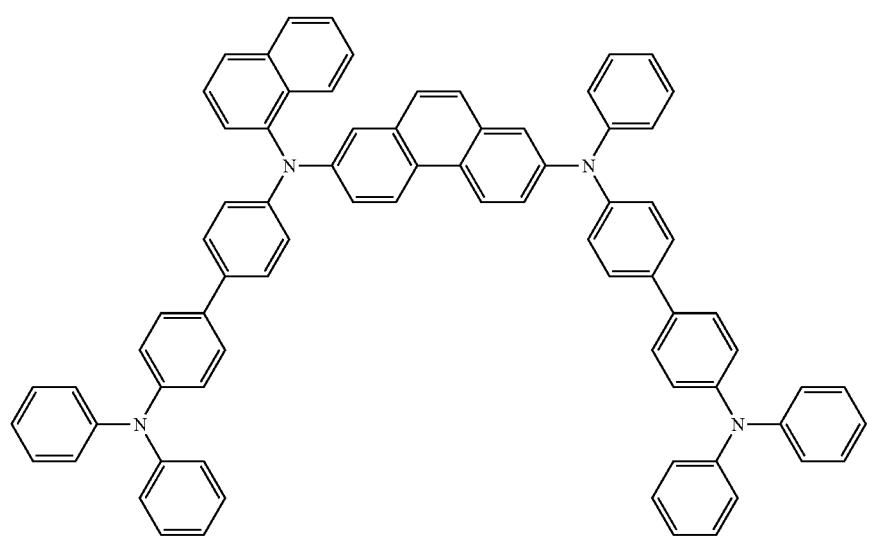

-continued
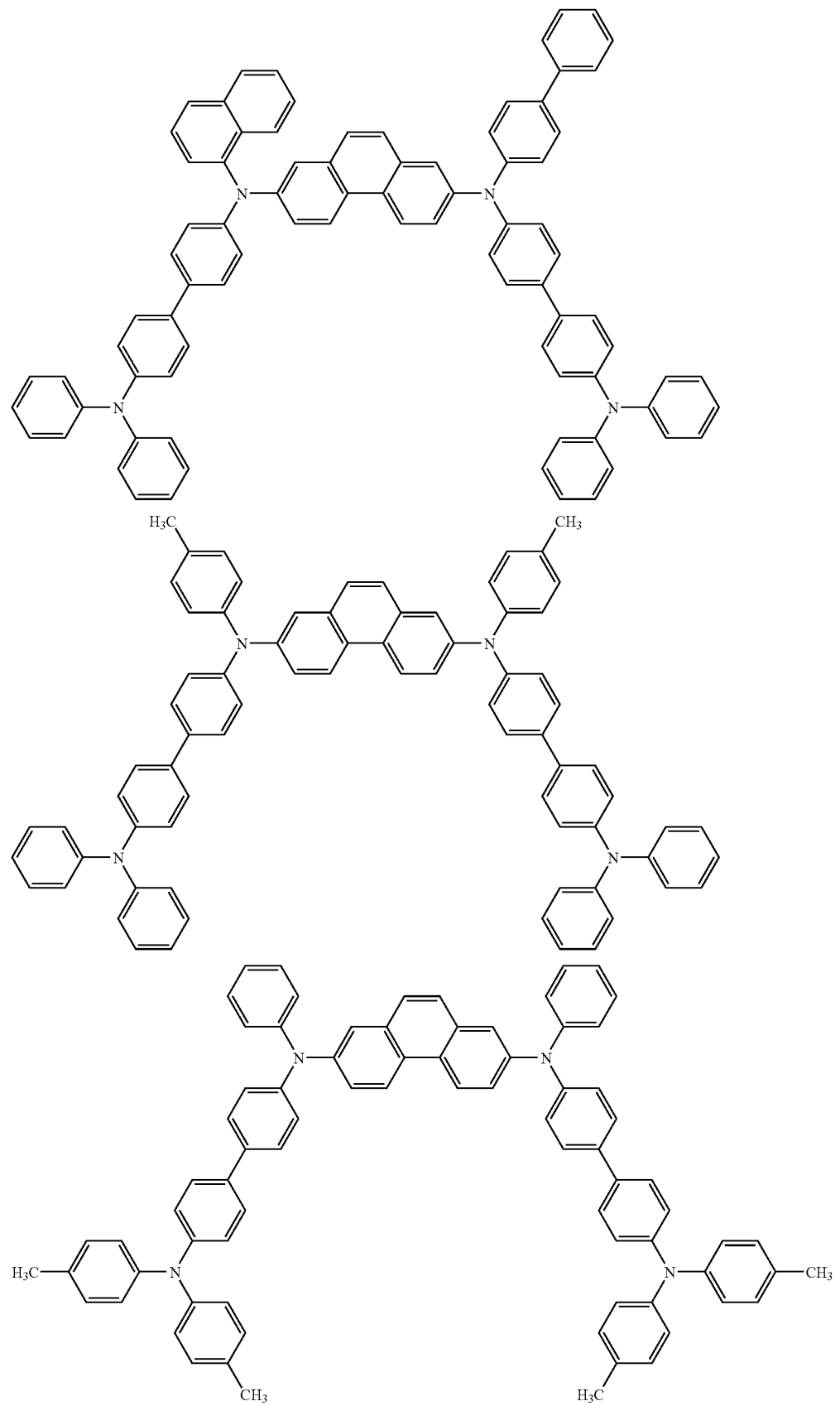

-continued
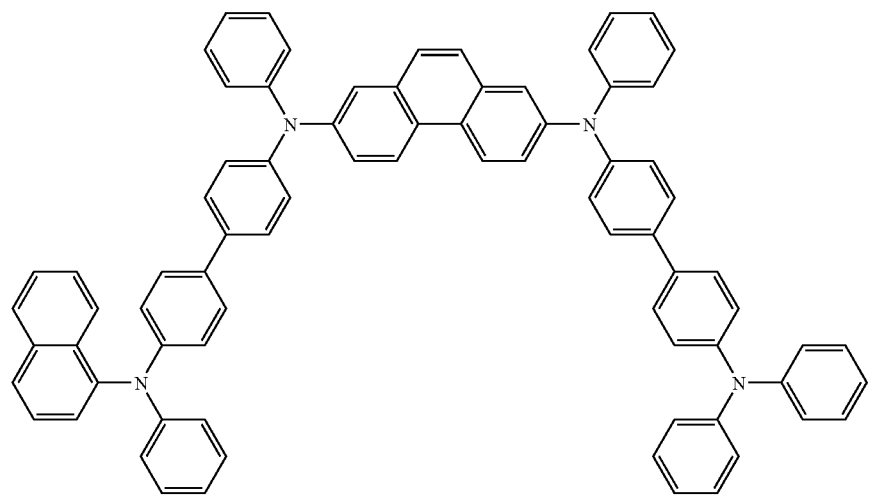
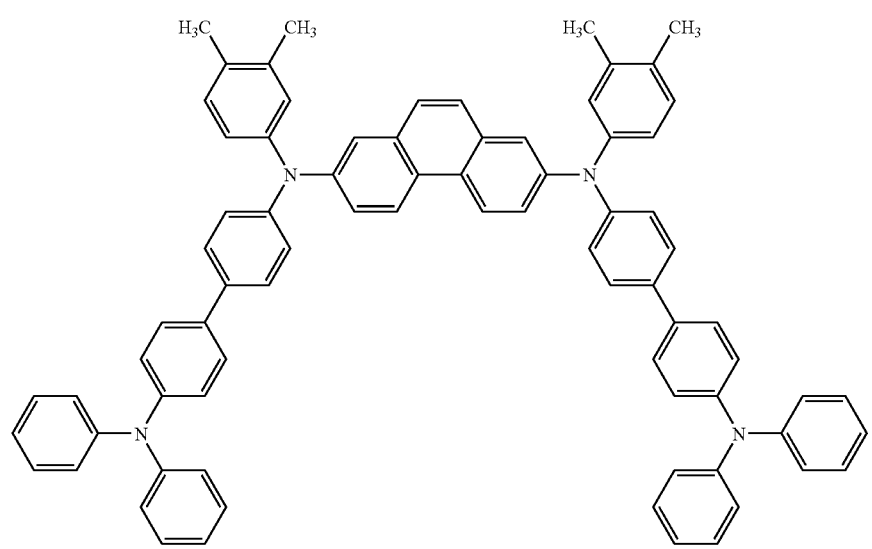
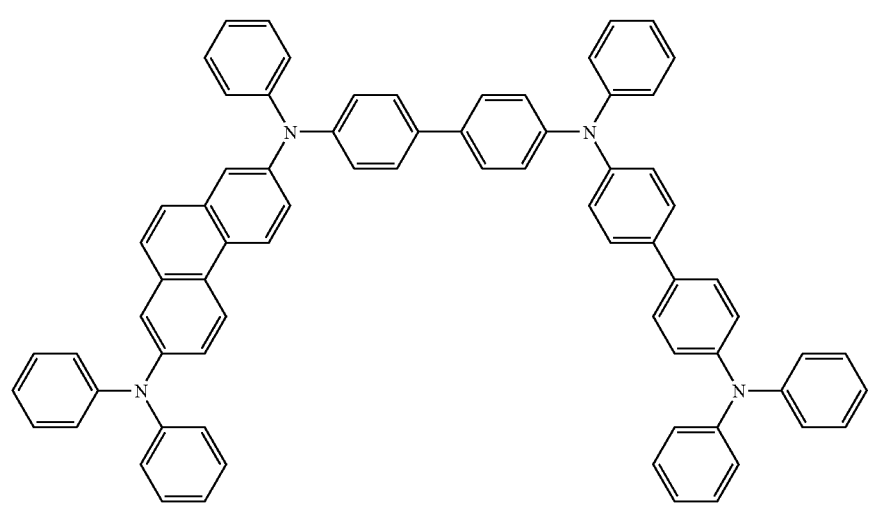

-continued
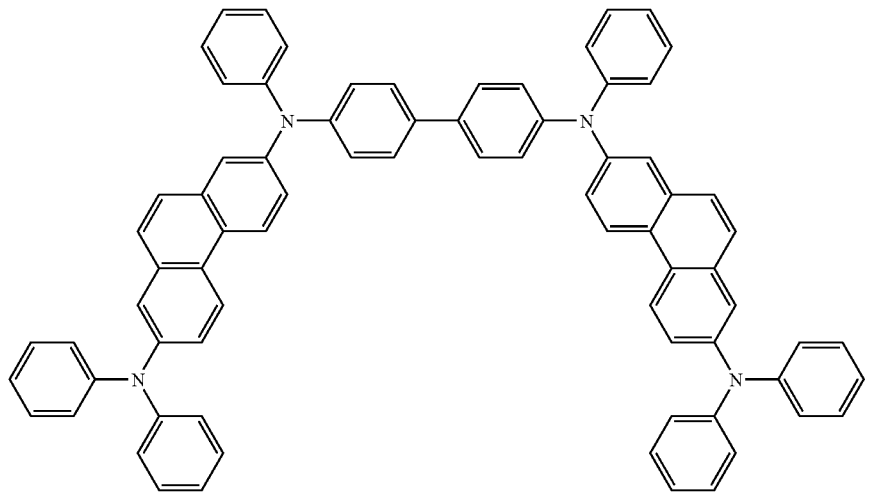
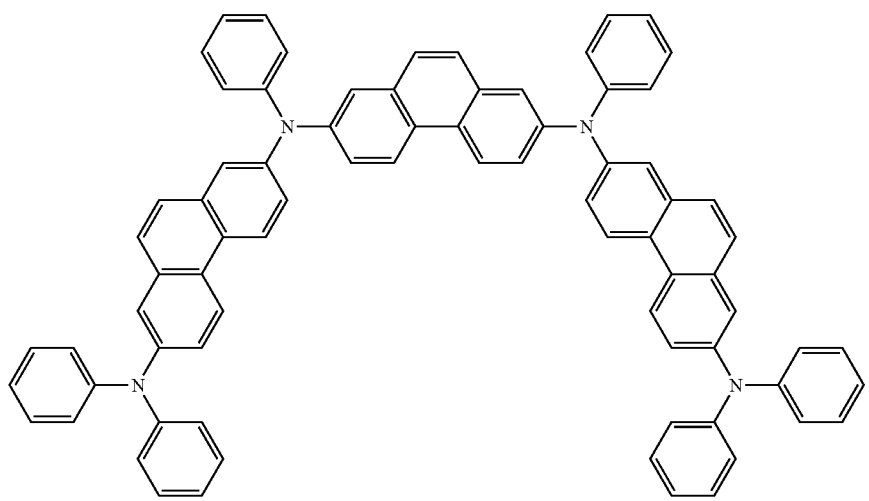
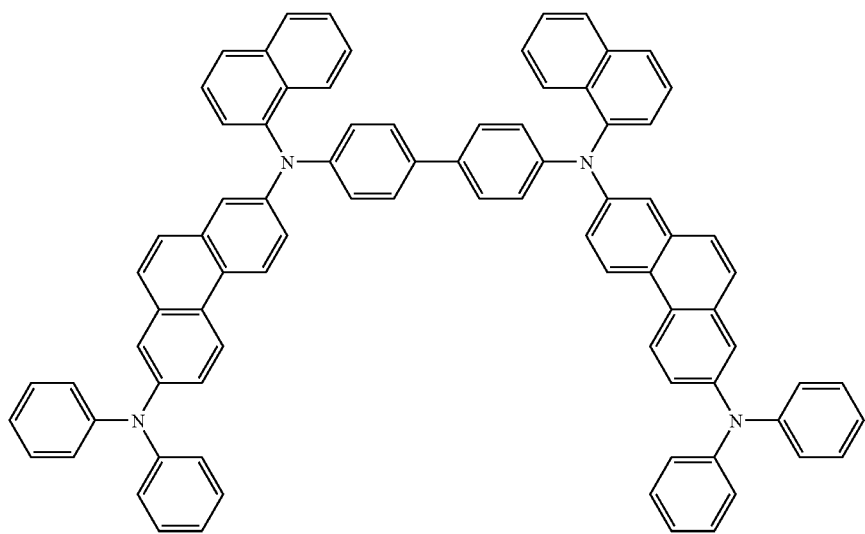

-continued
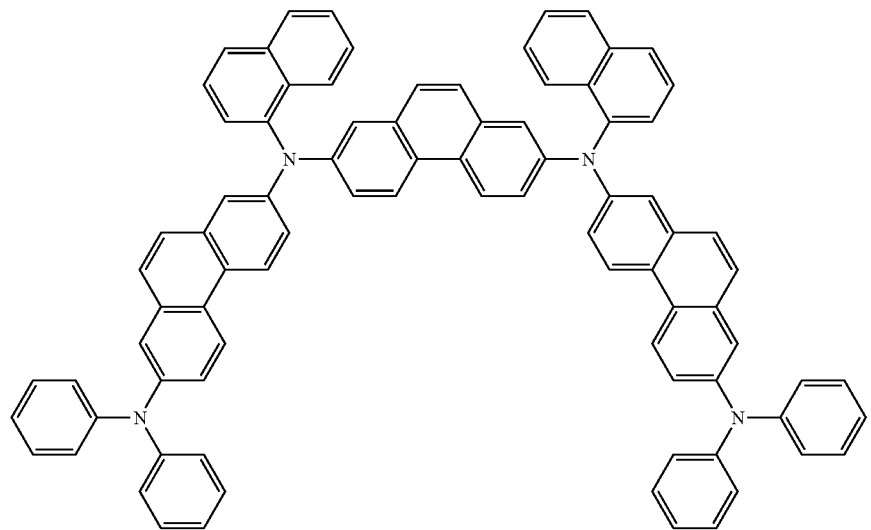
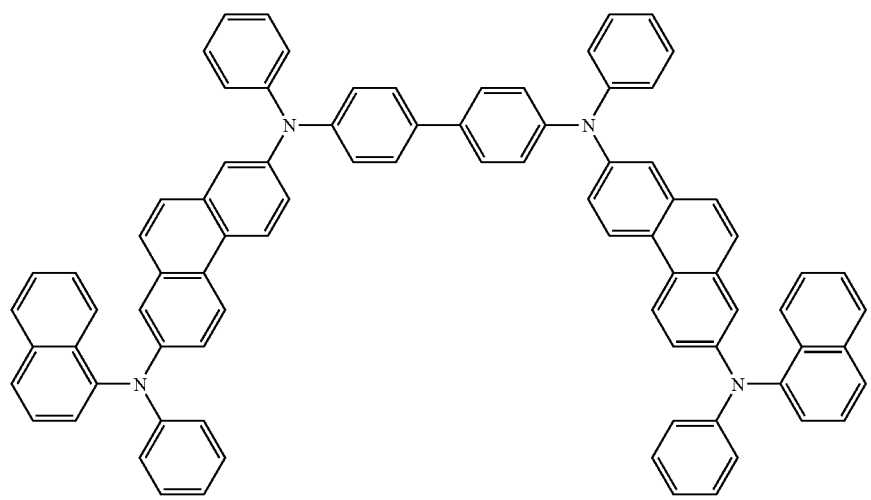
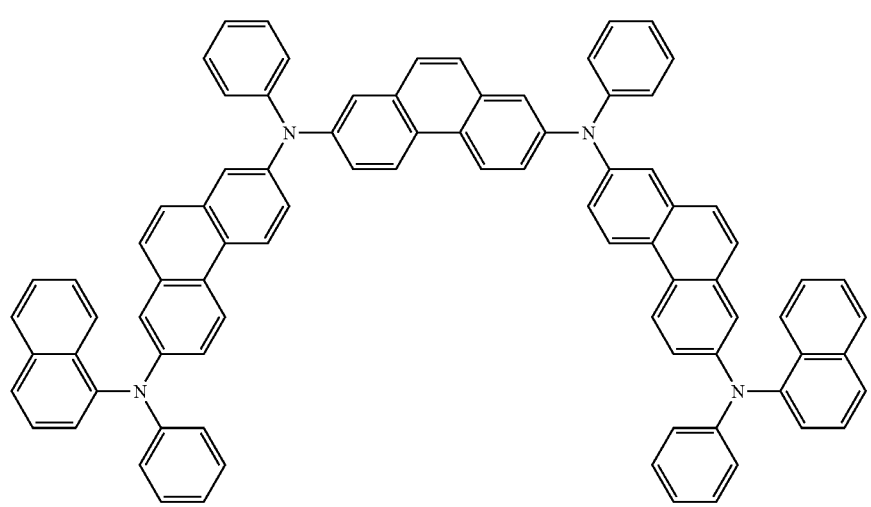

-continued
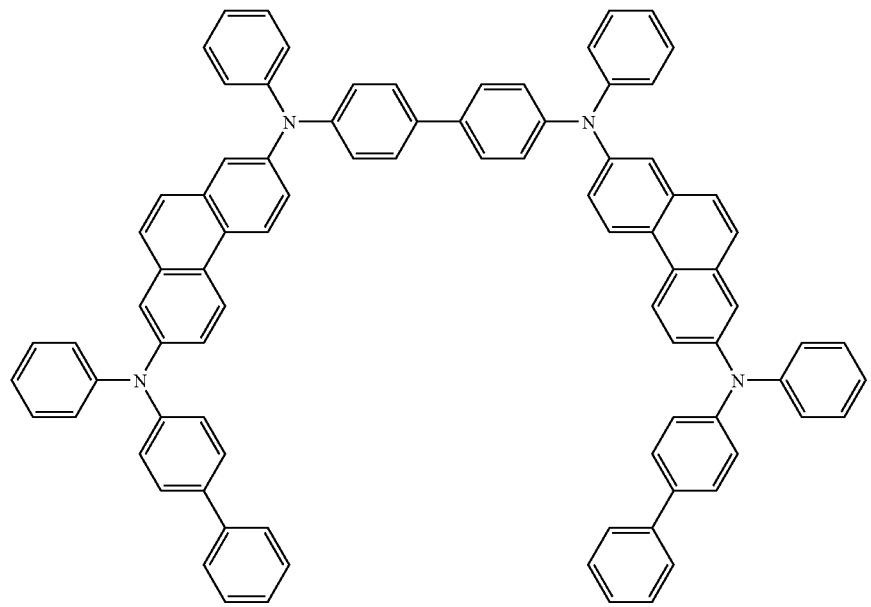
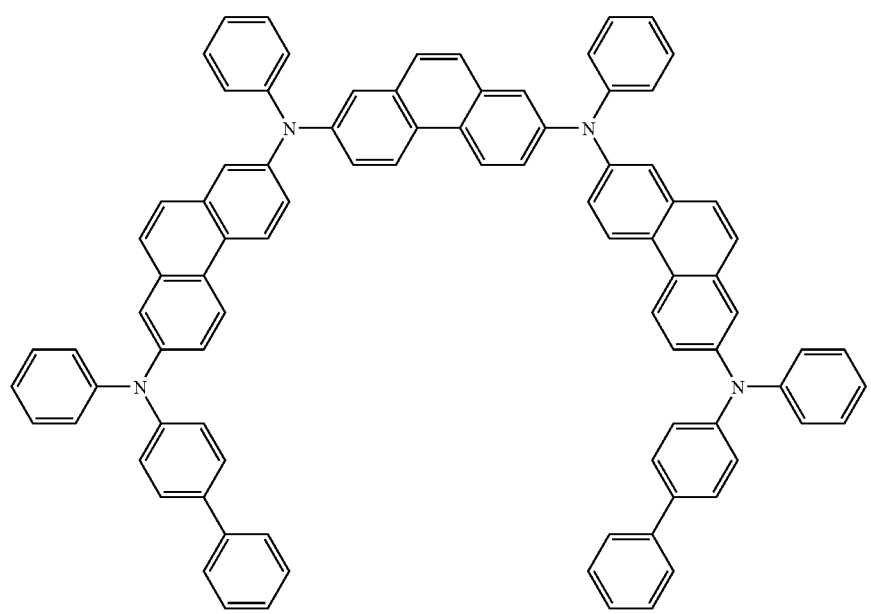

-continued
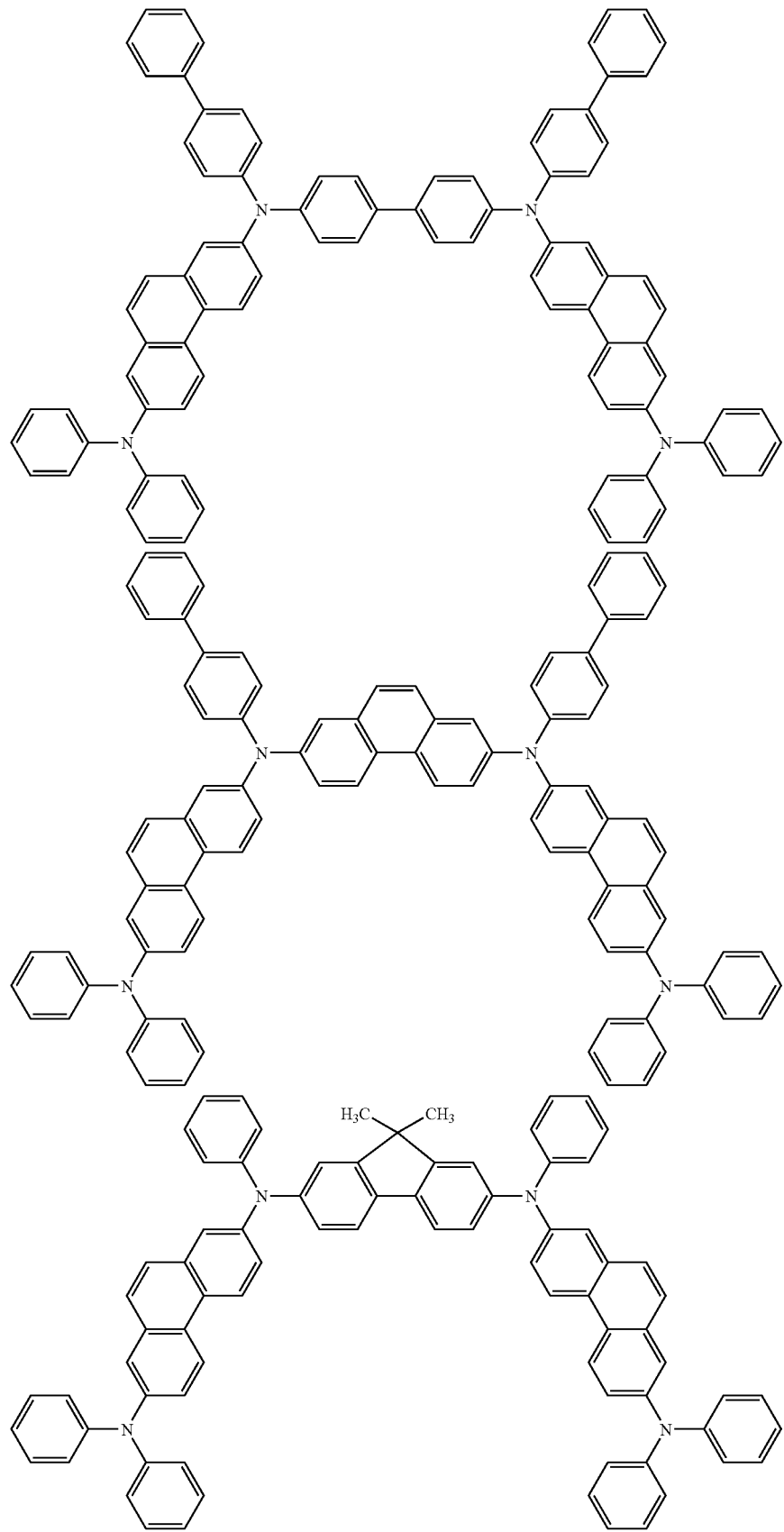

-continued
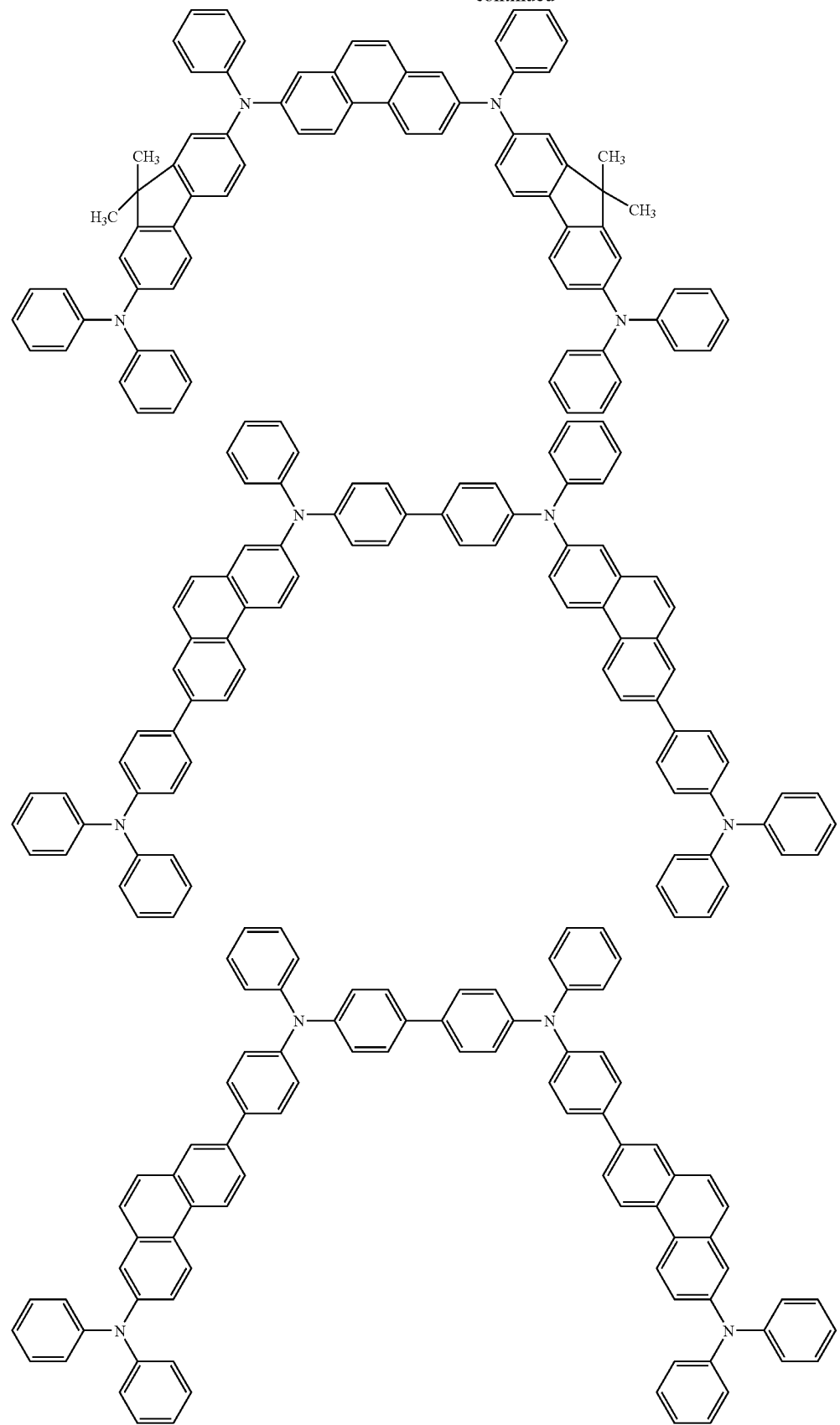

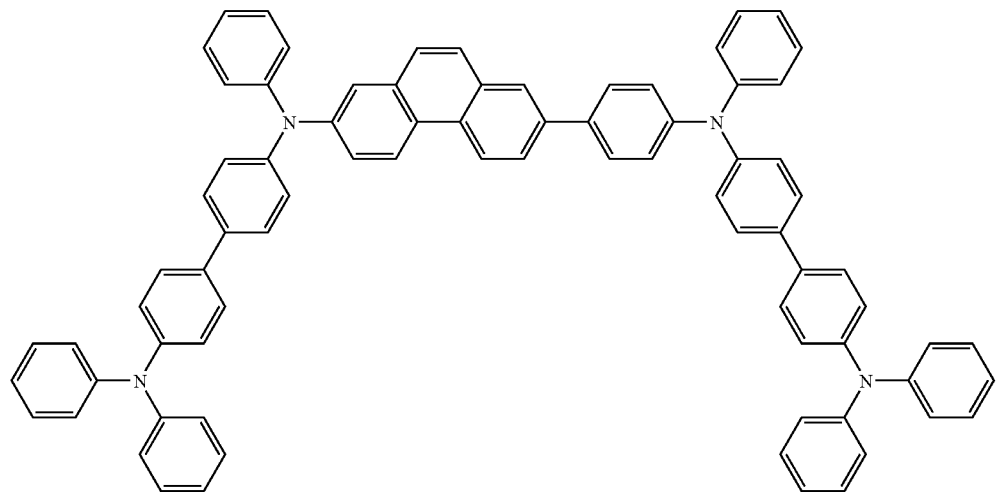
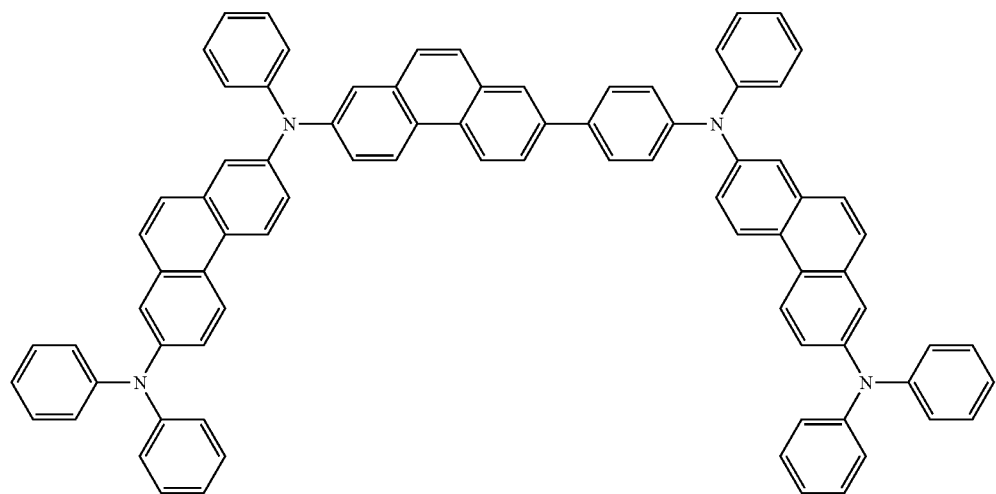
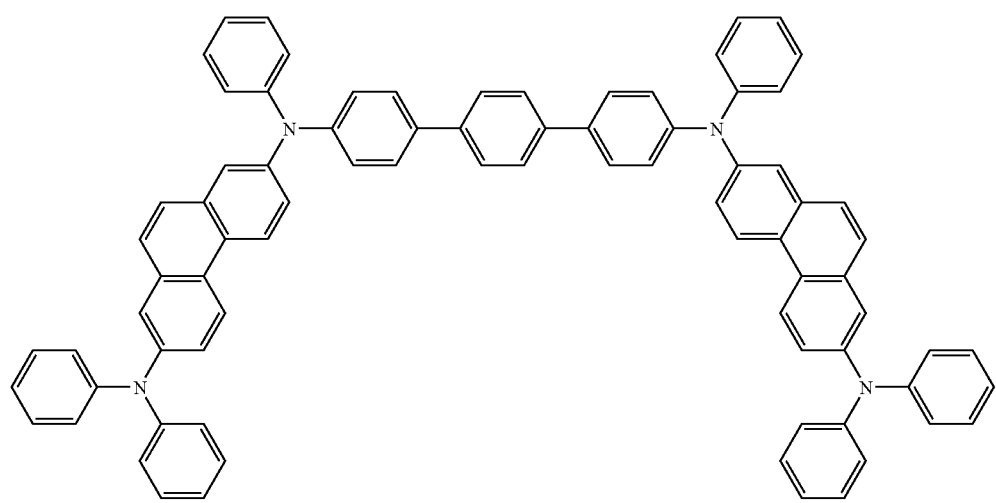

-continued
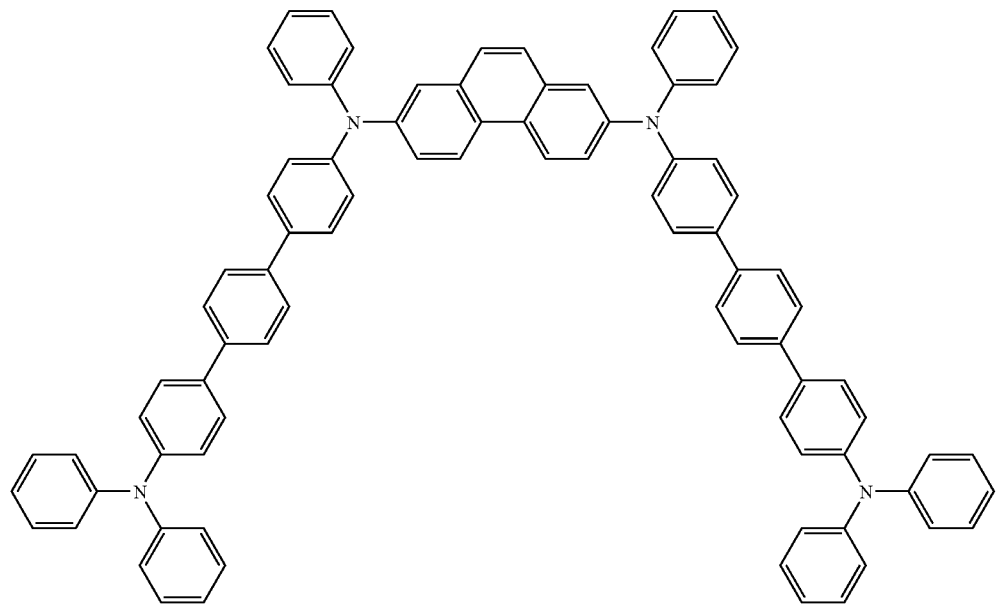
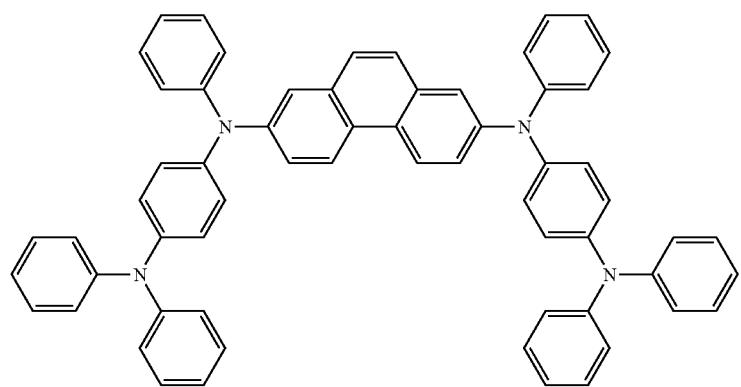
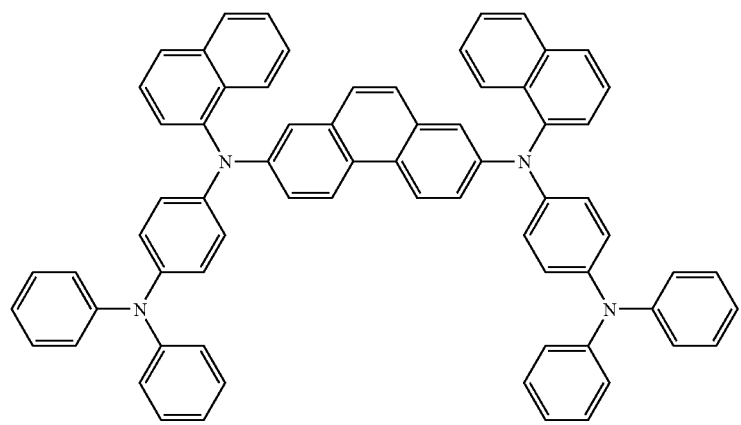

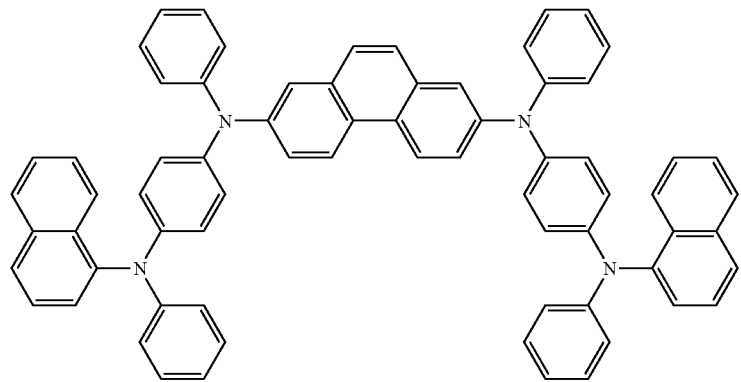
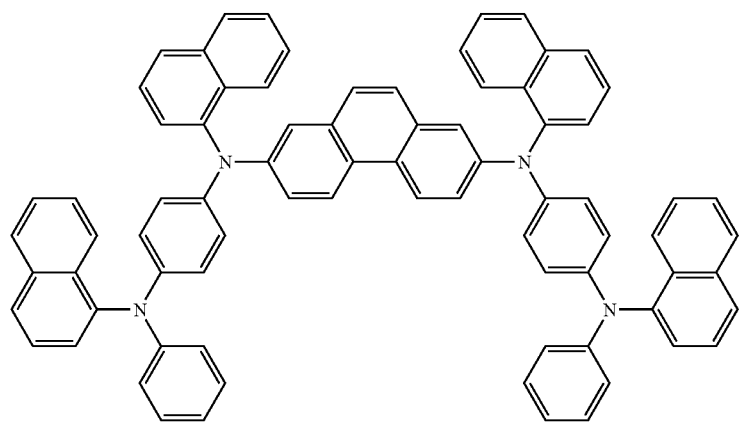
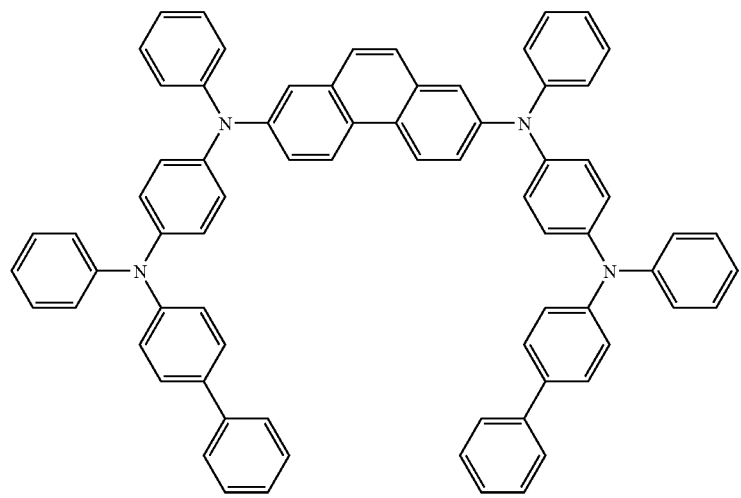

-continued

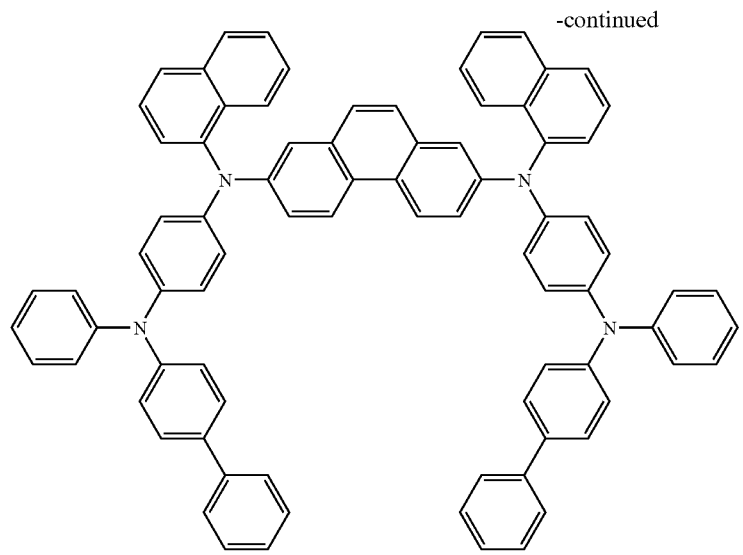

The present invention provides a material for an organic EL device comprising the aromatic amine derivative represented by any one of the above general formulae (1) to (3), together with a material for an organic EL device represented by a following general formula (5):

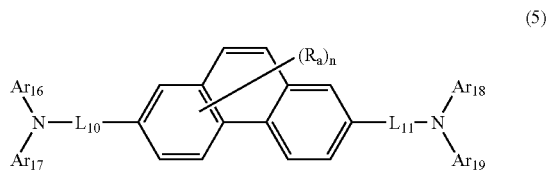
(5)

In the general formula (5), $Ar_{16}$ to $Ar_{19}$ each independently represents a substituted or unsubstituted aryl group having 6 to 30 ring carbon atoms or a substituted or unsubstituted heteroaryl group having 5 to 30 ring carbon atoms; $L_{10}$ and $L_{11}$ each independently represents a single bond, a substituted or unsubstituted arylene group having 6 to 30 ring carbon atoms or a substituted or unsubstituted heteroarylene group having 5 to 30 ring carbon atoms; $R_a$ represents a substituent and when $R_a$ exists two or more, they may bond each other to form a ring; and n represents an integer of 0 to 8. Specific examples of $Ar_{16}$ to $Ar_{19}$, $L_{10}$, $L_{11}$ and $R_a$ are the same as the aforementioned.

Further, the present invention provides an organic electroluminescence device which comprises at least one organic thin film layer comprising a light emitting layer sandwiched between a pair of electrode consisting of an anode and a cathode, wherein at least one of the organic thin film layer comprises the material for the organic EL device represented by any one of the general formulae (1) to (3) and (5) singly or as its mixture component.

The material for the organic EL device in the present invention provides a superior organic EL device when the material is employed in a hole injecting region and/or a hole transporting region or a light emitting region, preferably in a hole injecting layer and/or a hole transporting layer or a light emitting layer, further preferably in the hole transporting layer or the light emitting layer.

It is preferable that the hole transporting layer or the light emitting layer contains the material for the organic EL device represented by any one of the general formulae (1) to (3) and (5) in an amount of 0.1 to 20% by mass.

The organic EL device of the present invention emits bluish light.

The construction of the organic EL device of the present invention will be explained in detail below.

(1) Construction of the Organic EL Device

Typical examples of the construction of the organic EL device of the present invention are shown below. However, the present invention is not limited to those shown below.

(1) An anode/a light emitting layer/a cathode;

(2) An anode/a hole injecting layer/a light emitting layer/a cathode;

(3) An anode/a light emitting layer/an electron injecting layer/a cathode;

(4) An anode/a hole injecting layer/a light emitting layer/an electron injecting layer/a cathode;

(5) An anode/an organic semiconductor layer/a light emitting layer/a cathode;

(6) An anode/an organic semiconductor layer/an electron barrier layer/a light emitting layer/a cathode;

(7) An anode/an organic semiconductor layer/a light emitting layer/an adhesion improving layer/a cathode;

(8) An anode/a hole injecting layer/a hole transporting layer/a light emitting layer/an electron injecting layer/a cathode;

(9) An anode/an insulating layer/a light emitting layer/an insulating layer/a cathode;

(10) An anode/an inorganic semiconductor layer/an insulating layer/a light emitting layer/an insulating layer/a cathode;

(11) An anode/an organic semiconductor layer/an insulating layer/a light emitting layer/an insulating layer/a cathode;

(12) An anode/an insulating layer/a hole injecting layer/a hole transporting layer/a light emitting layer/an insulating layer/a cathode; and

(13) An anode/an insulating layer/a hole injecting layer/a hole transporting layer/a light emitting layer/an electron injecting layer/a cathode.

Among the above constructions, constructions (4) and (8) are usually preferable.

Although the materials for the organic EL device of the present invention may be employed for any of the above organic layers, it is preferable that it is contained in a light emitting region or a hole transporting region among those construction elements. It is particularly preferable that they are contained in the hole transporting layer.

(2) Substrate which Transmits Light

In general, the organic EL device is produced on a substrate which transmits light. It is preferable that the substrate which transmits light has a transmittance of light of 50% or greater in the visible wavelength-range of 400 to 700 nanometers. It is also preferable that a flat and smooth substrate is employed.

As the substrate which transmits light, for example, glass sheet and synthetic resin sheet are advantageously employed. Specific examples of the glass sheet include soda ash glass, glass containing barium and strontium, lead glass, aluminosilicate glass, borosilicate glass, barium borosilicate glass and quartz. Specific examples of the synthetic resin sheet include sheet made of polycarbonate resins, acrylic resins, polyethylene terephthalate resins, polyether sulfide resins and polysulfone resins.

(3) Anode

The anode in the organic EL device of the present invention covers a role of injecting holes into a hole transport layer or into a light emitting layer, and it is effective that the anode has a work function of 4.5 eV or greater. Specific examples of the material for the anode include indium tin oxide (ITO) alloy, indium zinc oxide (IZO) alloy, tin oxide (NESA), gold, silver, platinum, copper, lanthanoid, etc. Further, an alloy or a laminate of two kinds or more among those in combination may be employable.

The anode can be prepared by forming a thin film of the electrode material described above in accordance with a process such as the vapor deposition process and the sputtering process.

When the light emitted from the light emitting layer is obtained through the anode, it is preferable that the anode has a transmittance of the emitted light greater than 10%. It is also preferable that the sheet resistivity of the anode is several hundred Ω/□ or smaller. The thickness of the anode is, in general, selected in the range of from 10 nanometers to 1 μm and preferably in the range of from 10 to 200 nanometers.

(4) Light Emitting Layer

In the organic EL device of the present invention, the light emitting layer has the following functions:

Namely, (1) The injecting function: the function of injecting holes from the anode or the hole injecting layer and injecting electrons from the cathode or the electron injecting layer when an electric field is applied;

(2) The transporting function: the function of transporting injected charges (electrons and holes) by the force of the electric field; and (3) The light emitting function: the function of providing the field for recombination of electrons and holes and leading the recombination to the emission of light.

Although there may be a difference between the capability of the holes being injected and the capability of the electrons being injected, and although there may be a grade about the transporting function expressed by mobilities of the holes and the electrons, it is preferable to move charges of either ones.

As the process for forming the light emitting layer, a well known process such as the vapor deposition process, the spin coating process and the Laser Beam (LB) process can be employed. It is particularly preferable that the light emitting layer is a molecular deposit film.

The molecular deposit film is a thin film formed by deposition of a material compound in the gas phase or a thin film formed by solidification of a material compound in a solution or in the liquid phase. In general, the molecular deposit film can be distinguished from the thin film (the molecular accumulation film) formed in accordance with the LB process based on the differences in the aggregation structure and higher order structures and functional differences caused by these structural differences.

In addition, as disclosed in Japanese Patent Application Laid-Open No. Showa 57 (1982)-51781, the light emitting layer can also be formed by dissolving a binder such as a resin and the material compounds into a solvent to prepare a solution, followed by forming a thin film from the prepared solution in accordance with the spin coating process or the like.

In the present invention, any well known light emitting material other than the present invention may be optionally contained in the light emitting layer, or a light emitting layer containing any other well known light emitting material may be laminated with the light emitting layer containing the light emitting material of the present invention each in an extent of not obstructing to achieve the object of the present invention respectively.

With regard to the well known light emitting material, a material having a fused aromatic ring such as anthracene or pyrene in its molecule is particularly preferable. Specific examples will be described below.

A light emitting material or a dopant to be used together with the aromatic amine derivatives includes, for example, anthracene, naphthalene, phenanthrene, pyrene, tetracene, coronene, chrysene, fluorescein, perylene, phthaloperylene, naphthaloperylene, perinone, phthaloperinone, naphthaloperinone, diphenylbutadiene, tetraphenylbutadiene, coumarin, oxadiazole, aldazine, bisbenzooxazoline, bisstyryl, pyrazine, cyclopentadiene, quinolin metal complex, aminoquinolin metal complex, benzoquinolin metal complex, imine, diphenylethylene, vinylanthracene, diaminecarbazol, pyran, thiopyran, polymethyne, merocyanine, imidazol chelate oxinoid compound, quinacridone, rubrene and fluorescent dye, but not limited thereto.

A preferable host material to be used together with the aromatic amine derivatives of the present invention includes compounds represented by following general formulae (i) to (ix).

An asymmetric anthracene represented by a following general formula (i):

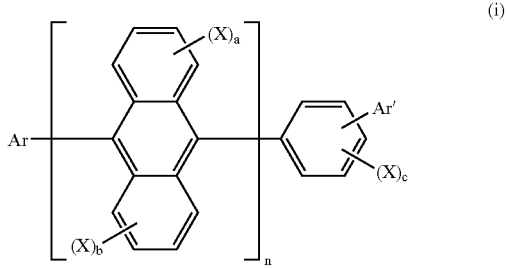

In the above general formula (i), Ar represents a substituted or unsubstituted fused aromatic group having 10 to 50 ring carbon atoms;

Ar' represents a substituted or unsubstituted aromatic group having 6 to 50 ring carbon atoms;

X represents a substituted or unsubstituted aromatic group having 6 to 50 ring carbon atoms, a substituted or unsubstituted aromatic heterocyclic group having 5 to 50 ring atoms, a substituted or unsubstituted alkyl group having 1 to 50 carbon atoms, a substituted or unsubstituted alkoxy group having 1 to 50 carbon atoms, a substituted or unsubstituted aralkyl group having 6 to 50 carbon atoms, a substituted or unsubstituted aryloxy group having 5 to 50 ring atoms, a substituted or unsubstituted arylthio group having 5 to 50 ring atoms, a substituted or unsubstituted alkoxycarbonyl group having 1 to 50 carbon atoms, a carboxyl group, a halogen atom, a cyano group, a nitro group and a hydroxyl group;

a, b and c each independently represents an integer of 0 to 4;

n represents an integer of a to 3; and when n is 2 or greater, within a parentheses: [ ] may be the same with or different from each other.

An asymmetric mono-anthracene derivative represented by a following general formula (ii):

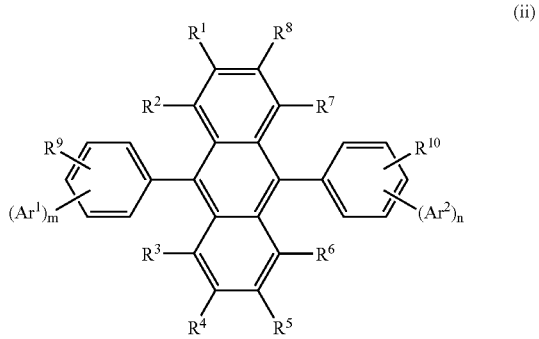

(ii)

In the general formula (ii), $Ar^1$ and $Ar^2$ each independently represents a substituted or unsubstituted aromatic ring group having 6 to 50 ring carbon atoms; m and n each represents an integer of 1 to 4; however, in a case where m=n=1 and at the same time, where each bonding position of $Ar^1$ and $Ar^2$ to a benzene ring is monosymmetric each other, $Ar^1$ is different from $Ar^2$, and in a case where m or n represents an integer of 2 to 4, m is different from n;

$R^1$ to $R^{10}$ each independently represents a hydrogen atom, a substituted or unsubstituted aromatic ring group having 6 to 50 ring carbon atoms, a substituted or unsubstituted aromatic heterocyclic group having 5 to 50 ring atoms, a substituted or unsubstituted alkyl group having 1 to 50 carbon atoms, a substituted or unsubstituted cycloalkyl group, a substituted or unsubstituted alkoxy group having 1 to 50 carbon atoms, a substituted or unsubstituted aralkyl group having 6 to 50 carbon atoms, a substituted or unsubstituted aryloxy group having 5 to 50 ring atoms, a substituted or unsubstituted arylthio group having 5 to 50 ring atoms, a substituted or unsubstituted alkoxycarbonyl group having 1 to 50 carbon atoms, a substituted or unsubstituted silyl group, a carboxyl group, a halogen atom, a cyano group, a nitro group and a hydroxyl group.

An asymmetric pyrene derivative represented by a following general formula (iii):

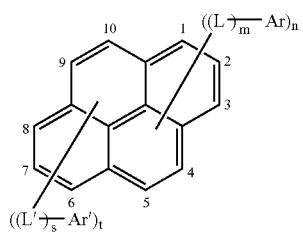

(iii)

In the general formula (iii), Ar and Ar' each represents a substituted or unsubstituted aromatic group having 6 to 50 ring carbon atoms;

L and L' each represents a substituted or unsubstituted phenylene group, a substituted or unsubstituted naphthalenylene group, a substituted or unsubstituted fluorenylene group or a substituted or unsubstituted dibenzosilolylene group;

m represents an integer of 0 to 2, n represents an integer of 1 to 4, s represents an integer of 0 to 2 and t represents an integer of 0 to 4; and, L or Ar bonds to any one of 1 to 5 position of pyrene, also L' or Ar' bonds to any one of 6 to 10 position thereof, however, when n+t makes an even number, Ar, Ar', L and L' satisfy a following requirement (1) or a requirement (2):

(1) Ar≠Ar' and/or L≠L' (wherein ≠ means that each group has a different structure)

(2) when Ar=Ar' and L=L'

(2-1) m≠s and/or n≠t, or (2-2) when m=s and n=t, (2-2-1) both L and L' or pyrene each bonds respectively to different positions of Ar and Ar', or (2-2-2) both L and L' or pyrene each bonds respectively to the same position of Ar and Ar', excluding a case where a pyrene derivative having both L and L' or both Ar and Ar' bond to 1 and 6 positions thereof, or 2 and 7 positions thereof.

An asymmetric anthracene derivative represented by a following general formula (iv):

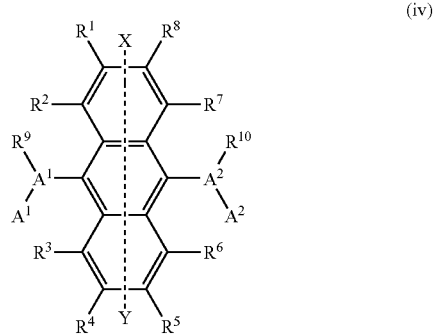

(iv)

In the general formula (iv), $A^1$ and $A^2$ each independently represents a substituted or unsubstituted fused aromatic ring group having 10 to 20 ring carbon atoms;

$Ar^1$ and $Ar^2$ each independently represent a hydrogen atom, a substituted or unsubstituted aromatic ring group having 6 to 50 ring carbon atoms;

$R^1$ to $R^{10}$ each independently represents a hydrogen atom, a substituted or unsubstituted aromatic ring group having 6 to 50 ring carbon atoms, a substituted or unsubstituted aromatic heterocyclic group having 5 to 50 ring atoms, a substituted or unsubstituted alkyl group having 1 to 50 carbon atoms, a substituted or unsubstituted cycloalkyl group, a substituted or unsubstituted alkoxy group having 1 to 50 carbon atoms, a substituted or unsubstituted aralkyl group having 6 to 50 carbon atoms, a substituted or unsubstituted aryloxy group having 5 to 50 ring atoms, a substituted or unsubstituted arylthio group having 5 to 50 ring atoms, a substituted or unsubstituted alkoxycarbonyl group having 1 to 50 carbon atoms, a substituted or unsubstituted silyl group, a carboxyl group, a halogen atom, a cyano group, a nitro group or a hydroxyl group;

$Ar^1$, $Ar^2$, $R^9$ and $R^{10}$ each may be more than one, and two neighboring groups thereof may form a saturated or unsaturated ring structure, however, a case where the groups at 9 and 10 positions of anthracene at the core are symmetrical about X-Y axis of symmetry and bond each other is excluded.

An anthracene derivative represented by a following general formula (v):

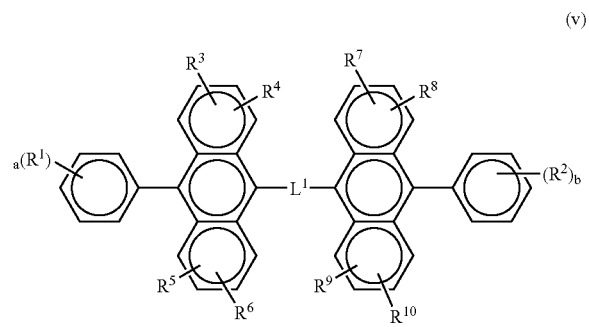

(v)

In the general formula (v), $R^1$ to $R^{10}$ each independently represents a hydrogen atom, an alkyl group, a cycloalkyl group, an aryl group which may be substituted, an alkoxyl group, an aryloxy group, an alkylamino group, an alkenyl group, an arylamino group or a heterocyclic group which may be substituted; a and b each represents an integer of 1 to 5, and when both of a and b are 2 or greater, both $R^1$ or both $R^2$ may be the same with or different from each other, additionally a couple of $R^1$ or both $R^2$ may bond each other to form a ring; a couple of $R^3$ and $R^4$, a couple of $R^5$ and $R^6$, a couple of $R^7$ and $R^8$, and/or a couple of $R^9$ and $R^{10}$ may bond each other to form a ring; $L^1$ represents a single bond, —O—, —S—, —N(R)—, an alkylene group or an arylene; wherein R represents an alkyl group, or an aryl group which may be substituted.

An anthracene derivative represented by a following general formula (vi):

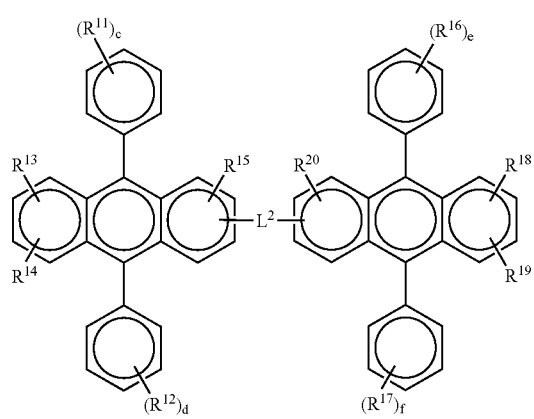

(vi)

In the general formula (vi), $R^{11}$ to $R^{20}$ each independently represents a hydrogen atom, an alkyl group, a cycloalkyl group, an aryl group, an alkoxyl group, an aryloxy group, an alkylamino group, an arylamino group or a heterocyclic group which may be substituted; c, d, e and f each represents an integer of 1 to 5, and when c, d, e and/or f are 2 or greater, plural $R^{11}$, plural $R^{12}$, plural $R^{16}$ or plural $R^{17}$ may be the same with or different from each other, additionally plural $R^{11}$, plural $R^{12}$, plural $R^{16}$ or plural $R^{17}$ may bond each other to form a ring; a couple of $R^{13}$ and $R^{14}$, and/or a couple of $R^{18}$ and $R^{19}$ may bond each other to form a ring; $L^2$ represents a single bond, —O—, —S—, —N(R)—, an alkylene group or an arylene; wherein R represents an alkyl group, or an aryl group which may be substituted.

A spirofluorene derivative represented by a following general formula (vii):

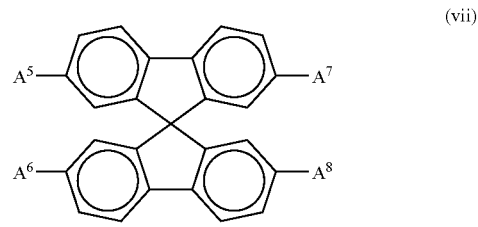

(vii)

In the general formula (vii), $A^5$ to $A^8$ each independently represented a substituted or unsubstituted biphenyl group or a substituted or unsubstituted naphthyl group.

A compound containing a fused ring represented by a following general formula (viii):

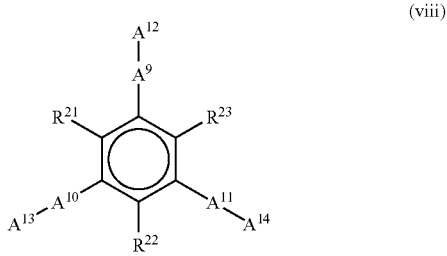

(viii)

In the general formula (viii), $A^9$ to $A^{14}$ each independently represents a substituted or unsubstituted biphenyl group or a substituted or unsubstituted naphthyl group as aforementioned about $A^5$ to $A^8$, and $R^{21}$ to $R^{23}$ each independently represents a hydrogen atom, an alkyl group having 1 to 6 carbon atoms, a cycloalkyl group having 3 to 6 carbon atoms, an alkoxyl group having 1 to 6 carbon atoms, an aryloxy group having 5 to 18 carbon atoms, an aralkyloxy group having 7 to 18 carbon atoms, an arylamino group having 5 to 16 carbon atoms, a nitro group, a cyano group, an ester group having 1 to 6 carbon atoms or a halogen atom, and at least one of $A^9$ to $A^{14}$ represents a fused aromatic ring comprising 3 or more rings.

A fluorene compound represented by a following general formula (ix):

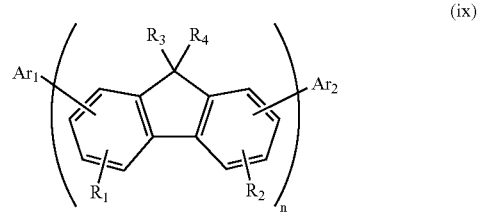

(ix)

In the general formula (ix), $R_1$ and $R_2$ each independently represents a hydrogen atom, a substituted or unsubstituted alkyl group, a substituted or unsubstituted aralkyl group, a substituted or unsubstituted aryl group, a substituted or unsubstituted heterocyclic group, a substituted amino group, a cyano group or a halogen atom; both $R_1$ and both $R_2$ bonding to a different fluorene group may be the same with or different from each other, and both $R_1$ and $R_2$ bonding to the same fluorene group may be the same with or different from each other; $R_3$ and $R_4$ each independently represents a hydrogen atom, a substituted or unsubstituted alkyl group, a substituted or unsubstituted aralkyl group, a substituted or unsubstituted aryl group, or a substituted or unsubstituted heterocyclic group, and both $R_3$ and both $R_4$ bonding to a different fluorene group may be the same with or different from each other, and also both $R_3$ and $R_4$ bonding to the same fluorene group may be the same with or different from each other; $Ar_1$ and $Ar_2$ each independently represents a substituted or unsubstituted fused polycyclic aromatic group consisting of benzene rings of 3 or more or a substituted or unsubstituted fused polycyclic heterocyclic group comprising of benzene rings and hetero rings of 3 or more in total; $Ar_1$ and $Ar_2$ may be the same with or different from each other; and n represents an integer of 1 to 10.

Among the above host materials, an anthracene derivative is preferable and a monoanthracene derivative is more preferable, further an asymmetric anthracene is particularly preferable.

In addition, a phosphorescent compound may be employed as a light emitting material for a dopant. A compound containing a carbazole ring for a host material is preferable as the phosphorescent compound. Although the dopant is a compound which is able to emit light from triplet exciton and is not limited as long as emitting light from triplet exciton, it is preferable that the dopant is a metal complex containing at least a metal selected from a group consisting of Ir, Ru, Pd, Pt, Os and Re.

A suitable host for phosphorescence comprising a compound containing a carbazole ring is a compound having a function of making a phosphorescent compound to emit light as a result of energy transfer from its excitation state to the phosphorescent compound. With regard to the host compound, any compound being able to transfer exciton energy to the phosphorescent compound may be selected, without particularly restricted, for the purpose as appropriate. Any heterocyclic compound excluding a carbazole ring may be contained.

Specific examples of the host compound include a carbazole derivative, a triazole derivative, an oxazole derivative, an oxadiazole derivatives, an imidazole derivative, a polyarylalkane derivative, a pyrazoline derivative, a pyrazlone derivative, a phenylene diamine derivative, an arylamine derivative, a calcone derivative substituted by amine, a styrylanthracene derivative, a fluorennone derivative, a hydrazone derivative, a stilbene derivative, a silazane derivative, an aromatic tertiary amine compound, a styrylamine compound, an aromatic dimethylidene type compound, a porphyrin type compound, an anthraquinodimethane derivative, an anthrone derivative, a diphenylquinon derivative, a thiopyrandioxide derivative, a carbodimide derivative, a fluorenylidene methane derivative, a distyrylpyrazine derivative, heterocyclic tetracarboxylic anhydride such as a naphthaleneperylene, a phthalocyanine derivative, a metal complex or a metallophthalocyanine of 8-quinolinol derivative; various metal complex polysilane-based compound represented by a metal complex having a ligand of benzoxazole or benzothiazole; an electro-conductive oligomer such as a poly(N-vinylcarbazole) derivative, an aniline-based copolymer, a thiophene oligomer, a polythiophene and so on; polymer compound such as a polythiophene derivative, a polyphenylene derivative, a polyphenylenevinylene derivative, a polyfluorene derivative and the like. The host compounds may be used singly or in combination of two or more.

More specific examples include the following:

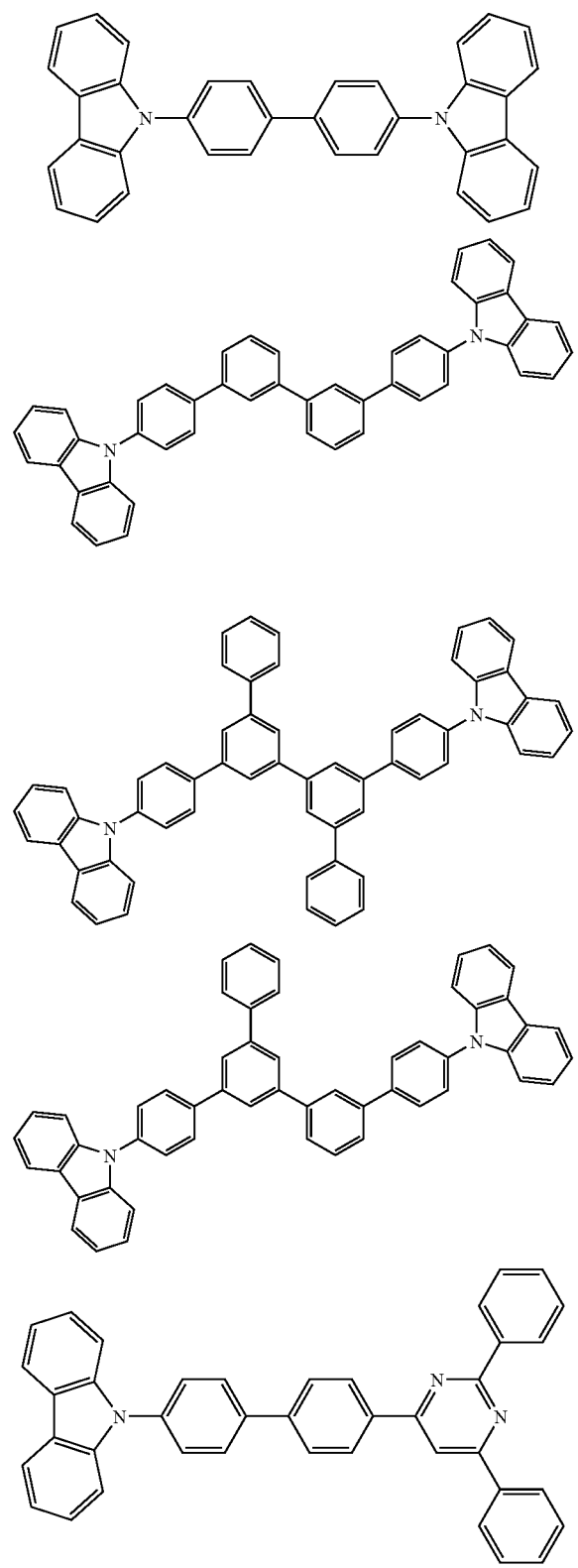

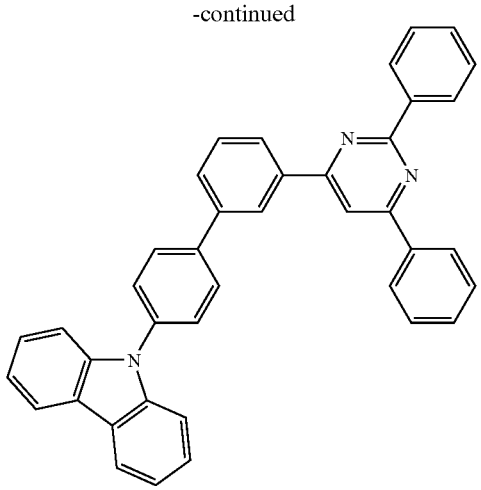

The phosphorescent dopant is a compound capable of emitting light from the triplet exciton. Although it is not restricted as long as it emits light from the triplet exciton, it is preferable that a metal complex comprises at least a metal selected from the group of Ir, Ru, Pd, Pt, Os and Re. A porphyrin metal complex or an orthometalized metal complex is particularly preferable. As the porphyrin metal complex, a porphyrin platinum complex is preferable. The phosphorescent compound may be employed singly or in combination of two or more.

Although there are various ligands to form an orthometalized metal complex, preferred ligands includes 2-phenylpyridine derivatives, 7,8-benzoquinoline derivatives, 2-(2-thienyl)pyridine derivatives, 2-(1-naphthyl)pyridine derivatives, 2-phenylquinoline derivatives and the like. The derivatives may have substituent as option. In particular, the derivatives having a fluorinated compound or a trifluoromethyl group are preferable for a bluish dopant. In addition, a ligand other than the above ligand such as acetylacetonate and picric acid may be contained as an auxiliary ligand.

The amount of the phosphorescent dopant in the light emitting layer may be selected for the objective as appropriate without particularly restricted, and for example, it may be selected in the range of from 0.1 to 70% by mass, preferably in the range of from 1 to 30% by mass. The emission is faint and the advantage is not demonstrated when the amount is less than 0.1% by mass. The concentration quenching becomes noticeable so that the device performance is deteriorated when the amount is more than 70% by mass.

Further, the light emitting layer may contain a hole transporting material, a electron transporting material or a polymer binder as option.

Furthermore, the thickness of the light emitting layer is, in general, selected in the range of from 5 to 50 nanometers, preferably in the range of from 7 to 50 nanometers and more preferably in the range of from 10 to 50 nanometers. It is resulted in difficulties to form the light emitting layer and to control chromaticity thereof when the thickness is less than 5 nanometers, and it may be resulted in danger of increasing driving voltage when it is more than 50 nanometers.

(5) Hole injecting layer, hole transporting layer

The hole injecting layer and the hole transporting layer are layers which help injection of holes into the light emitting layer and transport the holes to the light emitting region. The layers exhibit a great mobility of holes and, in general, have an ionization energy as small as 5.5 eV or smaller. For the hole injecting layer and the hole transporting layer, a material which transports holes to the light emitting layer at a small strength of the electric field is preferable. A material which exhibits, for example, a mobility of holes of at least $10^{-4}$ $cm^2/V \cdot second$ under application of an electric field of from $10^4$ to $10^6$ V/cm is preferable.

When the compound of the present invention is employed in the hole transporting region, the hole injecting layer or the hole transporting layer may be composed of only the compound of the present invention singly or may be composed of both the compound of the present invention and any other material in combination.

With regard to the material which may be employed for forming the hole injecting layer or the hole transporting layer in combination with the compound of the present invention, any material having the foregoing preferable properties is employed without particularly restricted, any arbitrary material select from conventional material commonly used as a charge transporting material for the holes in photoconductive materials and well known material employed for the hole injecting layer in the EL device is usable. Regarding with the aromatic amine derivative, a compound expressed with a following general formula is employable.

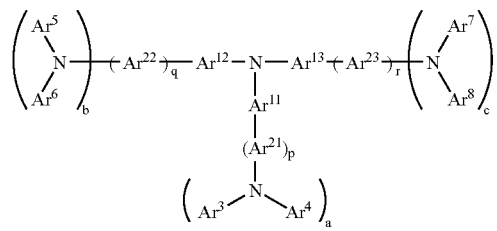

In the formula, $Ar^3$ to $Ar^8$, $Ar^{11}$ to $Ar^{13}$ and $Ar^{21}$ to $Ar^{23}$ each independently represents a substituted or unsubstituted aromatic group having 6 to 50 ring carbon atoms or a substituted or unsubstituted heteroaromatic group having 5 to 50 ring atoms; a, b, c, p, q and r each independently represents an integer of 0 to 3; and a couple of $Ar^3$ and $Ar^4$, a couple of $Ar^5$ and $Ar^6$, and a couple of $Ar^7$ and $Ar^8$ may bond each other to form a saturated or unsaturated ring structure.

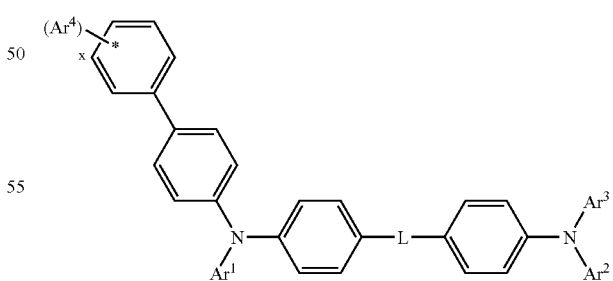

In the formula, $Ar^1$ to $Ar^4$ each independently represents a substituted or unsubstituted aromatic group having 6 to 50 ring carbon atoms or a substituted or unsubstituted heteroaromatic group having 5 to 50 ring atoms; L is a coupling group, and represents a single bond or a substituted or unsubstituted aromatic group having 6 to 50 ring carbon atoms or a substituted or unsubstituted heteroaromatic group having 5 to 50 ring atoms; X represents an integer of 0 to 5; and a couple of $Ar^2$ and $Ar^3$ may bond each other to form a saturated or unsaturated ring structure.

Specific examples include triazole derivatives (refer to U.S. Pat. No. 3,112,197, etc.), oxadiazole derivatives (refer to U.S. Pat. No. 3,189,447, etc.), imidazole derivatives (refer to Japanese Examined Patent KOKOKU No. Shou 37-16096, etc.), poly arylalkane derivatives (refer to U.S. Pat. Nos. 3,615,402, 3,820,989 and 3,542,544, Japanese Examined Patent KOKOKU Nos. Shou 45-555 and Shou 51-10983, Japanese Unexamined Patent Application Laid Open Nos. Shou 51-93224, Shou 55-17105, Shou 56-4148, Shou 55-108667, Shou 55-156953, Shou 56-36656, etc.), pyrazoline derivatives and pyrazolone derivatives (refer to U.S. Pat. Nos. 3,180,729 and 4,278,746, Japanese Unexamined Application Patent Laid Open Nos. Shou 55-88064, Shou 55-88065, Shou 49-105537, Shou 55-51086, Shou 56-80051, Shou 56-88141, Shou 57-45545, Shou 54-112637, Shou 55-74546, etc.), phenylenediamine derivatives (refer to U.S. Pat. No. 3,615,404, Japanese Examined Patent KOKOKU Nos. Shou 51-10105, Shou 46-3712 and Shou 47-25336, Japanese Unexamined Patent Application Laid Open Nos. Shou 54-53435, Shou 54-110536, Shou 54-119925, etc.), arylamine derivatives (refer to U.S. Pat. Nos. 3,567,450, 3,180,703, 3,240,597, 3,658,520, 4,232,103, 4,175,961 and 4,012,376, Japanese Examined Patent KOKOKU Nos. Shou 49-35702 and Shou 39-27577, Japanese Unexamined Patent Application Laid Open Nos. Shou 55-144250, Shou 56-119132 and Shou 56-22437, West German Patent No. 1,110,518, etc.), Chalcone derivatives which is substituted with amino group (refer to U.S. Pat. No. 3,526,501, etc.), oxazole derivatives (disclosed in U.S. Pat. No. 3,257,203, etc.), styryl anthracene derivatives (refer to Japanese Unexamine Patent Application Laid Open No. Shou 56-46234, etc.), fluorenone derivatives (refer to Japanese Unexamined Patent Application Laid Open No. Shou 54-110837, etc.), hydrazone derivatives (refer to U.S. Pat. No. 3,717,462, Japanese Unexamined Patent Application Laid Open Nos. Shou 54-59143, Shou 55-52063, Shou 55-52064, Shou 55-46760, Shou 55-85495, Shou 57-11350, Shou 57-148749, Hei 2-311591, etc.), stilbene derivatives (refer to Japanese Unexamined Patent Application Laid Open Nos. Shou 61-210363, Shou 61-228451, Shou 61-14642, Shou 61-72255, Shou 62-47646, Shou 62-36674, Shou 62-10652, Shou 62-30255, Shou 60-93455, Shou 60-94462, Shou 60-174749, Shou 60-175052, etc.), silazane derivatives (U.S. Pat. No. 4,950,950), polysilane-based copolymers (Japanese Unexamined Patent Application Laid-Open No. Hei 2-204996), aniline-based copolymers (Japanese Unexamined Patent Application Laid-Open No. Hei 2-282263), an electroconductive polymer oligomer which is disclosed in Japanese Unexamined Patent Application Laid-Open No Hei 1-211399 (particularly, thiophene oligomer), etc.

With regard to the material of the hole injecting layer, the above materials are also employable, however, porphyrin compounds, aromatic tertiary amine compounds and styryl amine compounds (refer to U.S. Pat. No. 4,127,412, Japanese Unexamined Patent Application Laid Open Nos. Shou 53-27033, Shou 54-58445, Shou 54-149634, Shou 54-64299, Shou 55-79450, Shou 55-144250, Shou 56-119132, Shou 61-295558, Shou 61-98353, Shou 63-295695, etc.) are preferable and the aromatic tertiary amine compounds are particularly preferable.

Further examples include, for example, 4,4'-bis(N-(1-naphthyl) —N-phenylamino)biphenyl (abbreviated as NPD below) having 2 fused aromatic rings in its molecule described in U.S. Pat. Nos. 5,061,569, 4,4',4"-tris (N-(3-methylphenyl)-N-phenylamino)triphenylamine (abbreviated as MTDATA below) made by connecting three triphenylamine units to form a star burst type, etc.

Besides, a compound with heterocyclic derivative structure having a nitrogen atom expressed with a following general formula disclosed in Japanese Registered Patent No. 03571977 is also employable.

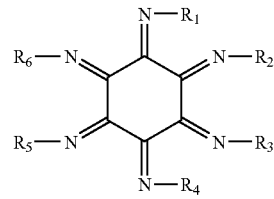

In the formula, $R_1$, $R_2$, $R_3$, $R_4$, $R_5$ and $R_6$ each independently represents any one of a substituted or unsubstituted alkyl group, a substituted or unsubstituted aryl group, a substituted or unsubstituted aralkyl group or a substituted or unsubstituted heterocyclic group. However, $R_1$, $R_2$, $R_3$, $R_4$, $R_5$ and $R_6$ may be the same with or different from each other. Further, a couple of $R_1$ and $R_2$, a couple of $R_3$ and $R_4$, a couple of $R_5$ and $R_6$; or a couple of $R_1$ and $R_6$, a couple of $R_2$ and $R_3$, and a couple of $R_4$ and $R_5$ may bond each other to form a fused ring structure.

Still further, a compound expressed with a following general formula disclosed in US Patent Application Publication No. 2004/0113547 is also employable.

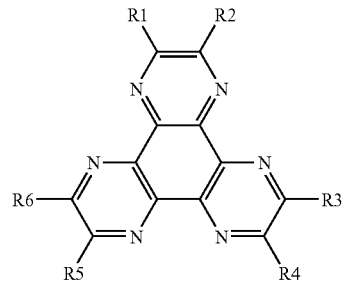

In the formula, R1 to R6 are substituents, and preferably, they each independently represents an electron withdrawing group such as cyano group, nitro group, sulfonyl group, carbonyl group, trifluoromethyl group, halogen atom, etc.

Further, except the above-mentioned aromatic dimethylidene-based compound described as a material for the light emitting layer, inorganic compound such as p-type silicon, p-type silicon carbide or so is employable as the material for the hole injecting layer. To form the hole injecting layer or the hole transporting layer, a thin film may be formed from the material for the hole injecting layer or the hole transporting layer, respectively, in accordance with a well known process such as the vacuum vapor deposition process, the spin coating process, the casting process and the LB process. Although the thickness of the hole injecting layer and the hole transporting layer is not particularly limited, the thickness is usually from 5 nanometers to 5 μm. It is preferable that the hole injecting layer or the hole transporting layer comprises the compound of the present invention in the hole transporting region. Further, the hole injecting layer or the hole transporting layer may be composed of single layer comprising one or more kind of those materials or may be laminated with a hole injecting layer or a hole transporting layer each comprising another kind of compound respectively.

In the organic EL device of the present invention, the organic semiconductor layer assists to inject the holes or to inject the electrons into the light emitting layer, and it is preferable for the organic semiconductor layer to have a conductance of $10^{-10}$ S/cm or greater. With regard to a material for the organic semiconductor layer, electro-conductive oligomers such as an oligomer having thiophene, an oligomer having arylamine disclosed in Japanese Unexamined Patent Application Laid-Open No. Hei 8-193191 and so on, electro-conductive dendrimers such as a dendrimer having an arylamine dendrimer and so on are employable.

(6) Electron Injection Layer

The electron injection layer in the organic EL device of the present invention is a layer which assists injection of electrons into the light emitting layer and exhibits a great mobility of electrons. Among the electron injecting layers, an adhesion improving layer is a layer made of a material exhibiting excellent adhesion with the cathode. As the material for the electron injecting layer, 8-hydroxyquinoline, metal complexes of derivatives thereof and oxadiazole derivatives are preferable. Examples of the 8-hydroxyquinoline and metal complexes of derivatives thereof include metal chelate of oxinoid compounds including chelate of oxine (in general, 8-quinolinol or 8-hydroxyquinoline).

For example, tris(8-quinolinol)aluminum (alq) can be employed as the electron injecting material.

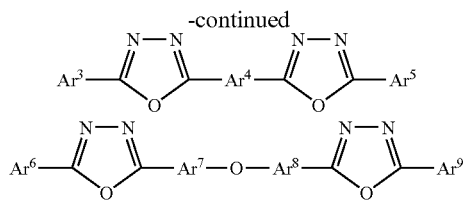

wherein $Ar^1$, $Ar^2$, $Ar^3$, $Ar^5$, $Ar^6$ and $Ar^9$ each independently represents a substituted or unsubstituted aryl group respectively, which may be the same with or different from each other; $Ar^4$, $Ar^7$ and $Ar^8$ each independently represents a substituted or unsubstituted arylene group, which may be the same with or different from each other.

Examples of aryl group include a phenyl group, a biphenyl group, an anthranil group, a perilenyl group and a pyrenyl group. Further, examples of the arylene group include a phenylene group, a naphthylene group, a biphenylene group, an anthranylene group, a perilenylene group, a pyrenylene group, etc. Furthermore, examples of the substituent include an alkyl group having 1 to 10 carbon atoms, an alkoxy group or a cyano group each having 1 to 10 carbon atoms respectively, etc. With regard to the electron transfer compound, those compounds having a thin film forming capability are preferable.

Specific examples of the electron transfer compounds are shown below:

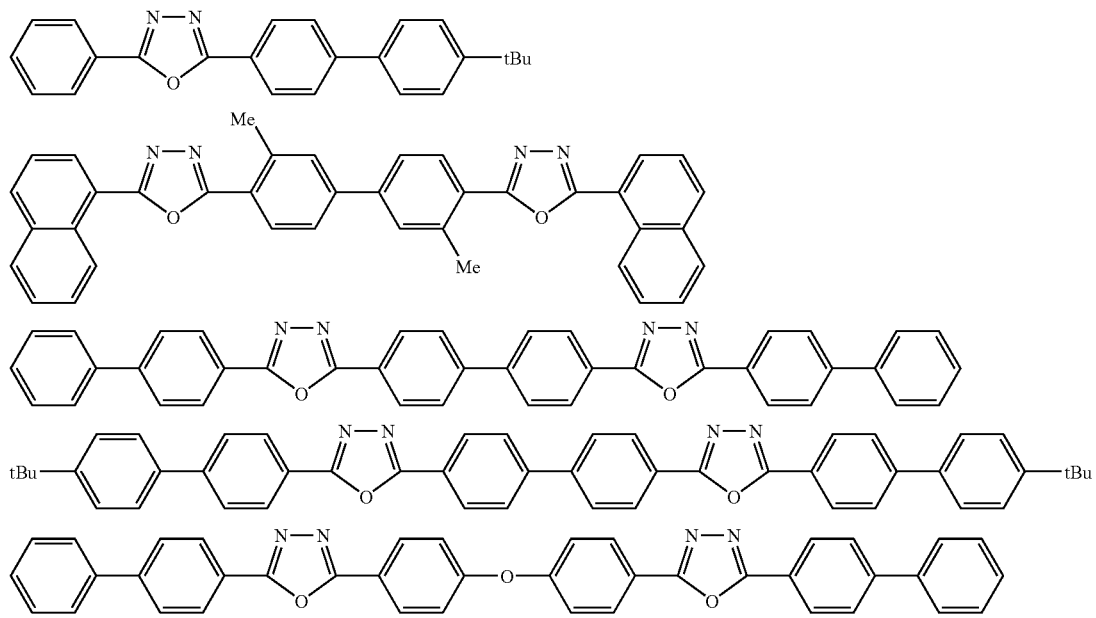

Further, examples of the oxadiazole delivertives include an electron transfer compound shown as the following general formulae:

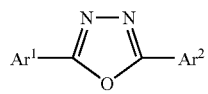

Further, it is known that another compound with heterocycles having a nitrogen atom is preferable as the electron transporting material.

Further, materials shown by following general formulae (E) to (J) are employable for the electron injecting layer and the electron transporting layer.

A heterocyclic derivative having a nitrogen atom represented by a following general formula (E) or general formula (F):

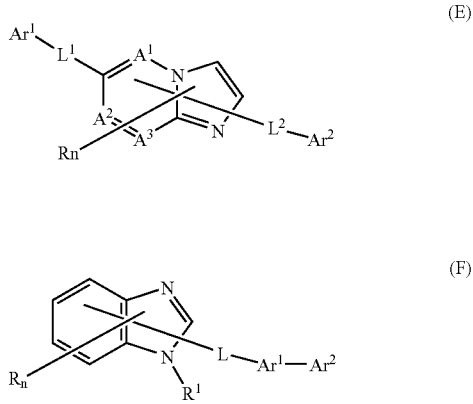

(E)

(F)

In the general formulae (E) and (F), $A^1$ to $A^3$ each independently represents a nitrogen atom or a carbon atom;

$Ar^1$ represents a substituted or unsubstituted aryl group having 6 to 60 ring carbon atoms or a substituted or unsubstituted heteroaryl group having 3 to 60 ring carbon atoms; $Ar^2$ represents a hydrogen atom, a substituted or unsubstituted aryl group having 6 to 60 ring carbon atoms, a substituted or unsubstituted heteroaryl group having 3 to 60 ring carbon atoms, a substituted or unsubstituted alkyl group having 1 to 20 carbon atoms, a substituted or unsubstituted alkoxy group having 1 to 20 carbon atoms or those divalent groups. However, at least one of $Ar^1$ or $Ar^2$ represents a substituted or unsubstituted fused ring group having 10 to 60 ring carbon atoms or a substituted or unsubstituted monohetero fused ring group having 3 to 60 ring carbon atoms;

$L^1$, $L^2$ and L each independently represents a single bond, a substituted or unsubstituted arylene group having 6 to 60 ring carbon atoms, a substituted or unsubstituted heteroarylene group having 3 to 60 ring carbon atoms or a substituted or unsubstituted fluorenylene group;

R represents a hydrogen atom, a substituted or unsubstituted aryl group having 6 to 60 ring carbon atoms, a substituted or unsubstituted heteroaryl group having 3 to 60 ring carbon atoms, a substituted or unsubstituted alkyl group having 1 to 20 carbon atoms, or a substituted or unsubstituted alkoxy group having 1 to 20 carbon atoms; n represents an integer of 0 to 5; when n is 2 or greater, plural of R may be the same with or different from each other; and adjacent couple of the plural of R may bond each other to form a carbocyclic aliphatic ring or a carbocyclic aromatic ring.

A heterocyclic derivative having a nitrogen atom represented by a following general formula (G):

$$HAr-L-Ar^1-Ar^2 \quad (G)$$

wherein HAr represents a heterocyclic group having a nitrogen atom, which has 3 to 40 carbon atoms and which may have a substituent; L represents a single bond, an arylene group having 6 to 60 carbon atoms and may have a substituent, a heteroarylene group having 3 to 60 carbon atoms and may have a substituent or a fluorenylene group which may have a substituent; $Ar^1$ represents a divalent aromatic hydrocarbon group having 6 to 60 carbon atoms and may have a substituent; and $Ar^2$ represents an aryl group having 6 to 60 carbon atoms and may have a substituent or a heteroaryl group having 3 to 60 carbon atoms and may have a substituent.

A silacyclopentadiene derivative represented by a following general formula (H):

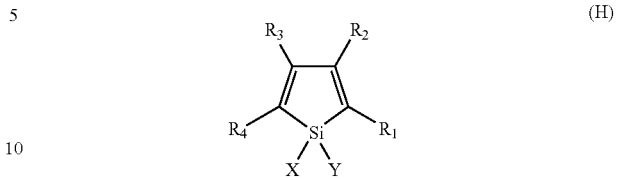

wherein X and Y each independently represents a saturated or unsaturated hydrorocarbon group having 1 to 6 carbon atoms, an alkoxy group, an alkenyloxy group, an alkynyloxy group, a hydroxy group, a substituted or unsubstituted aryl group, a substituted or unsubstituted hetero ring, or a structure forming a saturated or unsaturated ring by bonding X and Y; $R_1$ to $R_4$ each independently represents a hydrogen atom, a halogen atom, a substituted or unsubstituted alkyl group having 1 to 6 carbon atoms, an alkoxy group, an aryloxy group, a perfluoroalkyl group, a perfluoro alkoxy group, an amino group, an alkyl carbonyl group, an arylcarbonyl group, an alkoxycarbonyl group, an aryloxycarbonyl group, an azo group, an alkylcarbonyl oxy group, an arylcarbonyl oxy group, akkoxycarbonyl oxy group, aryloxy carbonyl oxy group, a sulfinyl group, a sulfonyl group, a sulfanilic group, a silyl group, a carbamoyl group, an aryl group, a hetero ring group, an alkenyl group, an alkynyl group, a nitro group, a formyl group, a nitroso group, a formyloxy group, an isocyano group, a cyanate group, an isocyanate group, a thiocyanate group, an isothiocyanate group or a cyano group; or in an adjacent case, a structure made by fusing a substituted or unsubstituted ring.

A borane derivative represented by a following general formula (I):

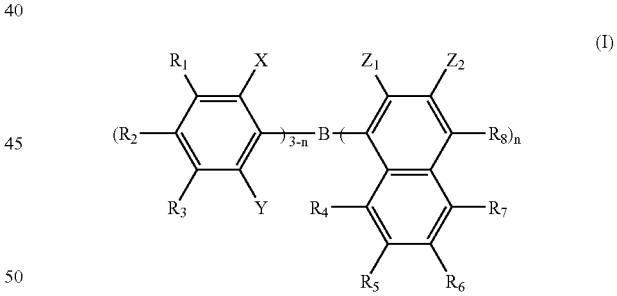

wherein $R_1$ to $R_5$ and $Z_2$ each independently represents a hydrogen atom, a saturated or unsaturated hydrocarbon group, an aromatic group, a hetero ring group, substituted amino group, a substituted boryl group, an alkoxy group or an aryloxy group; X, Y and $Z_1$ each independently represents a saturated or unsaturated hydrocarbon group, an aromatic group, a heterocyclic group, substituted amino group, an alkoxy group or an aryloxy group; substituents of $Z_1$ and $Z_2$ may bonds each other to form a fused ring; n represents an integer of 1 to 3, and when n is 2 or greater, plural of $Z_1$ may be different from each other; however, a case where n is 1, where X, Y and $R_2$ are methyl groups, and where $R_8$ is a hydrogen atom or a substituted boryl group and a case where n is 3 and where $Z_1$ is a methyl group are excluded.

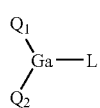

(J)

wherein $Q_1$ and $Q_2$ each independently represents a ligand expressed by a following general formula (K), L represents a halogen atom, a substituted or unsubstituted alkyl group, a substituted or unsubstituted cycloalkyl group, a substituted or unsubstituted aryl group, a substituted or unsubstituted heterocyclic group, and —$OR^1$ ($R^1$ represents a hydrogen atom, a substituted or unsubstituted alkyl group, a substituted or unsubstituted cycloalkyl group, a substituted or unsubstituted aryl group, a substituted or unsubstituted heterocyclic group) or a ligand expressed by —O—Ga-$Q^3(Q^4)$ wherein $Q^3$ and $Q^4$ are the same as $Q_1$ and $Q_2$.

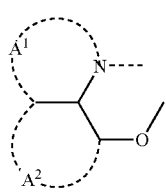

(K)

wherein $A^1$ and $A^2$ each represents a fused 6 member-aryl ring structure which may be substituted.

The metal-complex is powerfully characterized as n type semiconductor, and its electron injection capability is exciting. Besides, because generation energy in complex formation is small, bonding property between the metal in the formed metal-complex and the ligand becomes strong, and as a result, fluorescence quantum efficiency as the light emitting material also becomes great.

Specific examples of substituents of rings $A^1$ and $A^2$ each forming the ligand of general formula (K) include halogen atoms such as chlorine atom, bromine atom, iodine atom and fluorine atom; substituted or unsubstituted alkyl group such as methyl group, ethyl group, propyl group, butyl group, s-butyl group, t-butyl group, pentyl group, hexyl group, heptyl group, octyl group, stearyl group, trichloromethyl group, etc.; substituted or unsubstituted aryl group such as phenyl group, naphthyl group, 3-methylphenyl group, 3-methoxyphenyl group, 3-fluorophenyl group, 3-trichloromethylphenyl group, 3-trifluoromethylphenyl group, 3-nitrophenyl group, etc.; substituted or unsubstituted alkoxy group such as methoxy group, n-butoxy group, t-butoxy group, trichloromethoxy group, trifluoroethoxy group, pentafluoropropoxy group, 2,2,3,3-tetrafluoropropoxy group, 1,1,1,3,3,3-hexafluoro-2-propoxy group, 6-(perfluoroethyl)hexyloxy group, etc.; substituted or unsubstituted aryloxy group such as phenoxy group, p-nitrophenoxy group, p-tert-butylphenoxy group, 3-fluorophenoxy group, pentafluorophenyl group, 3-trifluoromethylphenoxy group, etc.; substituted or unsubstituted alkylthio group such as methylthio group, ethylthio group, tert-butylthio group, hexylthio group, octylthio group, trifluoromethylthio group, etc.; substituted or unsubstituted arylthio group such as phenylthio group, p-nitrophenylthio group, p-tert-butylphenylthio group, 3-fluorophenylthio group, pentafluorophenylthio group, 3-trifluoromethylphenylthio group, etc.; mono- or di-substituted amino group such as cyano group, nitro group, amino group, methylamino group, diethylamino group, ethylamino group, diethylamino group, dipropylamino group, dibutyl amino group, diphenylamino group, etc.; acylamino-group such as bis(acetoxymethyl)amino group, bis(acetoxyethyl) amino group, bis(acetoxypropyl)amino group, bis(acetoxybutyl) amino group, etc.; carbamoyl group such as hydroxy group, siloxy group, acyl group, methylcarbamoyl group, dimethylcarbamoyl group, ethylcarbamoyl group, diethylcarbamoyl group, a propylcarbamoyl group, butyl carbamoyl group, a phenylcarbamoyl group, etc.; cycloalkyl group such as carboxylic acid group, sulfonic acid group, imido group, cyclopentane group, cyclohexyl group, etc.; aryl group such as phenyl group, naphthyl group, biphenyl group, anthranil group, phenanthryl group, fluorenyl group, pyrenyl group, etc.; heterocyclic group such as pyridinyl group, pyrazinyl group, pyrimidinyl group, pyridazinyl group, triazinyl group, indolinyl group, quinolinyl group, acridinyl group, pyrrolidinyl group, dioxanyl group, piperidinyl group, morpholidinyl group, piperazinyl group, triazinyl group, carbazolyl group, furanyl group, thiophenyl group, oxazolyl group, an oxadiazolyl group, a benzoxazolyl group, a thiazolyl group, a thiadiazolyl group, benzothiazolyl group, triazolyl group, imidazolyl group, benzimidazolyl group, pranyl group, etc. Further, above-mentioned substituents may bond each other to form further 6 membered aryl ring or heterocycle.

In the present invention, it is preferable that a reductive dopant is added in either the electron transporting region or an interfacial region between the cathode and the organic layer. The reductive dopant used in the present invention is defined as a substance which reduces the electron transporting compound. Examples of the reductive dopant include at least one compound selected from alkali metals, alkali metallic complexes, alkali metal compounds, alkaline earth metals, alkaline earth metallic complexes, alkaline earth metal compounds, rare earth metals, rare earth metallic complexes and rare earth metal compounds. Examples of the alkali metal compound, the alkaline earth metal compound and the rare earth metal compound described above include oxides and halides of the respective metals.

Examples of the preferable reductive dopant include at least one alkali metal selected from a group consisting of Na (the work function: 2.36 eV), K (the work function: 2.28 eV), Rb (the work function: 2.16 eV) and Cs (the work function: 1.95 eV) or at least one alkaline earth metals selected from a group consisting of Ca (the work function: 2.9 eV), Sr (the work function: 2.0 to 2.5 eV) and Ba (the work function: 2.52 eV); whose work function of 2.9 eV or smaller is particularly preferable. Among those, more preferable reductive dopants include at least one kind or more alkali metal selected from the group consisting of K, Rb and Cs, the latter Rb or Cs being farther more preferable and the last Cs being the most preferable. Those alkali metals have particularly high reducing capability, and only an addition of relatively small amount of them into an electron injection region enables to achieve both improvement of luminance and lifetime extension of the organic EL device. Further, with regard to the reductive dopant with work function of 2.9 eV or smaller, a combination of two or more kinds of the alkali metal is also preferable, and particularly, combinations containing Cs, for example, combinations of Cs and Na, Cs and K, Cs and Rb, or Cs and Na and K are preferable. Containing Cs in combination enables to reveal reducing capability effectively, and the addition into the electron injection region expects both improvement of luminance and lifetime extension of the organic EL device.

In the organic EL device of the present invention, an electron injecting layer comprising electric insulating material and semiconductor may be disposed between the cathode and the organic layer. The disposition of the electron injecting layer enables to effectively prevent a leak of electric current and to improve the electron injection property. It is preferable that at least one metal compound selected from the group consisting of alkali metal chalcogenides, alkaline earth metal chalcogenides, alkali metal halides and alkaline earth metal halides is used as the insulating material. It is preferable that the electron injecting layer is constituted with the above alkali metal chalcogenide since the electron injecting property can be improved. Preferable examples of the alkali metal chalcogenide include $Li_2O$, LiO, $Na_2S$ and $Na_2Se$. Preferable examples of the alkaline earth metal chalcogenide include CaO, BaO, SrO, BeO, BaS and CaSe. Preferable examples of the alkali metal halide include LiF, NaF, KF, LiCl, KCl and NaCl. Preferable examples of the alkaline earth metal halide include fluorides such as $CaF_2$, $BaF_2$, $SrF_2$, $MgF_2$ and $BeF_2$ and halides other than the fluorides.

Examples of the semiconductor constituting the electron transporting layer include oxides, nitrides and oxide nitrides containing at least one element selected from Ba, Ca, Sr, Yb, Al, Ga, In, Li, Na, Cd, Mg, Si, Ta, Sb and Zn, which are used singly or in combination of two or more. It is preferable that the inorganic compound constituting the electron transporting layer is in the form of a fine crystalline or amorphous insulating thin film. When the electron transporting layer is constituted with the above insulating thin film, a more uniform thin film can be formed and defective pixels such as dark spots can be decreased. Examples of the inorganic compound include the alkali metal chalcogenides, the alkaline earth metal chalcogenides, the alkali metal halides and the alkaline earth metal halides which are described above.

(7) Cathode

As the cathode, an electrode substance such as metal, alloy, electro-conductive compound and those mixture having a small work function (4 eV or smaller) is employed. Examples of the electrode substance include sodium, sodium-potassium alloy, magnesium, lithium, magnesium-silver alloy, aluminum/aluminum oxide, aluminum-lithium alloy, indium, rare earth metal, etc.

The cathode can be prepared by forming a thin film of the electrode material described above in accordance with a process such as the vapor deposition process and the sputtering process.

When the light emitted from the light emitting layer is obtained through the cathode, it is preferable that the cathode has a transmittance of the emitted light greater than 10%.

It is also preferable that the sheet resistivity of the cathode is several hundred $\Omega/\Box$ or smaller and that the thickness of the cathode is, in general, selected in the range of from 10 nanometers to 1 μm and preferably in the range of from 50 to 200 nanometers.

(8) Insulating Layer

In general, an organic EL device tends to form defects in pixels due to leak and short circuit since an electric field is applied to ultra-thin films. To prevent the formation of the defects, a layer of an insulating thin film may be inserted between the pair of electrodes.

Examples of the material employed for the insulating layer include aluminum oxide, lithium fluoride, lithium oxide, cesium fluoride, cesium oxide, magnesium oxide, magnesium fluoride, calcium oxide, calcium fluoride, aluminum nitride, titanium oxide, silicon oxide, germanium oxide, silicon nitride, boron nitride, molybdenum oxide, ruthenium oxide and vanadium oxide.

Mixtures and laminates of the above compounds can also be employed.

(9) Fabrication Example of an Organic EL Device

To fabricate an organic EL device of the present invention, for example, an anode, a light emitting layer and, where necessary, a hole injecting layer and an electron injecting layer are formed in accordance with the aforementioned process using the aforementioned materials, and a cathode is formed in the last step. An organic EL device may be produced by forming the aforementioned layers in the order reverse to that described above, i.e., a cathode being formed in the first step and an anode in the last step.

An embodiment of the process for fabricating an organic EL device having a construction in which an anode, a hole injecting layer, a light emitting layer, an electron injecting layer and a cathode are disposed sequentially on a light-transmitting substrate will be described in the following.

First, a thin film consisting of a desired electrode substance, for example, a substance for the anode is formed over a suitable substrate so as to finally achieve a film thickness of 1 μm or thinner, preferably within a range from 10 nanometers to 200 nanometers in accordance with a vapor deposition method, a sputtering method, etc. Then, a hole injecting layer is formed on the anode. The hole injecting layer can be formed in accordance with the vacuum vapor deposition process, the spin coating process, the casting process or the LB process, as described above. The vacuum vapor deposition process is preferable since a uniform film can be easily obtained and the possibility of formation of pin holes is small. When the hole injecting layer is formed in accordance with the vacuum vapor deposition process, it is preferable that the conditions in general are suitably selected in the following ranges: temperature of the deposition source: 50 to 450° C.; vacuum level: $10^{-7}$ to $10^{-3}$ torr; deposition rate: 0.01 to 50 nanometers/second; temperature of the substrate: −50 to 300° C.; and film thickness: 5 nanometers to 5 μm; although the conditions of the vacuum vapor deposition are different depending on the employed compound (the material for the hole injecting layer) and the crystal structure and the recombination structure of the hole injecting layer to be formed.

Subsequently, the light-emitting layer is formed on the hole-injecting layer formed above. Also the formation of the light emitting layer can be made by forming the light emitting material according to the present invention into a thin film in accordance with the vacuum vapor deposition process, the sputtering process, the spin coating process or the casting process. The vacuum vapor deposition process is preferable because a uniform film can be easily obtained and the possibility of formation of pinholes is small. When the light-emitting layer is formed in accordance with the vacuum vapor deposition process, in general, the conditions of the vacuum vapor deposition process can be selected in the same ranges as those described for the vacuum vapor deposition of the hole-injecting layer although the conditions are different depending on the used compound.

Next, the electron-injecting layer is formed on the light-emitting layer formed above. Similarly to the hole injecting layer and the light-emitting layer, it is preferable that the electron-injecting layer is formed in accordance with the vacuum vapor deposition process since a uniform film must be obtained. The conditions of the vacuum vapor deposition can be selected in the same ranges as those for the hole injecting layer and the light-emitting layer.

Although the aromatic amine derivatives depend on that it is contained in a light emitting layer or a hole transporting layer, it may be vapor deposited together with other materials. In addition, when the spin coating process is employed, it may be contained therein by blending it with other materials.

In the last step, the cathode is formed on the electron-injecting layer, and an organic EL device can be fabricated.

The cathode is made of a metal and can be formed in accordance with the vacuum vapor deposition process or the sputtering process. It is preferable that the vacuum vapor deposition process is employed in order to prevent the lower organic layers from damages during the formation of the film.

In the above fabrication of the organic EL device, it is preferable that the above layers from the anode to the cathode are formed successively while the fabrication system is kept in a vacuum after being evacuated.

The process for forming the layers in the organic EL device of the present invention is not particularly limited. A conventional process such as the vacuum vapor deposition process and the spin coating process can be used. The organic thin film layer comprising the compound represented by the foregoing general formula (1) used in the organic EL device of the present invention can be formed in accordance with the vacuum vapor deposition process, the molecular beam epitaxy process (the MBE process) or, using a solution prepared by dissolving the compound into a solvent, in accordance with a conventional coating process such as the dipping process, the spin coating process, the casting process, the bar coating process and the roller coating process.

The thickness of each layer in the organic thin film layer in the organic EL device of the present invention is not particularly limited. In general, an excessively thin layer tends to have defects such as pin holes, and an excessively thick layer requires a high applied voltage resultantly in decreasing the efficiency. Therefore, a thickness within the range of several nanometers to 1 μm is preferable.

The organic EL device which can be fabricated as described above emits light when a DC voltage of 5 to 40 V is applied in the condition that the anode is connected to a positive electrode (+) and the cathode is connected to a negative electrode (−). When the connection is reversed, no electric current is observed and no light is emitted at all. When an alternating voltage is applied to the organic EL device, the uniform light emission is observed only in the condition that the polarity of the anode is positive and the polarity of the cathode is negative. When an alternating voltage is applied to the organic EL device, any type of wave shape can be employed.

This invention will be described in further detail with reference to Examples, which does not limit the scope of the invention.

EXAMPLE (A) Synthesis Example 1

Synthesis of Intermediate Product (A-1) Synthesis of 2,7-dibromo-9,10-dihydrophenanthrene Dissolving 30.0 g of 9,10-dihydrophenanthrene into 200 milliliter of (MeO)$_3$PO, and a solution prepared by mixing 56.7 g of bromine with 100 milliliter of (MeO)$_3$PO was dripped into the resultant solution contained in a flask. Shading the flask from light, the reacted solution was stirred for 8 hours. As a result, a white precipitation generated. After the completion of the reaction, the white precipitation in the reacted solution was separated by filtration. After washing the resultant crystal with a use of methanol, it was vacuum dried and 32.7 g of 2,7-dibromo-9,10-dihydrophenanthrene was obtained as white crystal.

(A-2) Synthesis of 2,7-dibromophenanthrene

Preparing 32.7 g of 2,7-dibromo-9,10-dihydrophenanthrene, 24.1 g of 2,3-dichloro-5,6-dicyanobenzoquinone (DDQ) and 500 milliliter of benzene as a mixture solution, the solution was refluxed with heating under an ambient atmosphere of argon gas for 64 hours. The reacted solution was cooled down to a room temperature, and further filtered. Concentrating the filtrate by means of an evaporator, the residue was washed with a use of methanol. After refining the filtered product by means of a short column, the refined product was re-crystallized with a use of toluene and as a result, 15.5 g of 2,7-dibromophenanthrene was obtained as colorless needle crystals.

(B) Synthesis Example 2

Synthesis of Phenanthreneamine Derivative

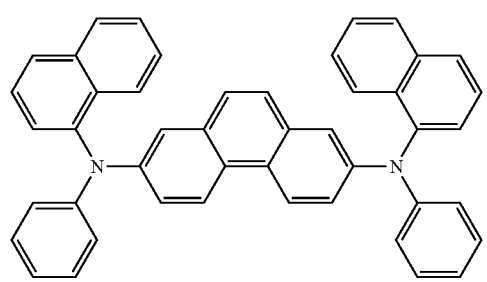
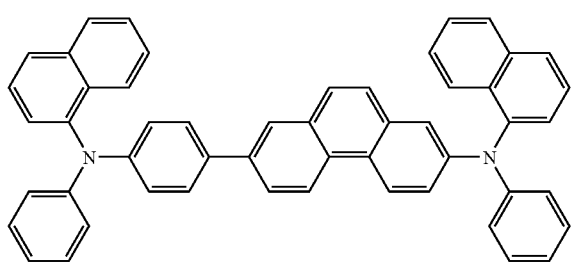

-continued
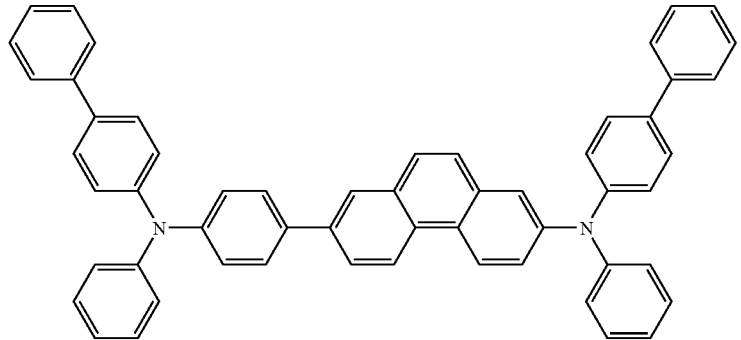
3
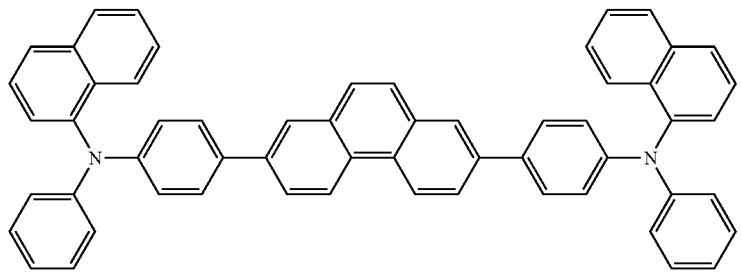
4
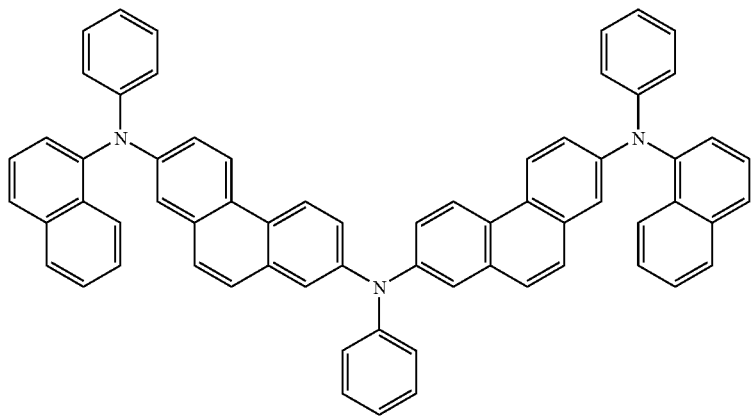
5
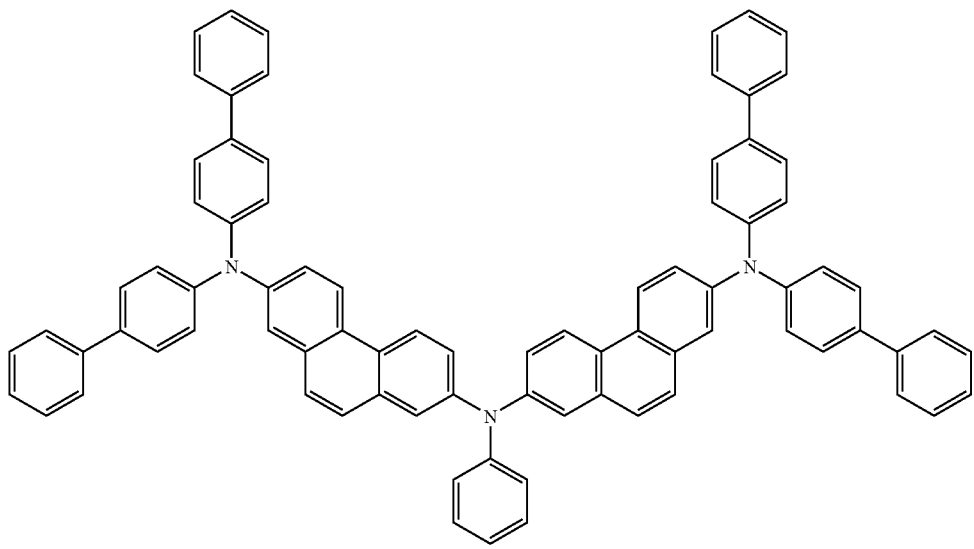
6

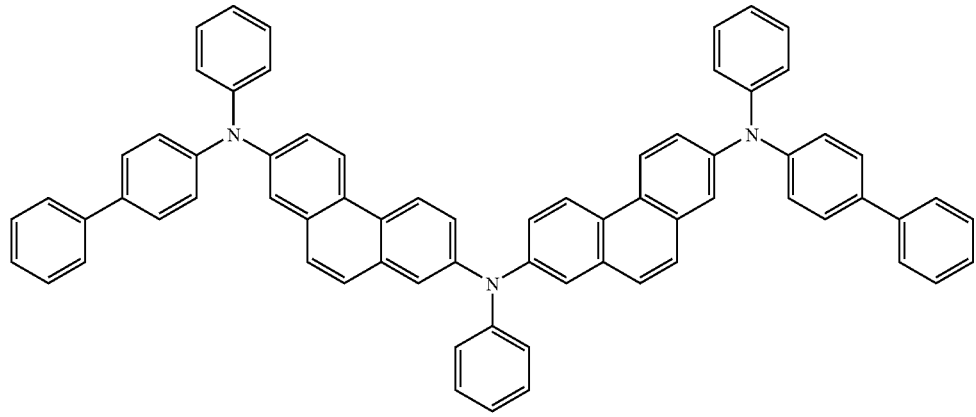
7
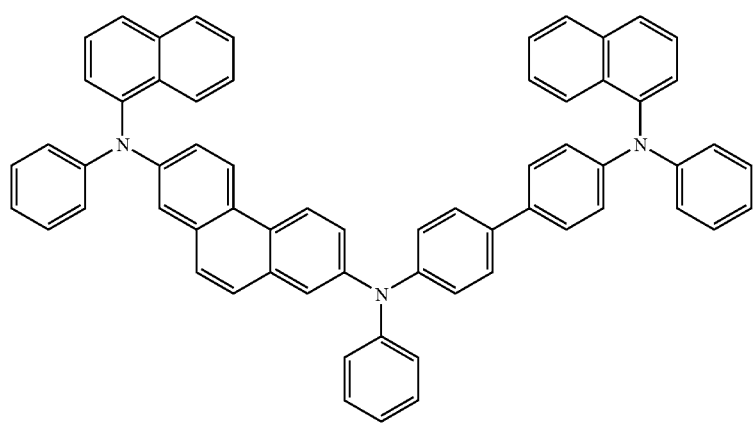
8
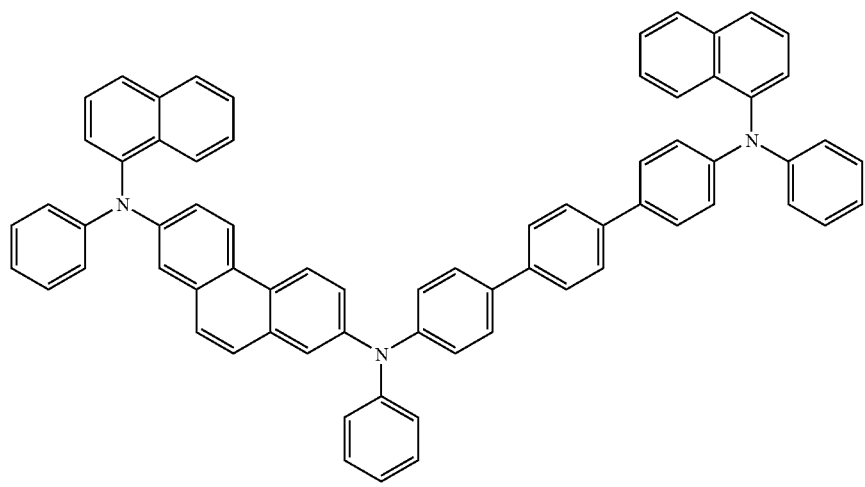
9

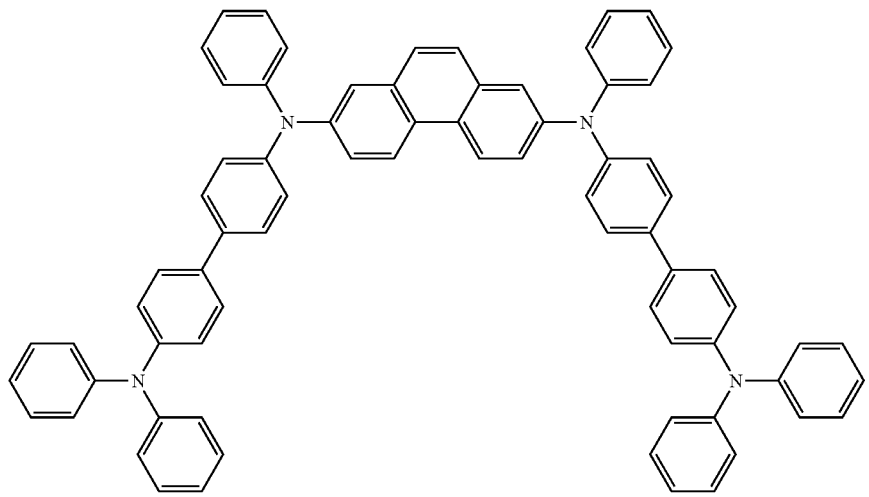

10

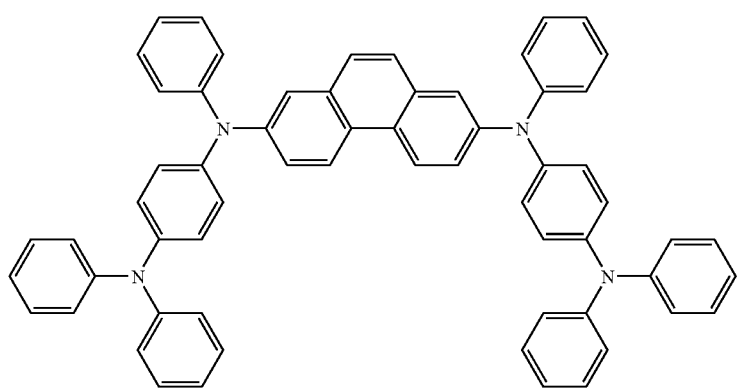

11

(B-1) Synthesis of Compound 1

Adding 0.66% by weight toluene solution in an amount of 100 microliter prepared by dissolving tri-t-butylphosphine into a mixed solution prepared by dissolving 3.36 g of 2,7-dibromophenanthrene, 5.26 g of N-phenyl-1-naphthylamine, 183 milligram of tris(dibenzylideneacetone)dipalladium (O) and 1.34 g of t-butoxysodium into toluene in an amount of 100 milliliter, the resultant solution was refluxed with heating for 5 hours. After cooling the resultant solution down to a room temperature, the precipitated solid was separated by filtration. The resultant solid was washed with uses of methanol, water, methanol and toluene sequentially and further, it was dried under a reduced pressure. After dissolving the solid in hot toluene, it was filtered while heating and then, cooling down to a room temperature, a crystal resultantly precipitated. The crystal was separated by filtration and re-crystallizing with a use of toluene, 3.26 g of pale greenish white crystal was obtained. As a result of mass spectrum analysis, the pale greenish white crystal was identified as the aimed substance, and it was recognized that m/e=612 for molecular weight of 612.26.

(B-2) Synthesis of Compound 2

(1) Synthesis of N-(4-bromophenyl)-N-phenyl-1-naphthylamine

Adding 17.6 g of N,N'-dimethylethylenediamine into a solution prepared by mixing 21.9 g of N-phenyl-1-naphthylamine, 28.2 g of 4-bromoiodobenzene, 14.4 g of t-butoxysodium, 3.81 g of copper powder and 100 milliliter of xylene, the resultant solution was refluxed with heating under ambient atmosphere of argon gas for 24 hours. After cooling the resultant solution down to a room temperature, the solution was filtered and insolubles were removed followed by concentrating the filtrate. Refining the residue by means of a silicagel column chromatography, 25.4 g of N-(4-bromophenyl)-N-phenyl-1-naphthylamine was obtained.

(2) Synthesis of 4-(N-1-naphthyl-N-phenylamino)phenylboronic acid

Under an ambient atmosphere of argon gas, cooling a solution prepared by mixing 18.7 g of N-(4-bromophenyl)-N- phenyl-1-naphthylamine, 100 milliliter of dried ethyl ether and 100 milliliter of dried toluene down to a temperature of −78° C., a hexane solution of 1.6M normal butyllithium in an amount 32.8 milliliter was dripped into the cooled solution. The reacted solution was stirred for 1 hour while warming up to a temperature of 0° C. Cooling the reacted solution down to the temperature of −78° C. again, a solution prepared by dissolving 23.5 g of boric acid triisopropyl into dried ether in an amount of 50 milliliter was dripped down to the cooled solution. The resultant solution was further stirred at a room temperature for 5 hours. Adding 100 milliliter of 1 N hydrochloric acid and after stirring the resultant solution for 1 hour, a water layer was removed. After drying an organic layer with a use of magnesium sulfate, the solvent was distilled away under a reduced pressure. Refining a resultant solid by means of a silicagel column chromatography, 10.2 g of 4-(N-1-naphthyl-N-phenylamino)phenylboronic acid was obtained.

(3) Synthesis of 2-bromo-7-(N-1-naphthyl-N-phenylamino)phenanthrene

Under an atmospheric argon gas flow, 13.7 g of N-phenyl-1-naphthylamine, 21.0 g of 2,7-dibromophenanthrene, 13.0 g of potassium carbonate, 0.400 g of copper powder and 40 milliliter of decalin were prepared as a mixed solution, and the solution reacted at a temperature of 200° C. for 6 days.

After the reaction, the resultant solution was filtered while heating and an insoluble substance was washed with a use of toluene, followed by concentration together with the filtrate. Adding 30 milliliter of toluene onto the residue, precipitated crystal was removed by filtration, and the filtrate was concentrated. Subsequently adding 100 milliliter of methanol onto the residue, a supernatant liquid was disposed as waste water after stirring and then, further adding 30 milliliter of methanol, a supernatant liquid was disposed as waste water again after stirring, followed by a column refinement and as a result, yellow powder was obtained. Dissolving the yellow powder into 15 milliliter of toluene while heating, and adding 15 milliliter of hexane, the resultant solution was cooled down. Separating a precipitated crystal by filtration, 13.4 g of 2-bromo-7-(N-1-naphthyl-N-phenylamino) phenanthrene was obtained.

(4) Synthesis of Compound 2

Under an atmospheric argon gas flow, 5.00 g of 2-bromo-7-(N-1-naphthyl-N-phenylamino)phenanthrene, 4.29 g of 4-(N-1-naphthyl-N-phenylamino) phenylboronic acid, 243 milligram of tetrakis(triphenylphosphine)palladium (O), 40 milliliter of toluene and 20 milliliter of 2M sodium carbonate aqueous solution were prepared as a mixed solution, and the solution was refluxed with heating for 8 hours. After the completion of the reaction, the solution was filtered. After washing a solid obtained by filtering with uses of water and methanol, further re-crystallizing with a use of toluene, 3.12 g of pale greenish white crystal was obtained. As a result of mass spectrum analysis, the pale greenish white crystal was identified as the aimed substance, and it was recognized that m/e=688 for molecular weight of 688.29.

(B-3) Synthesis of Compound 3

Compound 3 was synthesized in the same manner as Compound 2 except that N-biphenyl aniline was employed instead of N-phenyl-1-naphthylamine. As a result of mass spectrum analysis, the Compound 3 was identified as the aimed substance, and it was recognized that m/e=740 for molecular weight of 740.32.

(B-4) Synthesis of Compound 4

Compound 4 was synthesized in the same manner as Compound 2 except that 2,7-dibromophenanthrene was employed instead of 2-bromo-7-(N-1-naphthyl-N-phenylamino) phenanthrene. As a result of mass spectrum analysis, the Compound 4 was identified as the aimed substance, and it was recognized that m/e=764 for molecular weight of 764.32.

(B-5) Synthesis of Compound 5

Adding 0.66% by weight toluene solution in an amount of 200 microliter prepared by dissolving tri-t-butylphosphine into a mixed solution prepared by dissolving 10.4 g of 2-bromo-7-(N-1-naphthyl-N-phenylamino)phenanthrene, 0.930 g of aniline, 366 milligram of tris(dibenzylideneacetone)dipalladium (O) and 2.68 g of t-butoxysodium into toluene in an amount of 200 milliliter, the resultant solution was refluxed with heating for 5 hours. After cooling the resultant solution down to a room temperature, the precipitated solid was separated by filtration. The resultant solid was washed with uses of methanol, water, methanol and toluene sequentially and further, it was dried under a reduced pressure. After dissolving the solid in hot toluene, it was filtered while heating and then, cooling down to a room temperature, a crystal resultantly precipitated. The crystal was separated by filtration and re-crystallizing with a use of toluene, 7.26 g of pale greenish white crystal was obtained. As a result of mass spectrum analysis, the pale greenish white crystal was identified as the aimed substance, and it was recognized that m/e=879 for molecular weight of 879.36.

(B-6) Synthesis of Compound 6

Compound 6 was synthesized in the same manner as Compound 5 except that 2-bromo-7-[N,N-bis(4-biphenyl)amino]phenanthrene was employed instead of 2-bromo-7-(N-1-naphthyl-N-phenylamino)phenanthrene. As a result of mass spectrum analysis, the Compound 6 was identified as the aimed substance, and it was recognized that m/e=1083 for molecular weight of 1083.46.

(B-7) Synthesis of Compound 7

Compound 7 was synthesized in the same manner as Compound 5 except that 2-bromo-7-[N-(4-biphenyl)-N-phenylamino]phenanthrene was employed instead of 2-bromo-7-(N-1-naphthyl-N-phenylamino)phenanthrene. As a result of mass spectrum analysis, the Compound 7 was identified as the aimed substance, and it was recognized that m/e=931 for molecular weight of 931.39.

(B-8) Synthesis of Compound 8

(1) Synthesis of 4-bromo-4'-(N-1-naphthyl-N-phenylamino)biphenyl

Under an atmospheric argon gas flow, 13.7 g of N-phenyl-1-naphthylamine, 19.5 g of 4,4'-dibromobiphenyl, 13.0 g of potassium carbonate, 0.400 g of copper powder and 40 milliliter of decalin were prepared as a mixed solution, and the solution reacted at a temperature of 200° C. for 6 days. After the reaction, the resultant solution was filtered while heating and an insoluble substance was washed with a use of toluene, followed by concentration together with the filtrate. Adding 30 milliliter of toluene onto the residue, precipitated crystal was removed by filtration, and the filtrate was concentrated.

Subsequently adding 100 milliliter of methanol onto the residue, a supernatant liquid was disposed as waste water after stirring and then, further adding 30 milliliter of methanol, a supernatant liquid was disposed as waste water again after stirring, followed by a column refinement and as a result, yellow powder was obtained. Dissolving the yellow powder into 15 milliliter of toluene while heating, and adding 15 milliliter of hexane, the resultant solution was cooled down. Separating a precipitated crystal by filtration, 13.4 g of 4-bromo-4'-(N-1-naphthyl-N-phenylamino)biphenyl was obtained.

(2) Synthesis of N,N'-diphenyl-N—1-naphthylbenzidine

Adding 0.66% by weight toluene solution in an amount of 100 microliter prepared by dissolving tri-t-butylphosphine into a mixed solution prepared by dissolving 4.50 g of 4-bromo-4'-(N-1-naphthyl-N-phenylamino)biphenyl, 1.11 g of aniline, 183 milligram of tris(dibenzylideneacetone)dipalladium(O) and 1.35 g of t-butoxysodium into toluene in an amount of 100 milliliter, the resultant solution was stirred at a room temperature for 5 hours. After the completion of the reaction, the solution was filtered with a use of celite and the filtrate was extracted with toluene. Concentrating the filtrate under a reduced pressure, the resultant crude product was refined by means of a column and as a result, 3.50 g of pale yellow powder was obtained (3) Synthesis of Compound 8

Adding 0.66% by weight toluene solution in an amount of 50 microliter prepared by dissolving tri-t-butylphosphine into a mixed solution prepared by dissolving 2.37 g of 2-bromo-7-(N-1-naphthyl-N-phenylamino)phenanthrene, 2.25 g of N,N'-diphenyl-N-1-naphthylbenzidine, 91.5 milligram of tris(dibenzylideneacetone)dipalladium(O) and 0.670 g of t-butoxysodium into toluene in an amount of 50 milliliter, the resultant solution was refluxed with heating for 5 hours. After cooling the resultant solution down to a room temperature, the precipitated solid was separated by filtration. The resultant solid was washed with uses of methanol, water, methanol and toluene sequentially and further, it was dried under a reduced pressure. After dissolving the solid in hot toluene, it was filtered while heating and then, cooling down to a room temperature, a crystal resultantly precipitated. The crystal was separated by filtration and re-crystallizing with a use of toluene, 3.26 g of pale greenish white crystal was obtained. As a result of mass spectrum analysis, the pale greenish white crystal was identified as the aimed substance, and it was recognized that m/e=855 for molecular weight of 855.36.

(B-9) Synthesis of Compound 9

(1) Synthesis of 4-bromo-4"-(N-1-naphthyl-N-phenylamino)-p-terphenyl

Under an atmospheric argon gas flow, 13.7 g of N,N-diphenylamine, 24.3 g of 4,4"-dibromo-p-terphenyl, 13.0 g of potassium carbonate, 0.400 g of copper powder and 40 milliliter of decalin were prepared as a mixed solution, and the solution reacted at a temperature of 200° C. for 6 days.

After the reaction, the resultant solution was filtered while heating and an insoluble substance was washed with a use of toluene, followed by concentration together with the filtrate. Adding 30 milliliter of toluene onto the residue, precipitated crystal was removed by filtration, and the filtrate was concentrated. Subsequently adding 100 milliliter of methanol onto the residue, a supernatant liquid was disposed as waste water after stirring and then, further adding 30 milliliter of methanol, a supernatant liquid was disposed as waste water again after stirring, followed by a column refinement and as a result, yellow powder was obtained. Dissolving the yellow powder into 15 milliliter of toluene while heating, and adding 15 milliliter of hexane, the resultant solution was cooled down. Separating a precipitated crystal by filtration, 13.4 g of 4-bromo-4"-diphenylamino-p-terphenyl was obtained.

(2) Synthesis of 2-(N-1-naphthyl-N-phenylamino)-7-(N-phenylamino)phenanthrene

Adding 0.66% by weight toluene solution in an amount of 100 microliter prepared by dissolving tri-t-butylphosphine into a mixed solution prepared by dissolving 4.74 g of 4-bromo-4'-(N-1-naphthyl-N-phenylamino)biphenyl, 1.11 g of aniline, 183 milligram of tris(dibenzylideneacetone)dipalladium(O) and 1.35 g of t-butoxysodium into toluene in an amount of 100 milliliter, the resultant solution was stirred at a room temperature for 5 hours. After the completion of the reaction, the solution was filtered. The resultant solid was washed with uses of methanol, water, methanol and toluene sequentially and further, it was dried under a reduced pressure and as a result, 3.50 g of gray powder (crude product) was obtained.

(3) Synthesis of Compound 9

Adding 0.66% by weight toluene solution in an amount of 50 microliter prepared by dissolving tri-t-butylphosphine into a mixed solution prepared by dissolving 2.63 g of 4-bromo-4"-diphenylamino-p-terphenyl, 2.91 g of 2-(N-1-naphthyl-N-phenylamino)-7-(N-phenylamino)phenanthrene, 91.5 milligram of tris(dibenzylideneacetone)dipalladium(O) and 0.670 g of t-butoxysodium into toluene in an amount of 50 milliliter, the resultant solution was refluxed with heating for 5 hours. After cooling the resultant solution down to a room temperature, the precipitated solid was separated by filtration. The resultant solid was washed with uses of methanol, water, methanol and toluene sequentially and further, it was dried under a reduced pressure. After dissolving the solid into hot toluene, it was filtered while heating and then, cooling down to a room temperature, a crystal resultantly precipitated. The crystal was separated by filtration and re-crystallizing with a use of toluene, 2.26 g of pale greenish white crystal was obtained. As a result of mass spectrum analysis, the pale greenish white crystal was identified as the aimed substance, and it was recognized that m/e=931 for molecular weight of 931.39.

(B-10) Synthesis of Compound 10

(1) Synthesis of 2,7-bis(N-anilino)phenanthrene

Adding 0.66% by weight toluene solution in an amount of 100 microliter prepared by dissolving tri-t-butoxysodium into a mixed solution prepared by dissolving 3.36 g of 2,7-dibromophenanthrene, 1.11 g of aniline, 183 milligram of tris(dibenzylideneacetone)dipalladium(O) and 1.34 g of t-butylphosphine into toluene in an amount of 100 milliliter, the resultant solution was refluxed with heating for 5 hours. After cooling the resultant solution down to a room temperature, the precipitated solid was separated by filtration. The resultant solid was washed with uses of methanol, water, methanol and toluene sequentially and further, it was dried under a reduced pressure and as a result, 3.26 g of gray solid was obtained.

(2) Synthesis of Compound 10

Adding 0.66% by weight toluene solution in an amount of 100 microliter prepared by dissolving tri-t-butylphosphine into a mixed solution prepared by dissolving 1.80 g of 2,7-bis(N-anilino)phenanthrene, 4.40 g of 4-bromo-4'-(N,N-diphenylamino)biphenyl, 183 milligram of tris(dibenzylideneacetone)dipalladium(O) and 1.35 g of t-butoxysodium into toluene in an amount of 50 milliliter, the resultant solution was refluxed with heating for 5 hours. After cooling the resultant solution down to a room temperature, the precipitated solid was separated by filtration. The resultant solid was washed with uses of methanol, water, methanol and toluene sequentially and further, it was dried under a reduced pressure. After dissolving the solid into hot toluene, it was filtered while heating and then, cooling down to a room temperature, a crystal resultantly precipitated. The crystal was separated by filtration and re-crystallizing with a use of toluene, 2.20 g of pale greenish white crystal was obtained. As a result of mass spectrum analysis, the pale greenish white crystal was identified as the aimed substance, and it was recognized that m/e=998 for molecular weight of 998.43.

(B-11) Synthesis of Compound 11

Compound 11 was synthesized in the same manner as Compound 10 except that 4-bromotriphenyl amine was employed instead of 4-bromo-4'-(N,N-diphenylamino)biphenyl. As a result of mass spectrum analysis, the Compound 11 was identified as the aimed substance, and it was recognized that m/e=846 for molecular weight of 846.37.

Example 1

A glass substrate (manufactured by GEOMATEC Company) of 25 mm×75 mm×1.1 mm thickness having an ITO transparent electrode was cleaned by application of ultrasonic wave in isopropyl alcohol for 5 minutes and then by exposure to ozone generated by ultraviolet light for 30 minutes. The glass substrate having the transparent electrode lines which had been cleaned was attached to a substrate holder of a vacuum vapor deposition apparatus. On the surface of the cleaned substrate at the side having the transparent electrode, a film of Compound 1 having a thickness of 80 nanometers was formed in accordance with a resistance heating vapor deposition process so that the formed film covered the transparent electrode. The formed film of Compound 1 worked as the hole injecting layer. Over the formed film of Compound 1,9-(2-naphthyl)-10-[4-(1-naphthyl)phenyl]anthracene (abbreviated as AN-1 below) having a thickness of 40 nanometers was further formed in accordance with the resistance heating vapor deposition process. At the same time, the following amine compound D-1 having styryl group as light emitting molecule was deposited with a weight ratio of AN-1: D-1=40:2. The formed film worked as a light emitting layer. On the film formed above, a film of Alq having a thickness of 10 nanometers was formed. The formed film worked as an electron injecting layer. Thereafter, Li (the source of lithium: manufactured by SAES GETTERS Company) as a reductive dopant and Alq were binary vapor deposited and an Alq:Li film (film thickness: 10 nanometers) was formed as the electron injecting layer (or the cathode). On the Alq:Li film, metallic aluminum was deposited to form a metal cathode and an organic El device was fabricated.

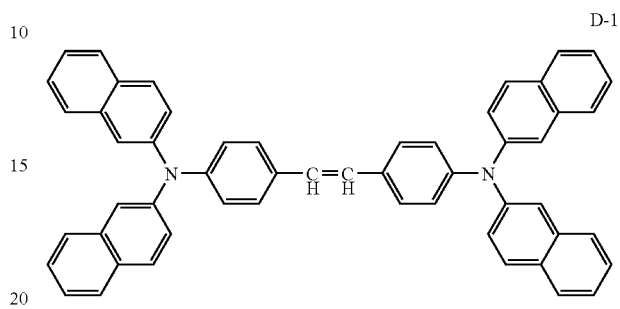

D-1

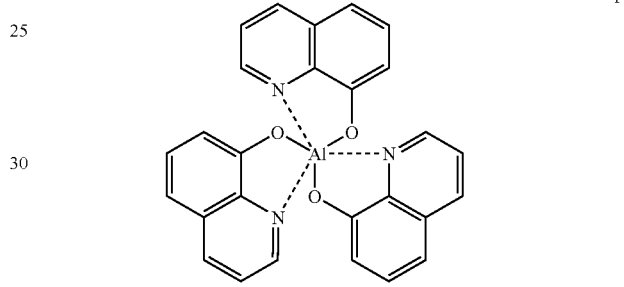

Alq

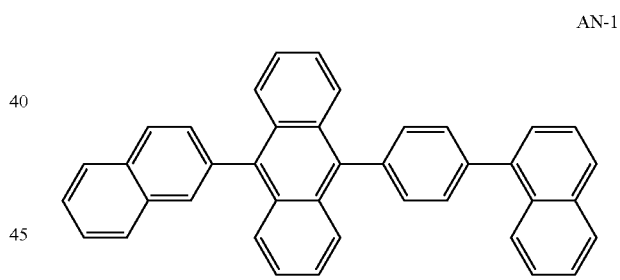

AN-1

Examples 2 to 10

Organic EL devices were fabricated in accordance with the same procedures as those conducted in Example 1 except that Compound 1 was replaced with Compounds 2 to 10 respectively.

Comparative Examples 1 to 7

Organic EL devices were fabricated in accordance with the same procedures as those conducted in Example 1 except that Compound 1 was replaced with following Compounds (A) to (G) respectively.

119 120
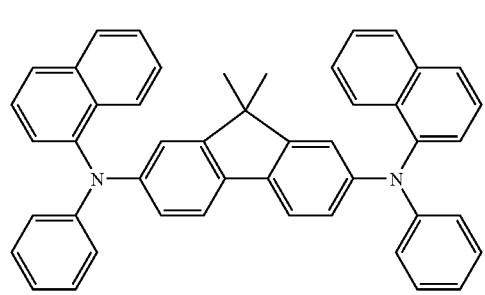
(A)
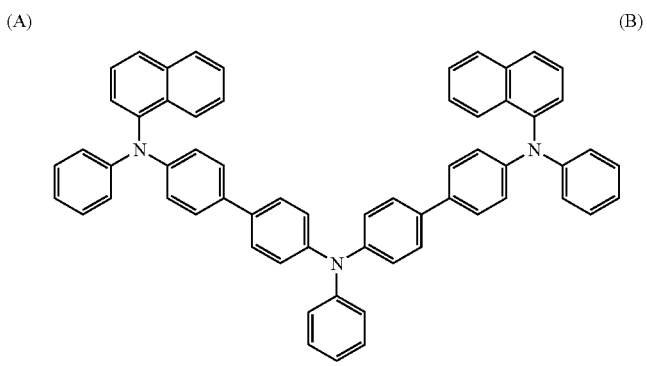
(B)
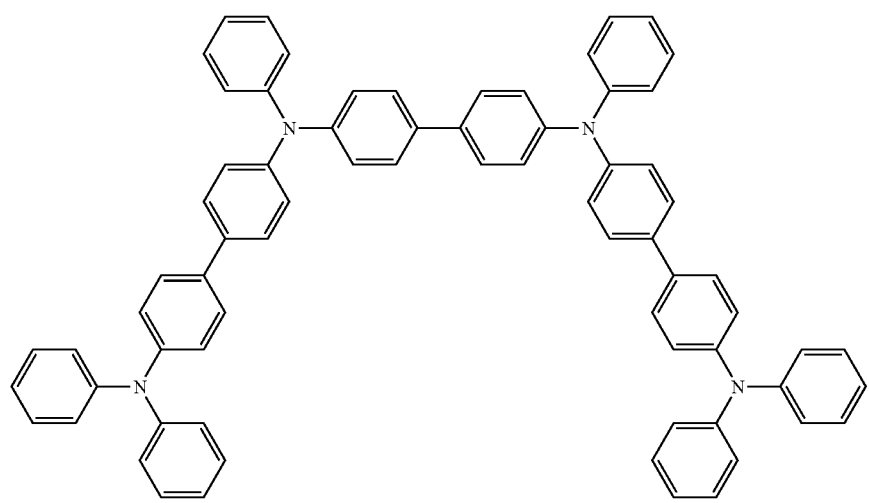
(C)
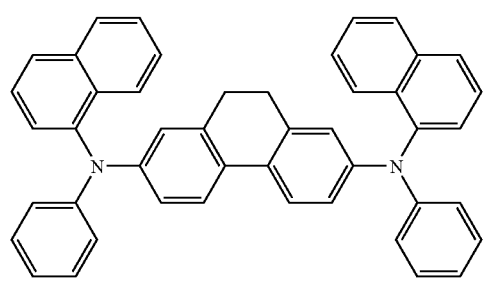
(D)
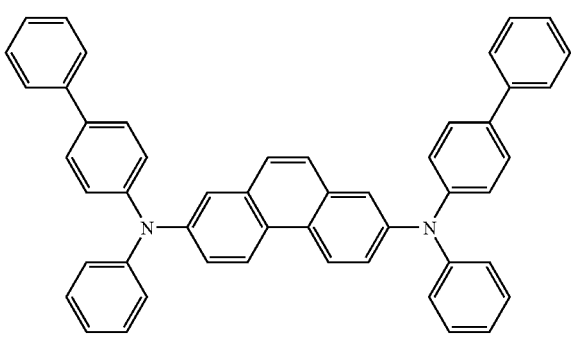
(E)
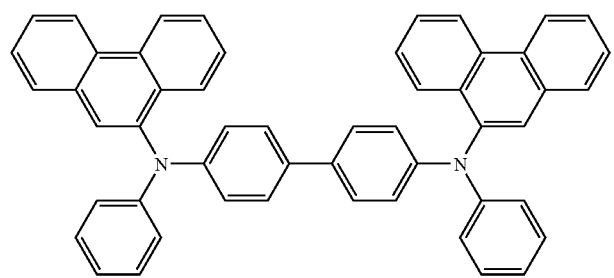
(F)

-continued

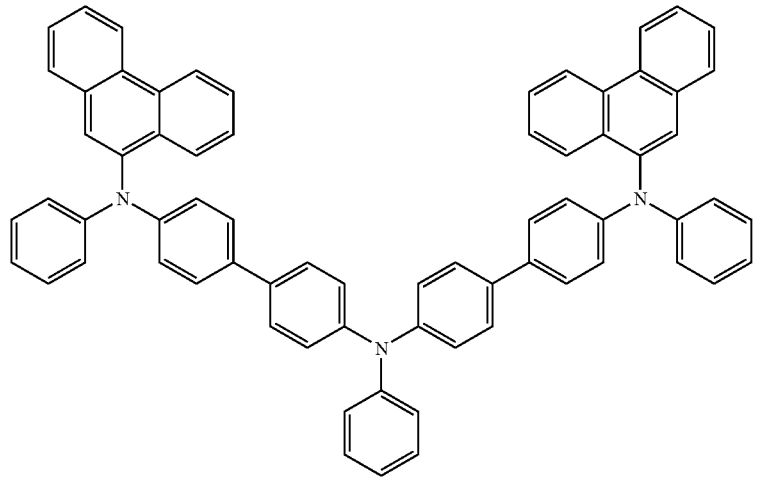
(G)

Table 1 shows performance measurement results about the organic EL devices each fabricated in Examples 1 to 10 and Comparative Examples 1 to 7 respectively.

TABLE 1

| | Compound | Current Density (mA/cm$^2$) @ 5 V | Current Efficiency (cd/A) @ 100 cd/m$^2$ | Color of Light Emission | Half Lifetime (hours) @ 1000 cd/m$^2$ |
|---|---|---|---|---|---|
| Example 1 | Compound 1 | 3.12 | 6.4 | Blue | 3500 |
| Example 2 | Compound 2 | 3.21 | 6.5 | Blue | 3500 |
| Example 3 | Compound 3 | 3.18 | 6.6 | Blue | 3500 |
| Example 4 | Compound 4 | 3.05 | 6.4 | Blue | 3500 |
| Example 5 | Compound 5 | 3.31 | 6.8 | Blue | 4000 |
| Example 6 | Compound 6 | 3.30 | 6.3 | Blue | 4000 |
| Example 7 | Compound 7 | 3.30 | 6.4 | Blue | 4000 |
| Example 8 | Compound 8 | 3.21 | 6.7 | Blue | 4000 |
| Example 9 | Compound 9 | 3.40 | 6.6 | Blue | 4000 |
| Example 10 | Compound 10 | 3.50 | 6.6 | Blue | 3500 |
| Co. Example 1 | Compound (A) | 2.32 | 5.8 | Blue | 1500 |
| Co. Example 2 | Compound (B) | 2.44 | 5.1 | Blue | 2000 |
| Co. Example 3 | Compound (C) | 2.54 | 6.2 | Blue | 1500 |
| Co. Example 4 | Compound (D) | 3.12 | 5.8 | Blue | 1000 |
| Co. Example 5 | Compound (E) | 3.11 | 6.2 | Blue | 1000 |
| Co. Example 6 | Compound (F) | 2.01 | 6.0 | Blue | 2000 |
| Co. Example 7 | Compound (G) | 2.18 | 6.1 | Blue | 2000 |

Notification: In the Table 1, "Co. Example" means "Comparative Example".

Referring the Table 1, it verifies that an employment of the compound in the present invention for a hole injecting layer provides favorable hole injection property, an enhanced current efficiency of light emission. Further, while maintaining the favorable hole injection property and the enhanced current efficiency of light emission, it also provides a prolonged lifetime. Still further, it also verifies that the structure of 2,7-phenanthrene diamine is more remarkably effective than the structure of 9-phenanthreneamine (Comparative examples 6 and 7).

Example 11

A glass substrate (manufactured by GEOMATEC Company) of 25 mm×75 mm×1.1 mm thickness having an ITO transparent electrode was cleaned by application of ultrasonic wave in isopropyl alcohol for 5 minutes and then by exposure to ozone generated by ultraviolet light for 30 minutes. The glass substrate having the transparent electrode lines which had been cleaned was attached to a substrate holder of a vacuum vapor deposition apparatus. On the surface of the cleaned substrate at the side having the transparent electrode, a film of Compound 11 having a thickness of 60 nanometers was formed in accordance with a resistance heating vapor deposition process so that the formed film covered the transparent electrode. The formed film of Compound 11 worked as the first hole injecting layer (the hole transporting layer). Subsequent to the film-forming of the film of Compound 11, a film of 4,4'-bis[N-(1-naphthyl)-N-phenylamino]biphenyl (referred to as a "film of NPD", hereunder) having a thickness of 20 nanometers was formed over the film of Compound 11 in accordance with the resistance heating vapor deposition process. The formed film of NPD worked as the second hole injecting layer (the hole transporting layer). Subsequent to the film-forming of the film of NPD, a film of AN-1 having a thickness of 40 nanometers was further formed over the film of NPD in accordance with the resistance heating vapor deposition process. At the same time, the amine compound D-1 was vapor deposited as a light emitting molecule with an weight ratio of AN-1:D-1=40:2. The formed film worked as a light emitting layer. On the film formed above, a film of Alq having a thickness of 10 nanometers was formed. The formed film worked as an electron injecting layer. Thereafter, Li (the source of lithium: manufactured by SAES GETTERS Company) as a reductive dopant and Alq were binary vapor deposited and an Alq:Li film (film thickness: 10 nanometers) was formed as the electron injecting layer (or the cathode). On the Alq:Li film, metallic aluminum was vapor deposited to form a metal cathode and an organic El device was fabricated.

Comparative Example 8

An organic EL device was fabricated in accordance with the same procedure as conducted in Example 11 except that Compound 11 was replaced with a following Compound (E).

(E)

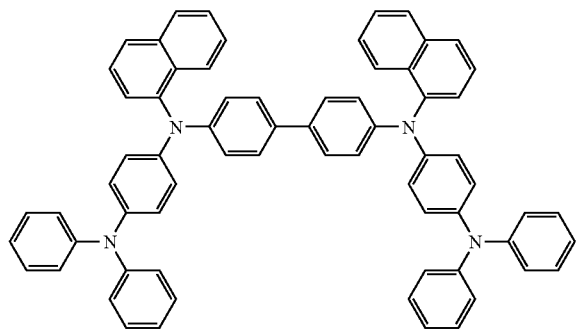

Table 2 shows performance measurement results about the organic EL devices each fabricated in Example 11 and Comparative Example 8 respectively.

TABLE 2

| | Compound | Current Density (mA/cm$^2$) @ 5 V | Current Efficiency (cd/A) @ 100 cd/m$^2$ | Color of Light Emission | Half Lifetime (hours) @ 1000 cd/m$^2$ |
|---|---|---|---|---|---|
| Example 11 | Compound 11 | 3.01 | 6.6 | Blue | 5500 |
| Co. Example 8 | Compound (E) | 2.32 | 6.2 | Blue | 5200 |

Notification: In the Table 2, "Co. Example" also means "Comparative Example".

An employment of the compound in the present invention for a hole injecting layer provides favorable hole injection property, an enhanced current efficiency of light emission and a prolonged lifetime.

As the detailed explanation above, because the organic electroluminescence device of the present invention has an organic thin film layer comprising materials containing a substituted or unsubstituted aromatic amine derivative and a material for the organic EL device both having a phenanthrenylene group in their coupling group, it reveals a prolonged lifetime, favorable hole injection property and an enhanced current efficiency of light emission as compared with the devices employing conventional compounds or materials for the organic EL device.

INDUSTRIAL APPLICABILITY

The organic EL device using the aromatic amine derivative and the material for the organic EL device according to the present invention exhibits an enhanced current efficiency of light emission and emits blue light with a prolonged lifetime. Accordingly, it is extremely useful as highly practical organic EL device. Resultantly, the EL device is useful as a flat panel light emitting member for a wall-hanging type television or as a light source of backlight and the like for display devices.

What is claimed is:

1. An aromatic amine derivative represented by the following general formula (1):

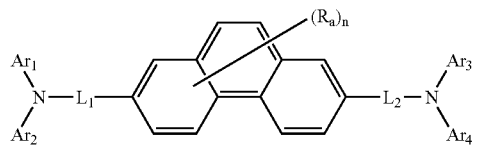

(1)

wherein Ar$_1$ to Ar$_4$ each independently represents a substituted or unsubstituted aryl group having 6 to 30 ring carbon atoms or a substituted or unsubstituted heteroaryl group having 5 to 30 ring carbon atoms;

L$_1$ represents a single bond;

L$_2$ represents a single bond, a substituted or unsubstituted arylene group having 6 to 30 ring carbon atoms or a substituted or unsubstituted heteroarylene group having 5 to 30 ring carbon atoms;

when both L$_1$ and L$_2$ are single bonds, however, a case where both Ar$_1$ and Ar$_3$ each represents a substituted or unsubstituted phenyl group and further, where both Ar$_2$ and Ar$_4$ each represents a substituted or unsubstituted biphenylyl group or a substituted or unsubstituted phenyl group is excluded;

R$_a$ represents a substituent and when R$_a$ exists two or more, they may bond each other to form a ring; and n represents an integer of 0 to 8.

2. An aromatic amine derivative represented by the following general formula (2) or by the following general formula (3):

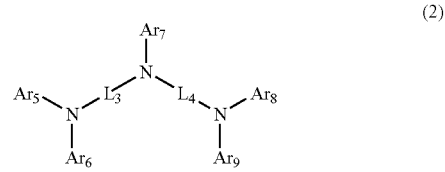

(2)

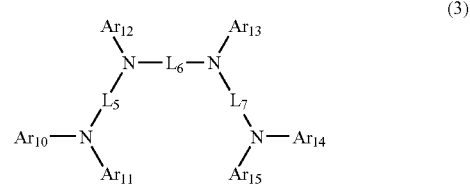

(3)

wherein Ar$_5$ to Ar$_{15}$ each independently represents a substituted or unsubstituted aryl group having 6 to 30 ring carbon atoms or a substituted or unsubstituted heteroaryl group having 5 to 30 ring carbon atoms;

L$_3$ to L$_7$ each independently represents a substituted or unsubstituted arylene group having 6 to 30 ring carbon atoms or a substituted or unsubstituted heteroarylene group having 5 to 30 ring carbon atoms; and further, at least one of L$_3$ or L$_4$ in the general formula (2) or at least one of L$_5$ to L$_7$ in the general formula (3) is a coupling group expressed by a following general formula (4):

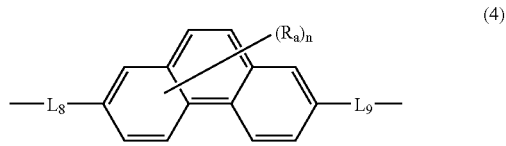

(4)

wherein L$_8$ and L$_9$ each independently represents a single bond, a substituted or unsubstituted arylene group having 6 to 30 ring carbon atoms, a substituted or unsubstituted heteroarylene group having 5 to 30 ring carbon atoms;

R$_a$ represents a substituent and when R$_a$ exists two or more, they may bond each other to form a ring; and n represents an integer of 0 to 8.

3. An aromatic amine derivative represented by the following general formula (5):

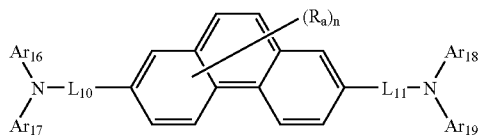
(5)

wherein $Ar_{16}$ to $Ar_{19}$ each independently represents a substituted or unsubstituted aryl group having 6 to 30 ring carbon atoms or a substituted or unsubstituted heteroaryl group having 5 to 30 ring carbon atoms;

$L_{10}$ represents a single bond;

$L_{11}$ represents a single bond, a substituted or unsubstituted arylene group having 6 to 30 ring carbon atoms or a substituted or unsubstituted heteroarylene group having 5 to 30 ring carbon atoms;

$R_a$ represents a substituent and when $R_a$ exists two or more, they may bond each other to form a ring; and n represents an integer of 0 to 8.

4. The aromatic amine derivative according to claim 2 represented by the following formula:

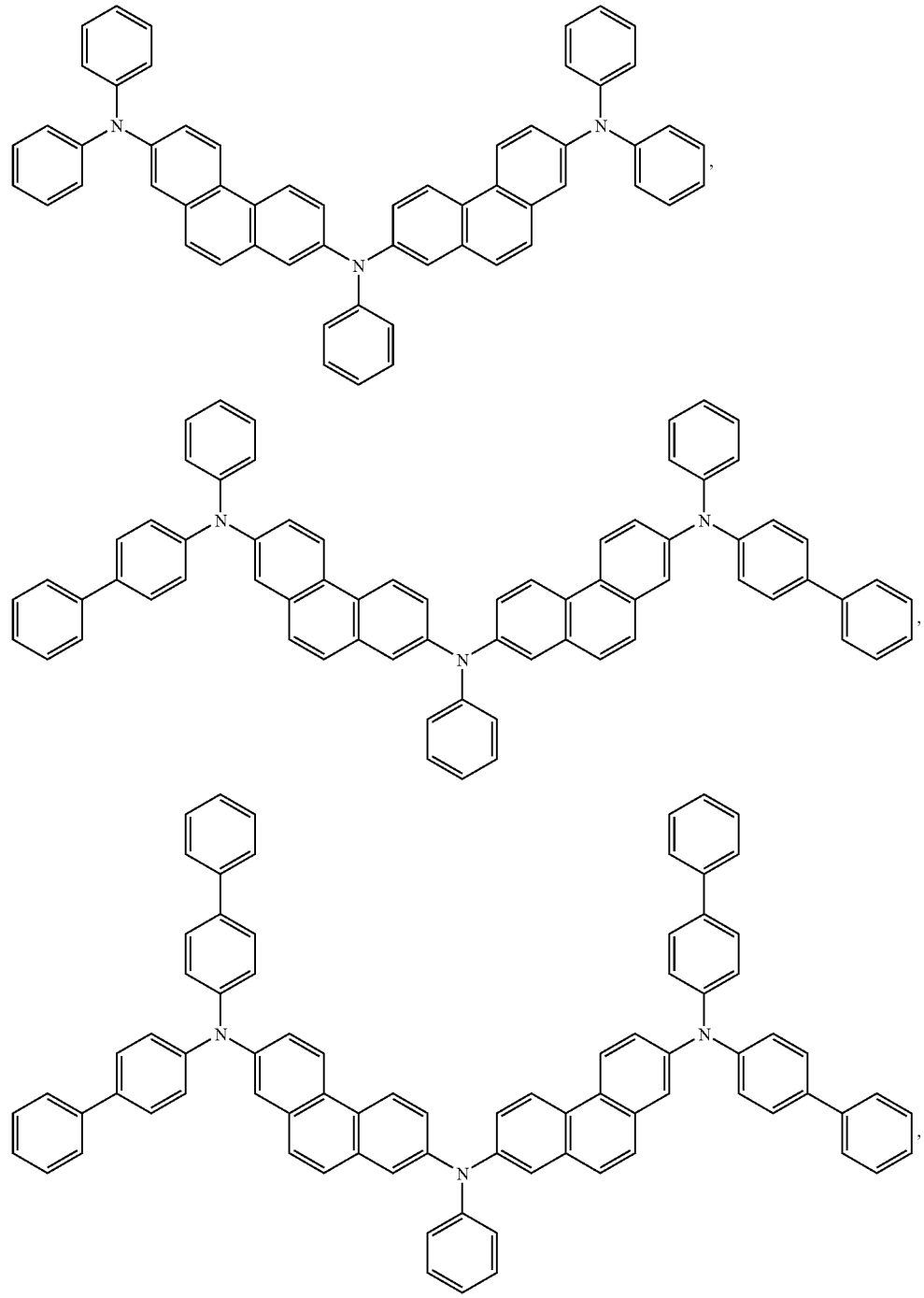

-continued
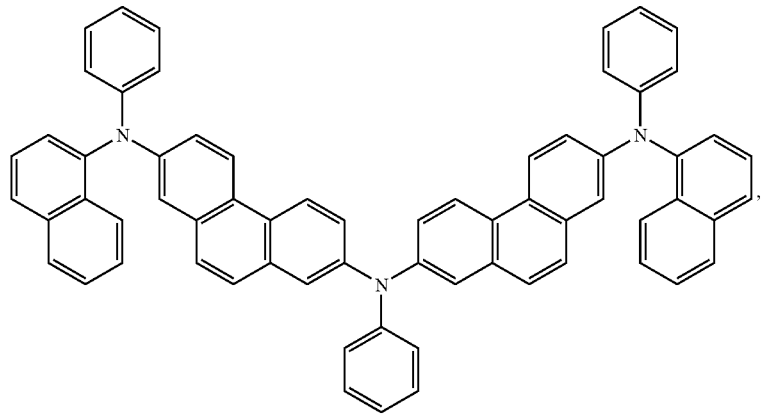
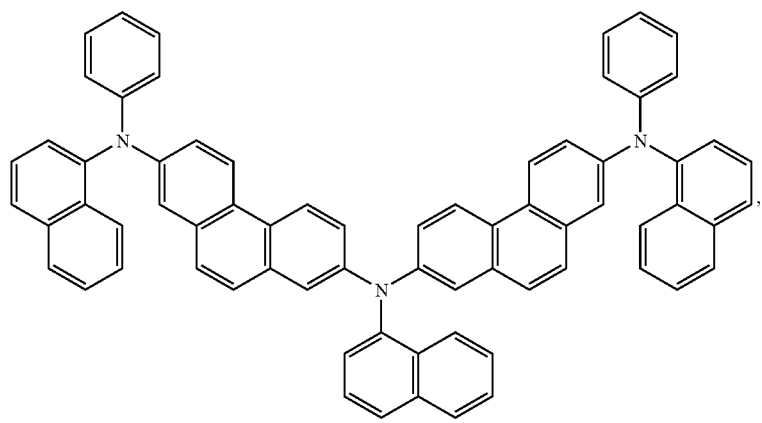
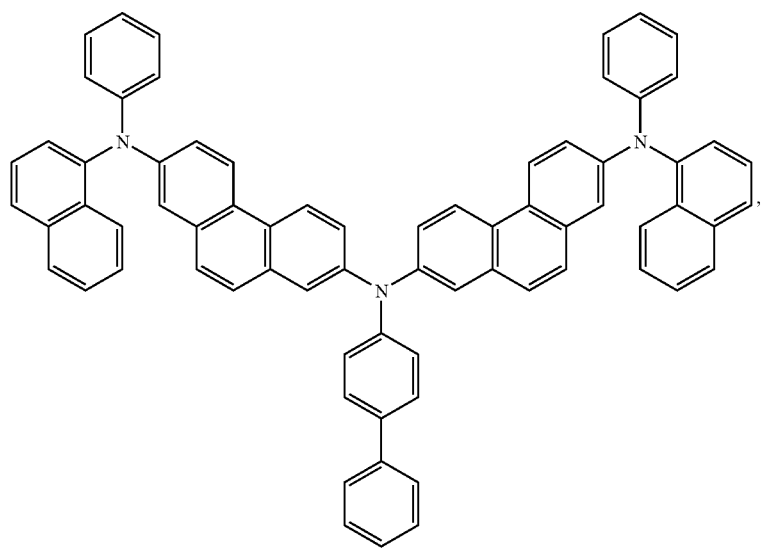

-continued
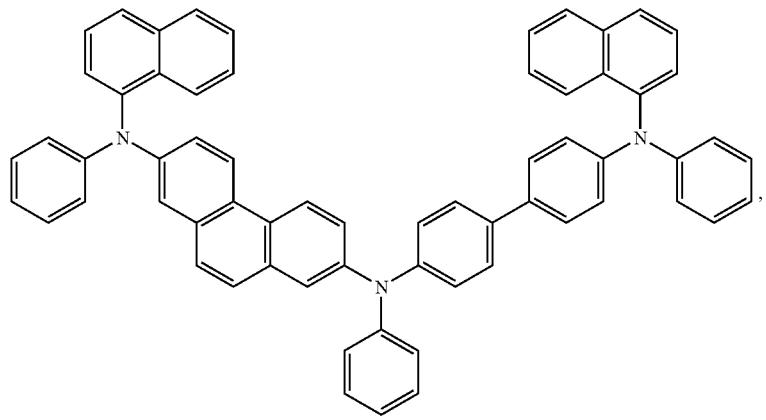
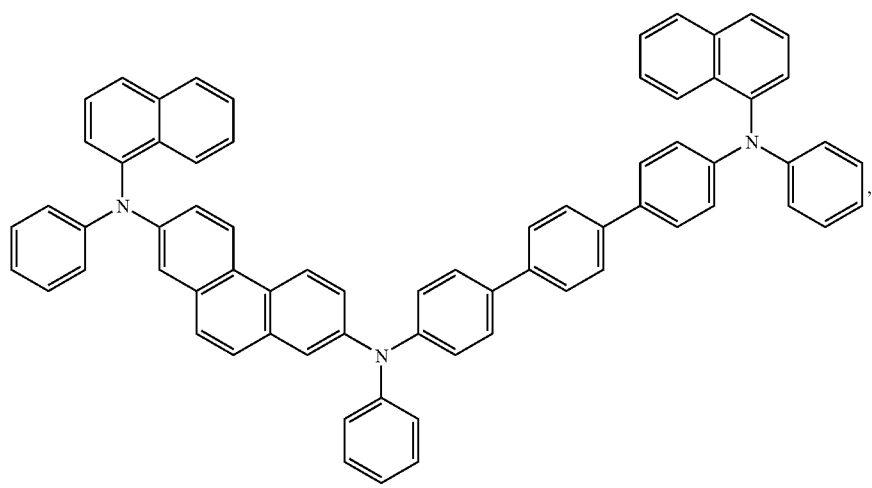
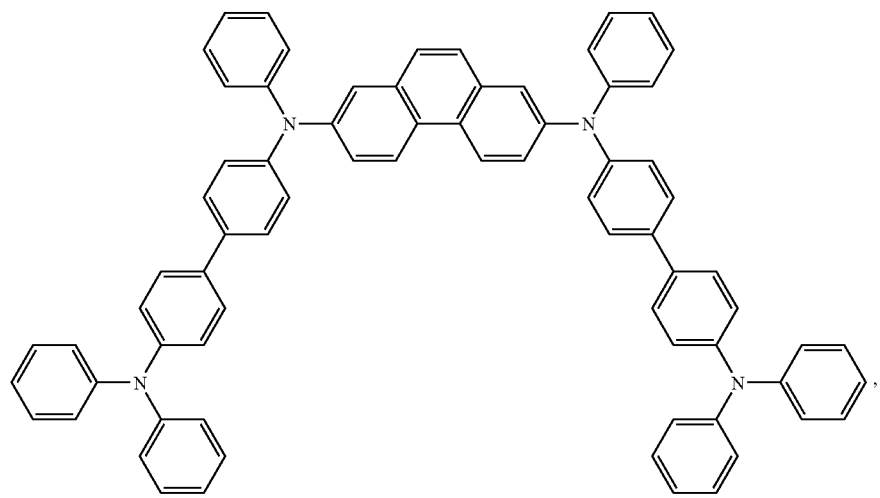

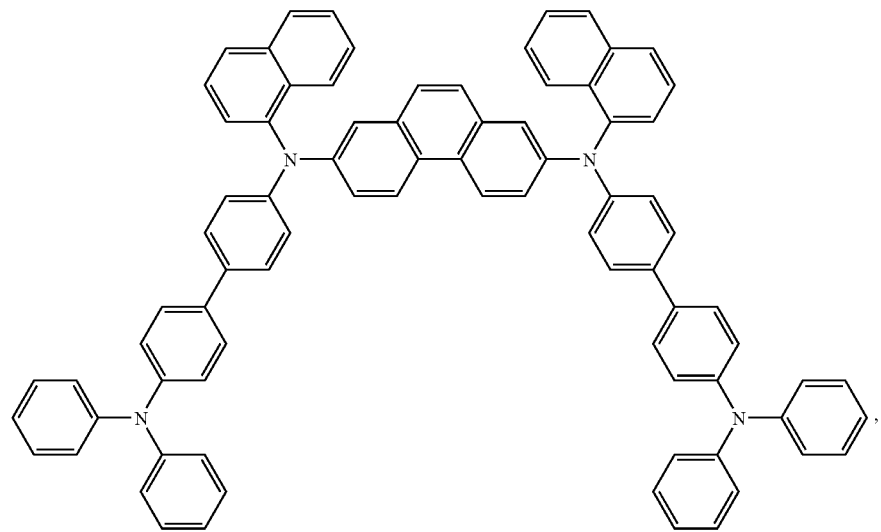
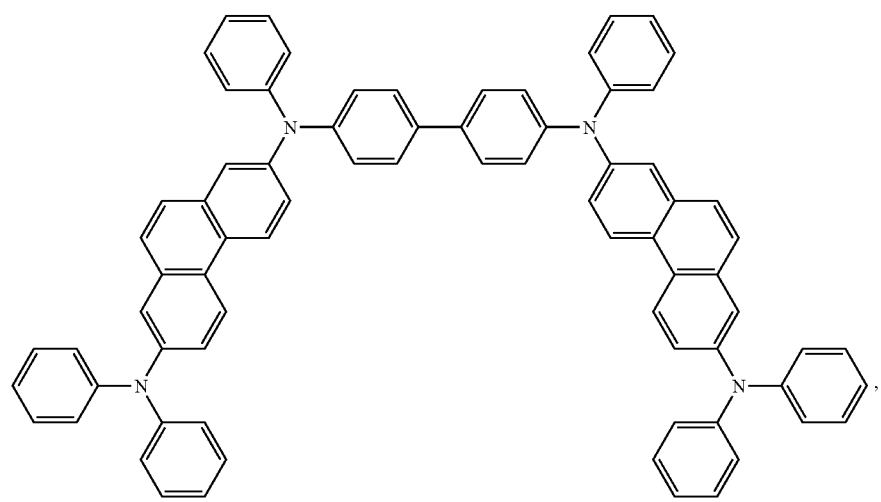
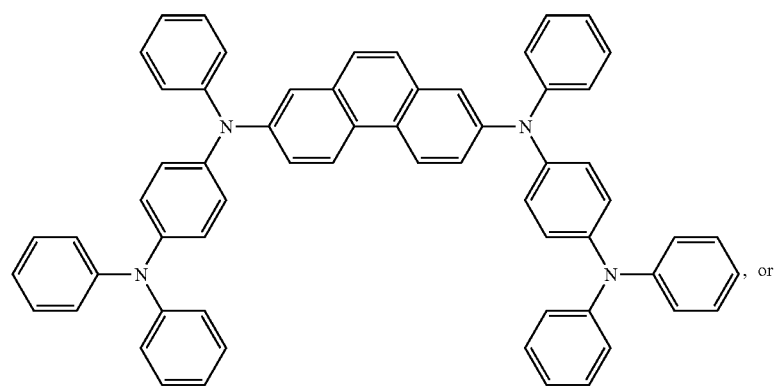
, or

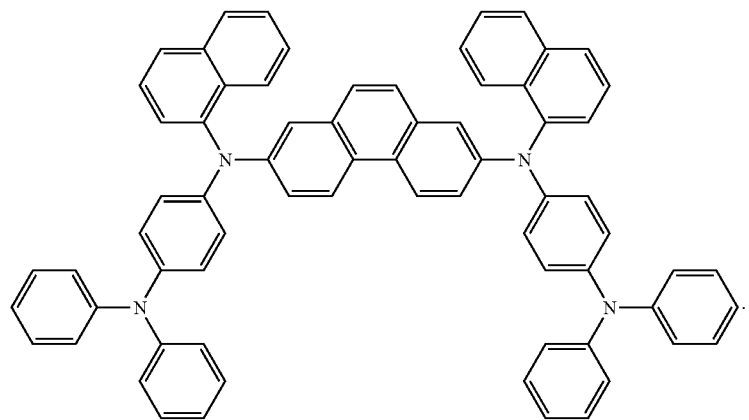
5. The aromatic amine derivative according to claim 1 represented by the following formula:
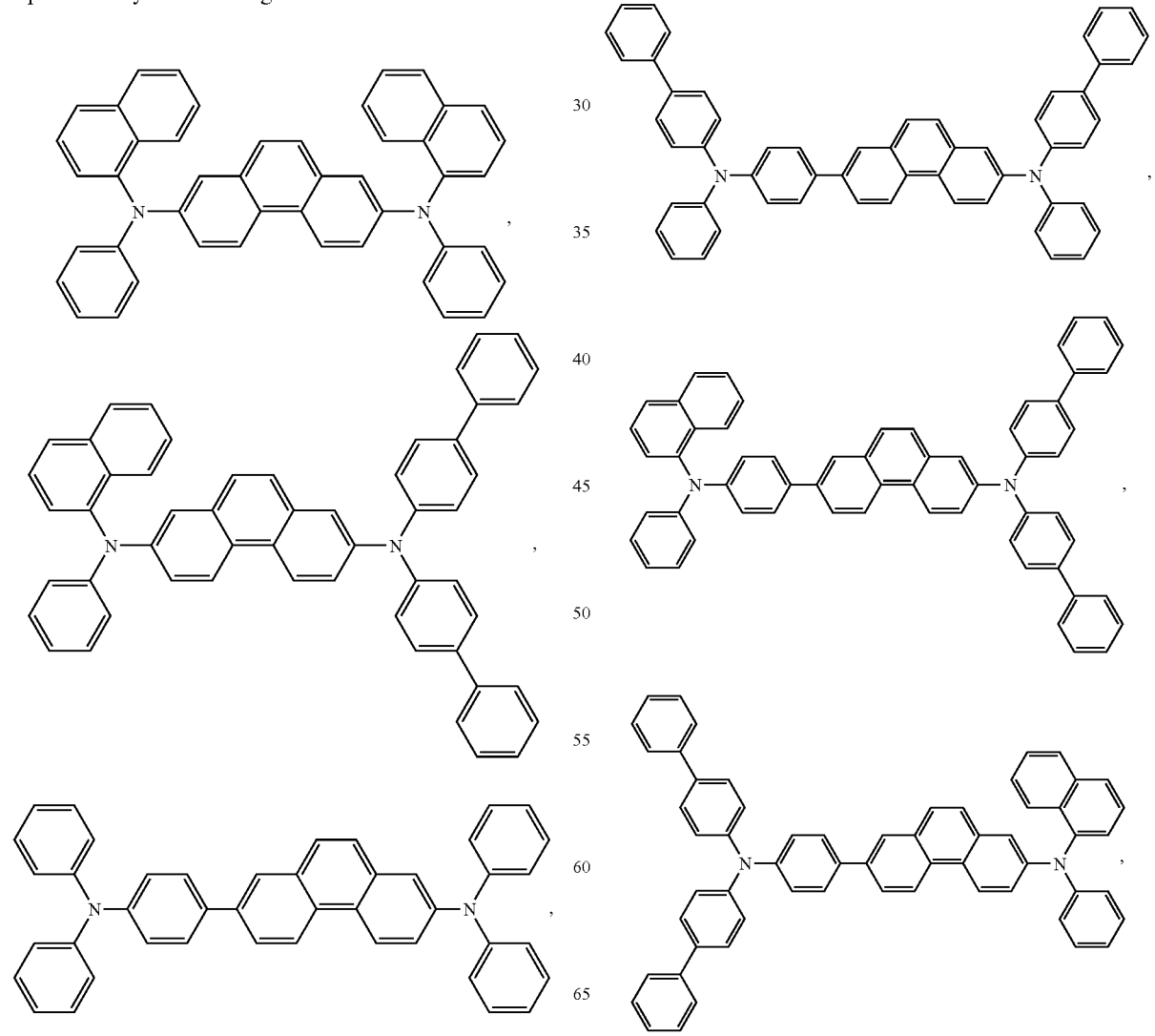

135
-continued
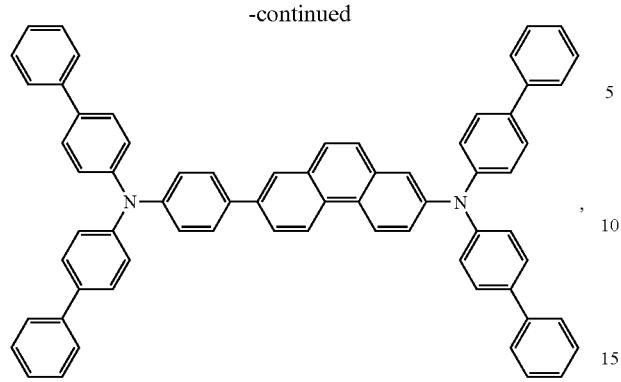
136
-continued
or
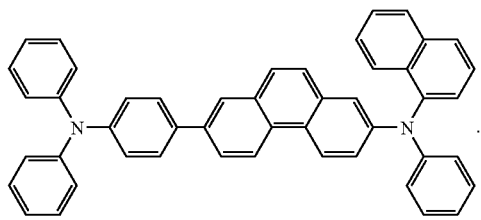
* * * * *